United States Patent
Zhao et al.

(10) Patent No.: US 11,292,802 B2
(45) Date of Patent: Apr. 5, 2022

(54) SUBSTITUTED TETRAHYDROPYRROLO[1,2-A]PYRAZINES AS ALPHA V INTEGRIN INHIBITORS

(71) Applicant: BRISTOL-MYERS SQUIBB COMPANY, Princeton, NJ (US)

(72) Inventors: Guohua Zhao, Princeton, NJ (US); James Mignone, Hamilton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 113 days.

(21) Appl. No.: 16/761,286

(22) PCT Filed: Nov. 5, 2018

(86) PCT No.: PCT/US2018/059157
§ 371 (c)(1),
(2) Date: May 4, 2020

(87) PCT Pub. No.: WO2019/094319
PCT Pub. Date: May 16, 2019

(65) Prior Publication Data
US 2021/0163501 A1 Jun. 3, 2021

Related U.S. Application Data

(60) Provisional application No. 62/582,693, filed on Nov. 7, 2017.

(51) Int. Cl.
| | | |
|---|---|---|
| *A61K 31/4985* | (2006.01) | |
| *C07D 487/04* | (2006.01) | |
| *C07D 519/00* | (2006.01) | |

(52) U.S. Cl.
CPC ......... *C07D 519/00* (2013.01); *C07D 487/04* (2013.01)

(58) Field of Classification Search
CPC .......................... A61K 31/4985; C07D 487/04
USPC .......................................... 514/249; 544/349
See application file for complete search history.

(56) References Cited

U.S. PATENT DOCUMENTS

| | | | |
|---|---|---|---|
| 5,760,029 A | 6/1998 | Jadhav et al. | |
| 6,090,944 A | 7/2000 | Hutchinson | |
| 6,114,328 A | 9/2000 | Wityak et al. | |
| 2008/0045521 A1 | 2/2008 | Arnould et al. | |
| 2008/0255183 A1 | 10/2008 | Arnould et al. | |
| 2016/0264566 A1 | 9/2016 | DeGrado et al. | |

FOREIGN PATENT DOCUMENTS

| | | | |
|---|---|---|---|
| WO | 199926945 A1 | 6/1999 | |
| WO | 199930709 A1 | 6/1999 | |
| WO | 2002060438 A1 | 8/2002 | |
| WO | 2006108040 A1 | 10/2006 | |
| WO | 2007141473 A1 | 12/2007 | |
| WO | 2011098603 A1 | 8/2011 | |
| WO | 2014154725 A1 | 10/2014 | |
| WO | 2015091426 A1 | 6/2015 | |
| WO | 2016046225 A1 | 3/2016 | |
| WO | 2016046226 A1 | 3/2016 | |
| WO | 2016046230 A1 | 3/2016 | |
| WO | 2016046241 A1 | 3/2016 | |
| WO | 2016134223 A2 | 8/2016 | |
| WO | WO-2019094319 A1 * | 5/2019 | ............. A61P 35/00 |

OTHER PUBLICATIONS

Jordan, V. C. Nature Reviews: Drug Discovery, 2, 2003, 205.*
Hackam, et al. JAMA, 296(14), 2006, 1731-1732.*
International Preliminary Report on Patentability for PCT/US2018/059157, dated May 12, 2020.
International Search Report for PCT/US2018/059157, filed Nov. 5, 2018.
Kapp et al., "Integrin Modulators: a patent review", Expert Opinion on Therapeutic Patents, vol. 23(10), pp. 1273-1295 (2013).
Piras, M. et al., "High-Affinity "Click" RGD Peptidomimetics as Radiolabeled Probes for Imaging αvβ3 Integrin", ChemMedChem, 2017, vol. 12, pp. 1142-1151.
Raboisson, P. et al., "Identification of novel short chain 4-substituted indoles as potent αvβ3 antagonist using structure-based drug design", European Journal of Medicinal Chemistry, vol. 42, pp. 334-343 (2007).

* cited by examiner

*Primary Examiner* — Douglas M Willis
(74) *Attorney, Agent, or Firm* — Gary Greenblatt

(57) ABSTRACT

The disclosure relates to compounds of formula I: Formula I which inhibit $\alpha_V$-containing integrins, and includes pharmaceutical compositions comprising these compounds and methods of treating a disease, disorder, or condition associated with dysregulation of αV-containing integrins, such as pathological fibrosis, transplant rejection, cancer, osteoporosis, and inflammatory disorders.

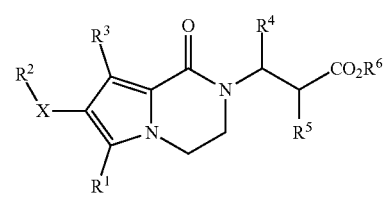

I

16 Claims, No Drawings

SUBSTITUTED TETRAHYDROPYRROLO[1,2-A]PYRAZINES AS ALPHA V INTEGRIN INHIBITORS

CROSS REFERENCE TO RELATED APPLICATION

This application is a national phase application under 35 U.S.C. § 371 of International Patent Application No. PCT/US2018/059157, filed Nov. 5, 2018, which claims priority to U.S. Provisional Application Ser. No. 62/582,693 filed Nov. 7, 2017, which are expressly incorporated fully herein by reference.

BACKGROUND OF THE INVENTION

The disclosure relates to pyrrolopyrazine compounds as $\alpha_V$ integrin inhibitors, pharmaceutical compositions comprising such compounds and to their use in therapy, especially in the treatment or prophylaxis of diseases, disorders, and conditions for which an $\alpha_V$ integrin inhibitor is indicated in a human.

Integrins belong to a large family of $\alpha/\beta$ heterodimeric transmembrane proteins that are involved in cell adhesion to a wide variety of extracellular matrix proteins, cell-cell interactions, cell migration, proliferation, survival, and in maintenance of tissue integrity (Barczyk et al. *Cell and Tissue Research* 2010, 339, 269; Srichai, M. B.; Zent, R. in *Cell-Extracellular Matrix Interactions in Cancer*, 2010). In mammals, there are 24 $\alpha/\beta$ integrin heterodimers known from various combinations of 18 alpha and 8 beta subunits. Transforming Growth Factor-$\beta$ (TGF-$\beta$) has a central role in driving a number of pathological processes underlying fibrosis, cell growth, and autoimmune diseases. Alpha V ($\alpha_V$) Integrins, that include $\alpha_V\beta1$, $\alpha_V\beta3$, $\alpha_V\beta5$, $\alpha_V\beta6$, and $\alpha_V\beta8$, are involved in a critical pathway that leads to the conversion of latent TGF-$\beta$ to its active form (Henderson, N.C.; Sheppard, D. *Biochim, Biophys. Acta* 2013, 1832, 891). Thus, antagonism of such $\alpha_V$ integrin-mediated activation of latent TGF-$\beta$ provides a viable therapeutic approach to intervene in TGF-$\beta$-driven pathological states (Sheppard, D. Eur. Resp. Rev. 2008, 17, 157; Goodman, S. L.; Picard, M. *Trends Pharmacol. Sciences* 2012, 33(7), 405; Hinz, B. *Nature Medicine* 2013, 19(12), 1567; Pozzi, A.; Zent, R. *J. Am. Soc. Nephrol.* 2013, 24(7), 1034). All five $\alpha_V$ integrins belong to a small subset (8 out of 24) of integrins that recognize the Arginine-Glycine-Aspartic acid (RGD) motif present in their native ligands such as fibronectin, vitronectin, and Latency-Associated Peptide (LAP).

The expression of $\alpha_V$ integrin subtypes varies significantly. For example, $\alpha_V\beta6$ is expressed on epithelial cells at very low levels in healthy tissue but is significantly upregulated during inflammation and wound healing. $\alpha_V\beta3$ and $\alpha_V\beta5$ are expressed on osteoclasts, endothelial, smooth muscle, and solid tumor cells, ap well as on pericytes and podocytes, while $\alpha_V\beta1$ is expressed on activated fibroblasts and mesangial cells.

Common fibrotic conditions that represent major unmet medical needs are Idiopathic Pulmonary Fibrosis (IPF), liver and kidney fibrosis, Non-Alcoholic Fatty Liver Disease (NAFLD), Non-Alcoholic Steato-Hepatitis (NASH), as well as systemic sclerosis. Two drugs, pirfenidone and nintedanib, that act by non-integrin-mediated mechanisms, have recently been approved for treatment of IPF. The present invention relates to compounds that inhibit or antagonize the action of one or more of the $\alpha_V$ integrins in the treatment of pathological conditions, such as fibrosis and cancer, mediated by these integrins.

A number of selective or nonselective small molecule, peptidic, and antibody-based inhibitors of $\alpha_V$ integrins have been reported in the literature (Kapp, T. G. et al. *Expert Opin. Ther. Patents* 2013, 23(10), 1273; O'Day, S. et al. *Brit. J. Cancer* 2011, 105(3), 346; Pickarski, M. et al. *Oncol. Rep.* 2015, 33, 2737; Wirth, M. et al. *Eur. Urol.* 2014, 897; Henderson, N. C. et al. *Nature Medicine* 2012, 19(12), 1617; Horan, G. S. et al. *Am. J. Resp. Crit. Care Med.* 2008, 177, 56; Puthawala, K. et al. *Am. J. Resp. Crit. Care Med.* 2008, 177, 82; Reed, N. I. et al. *Sci. Transl. Med.* 2015, 7(288), 288ra79; Anderson, N. A. et al. WO 2014/154725 A1, WO 2016/046225 A1, WO 2016/046226 A1, WO 2016/046230 A1, WO 2016/046241 A1).

DESCRIPTION OF THE INVENTION

The disclosure relates to compounds of formula I:

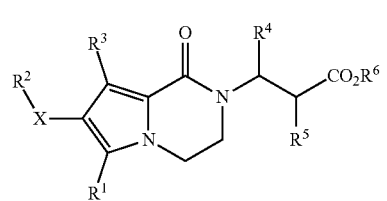

which inhibit $\alpha_V$-containing integrins, and includes pharmaceutical compositions comprising these compounds and methods of treating a disease, disorder, or condition associated with dysregulation of $\alpha V$-containing integrins, such as pathological fibrosis, transplant rejection, cancer, osteoporosis, and inflammatory disorders.

One aspect of the invention is a compound of Formula I

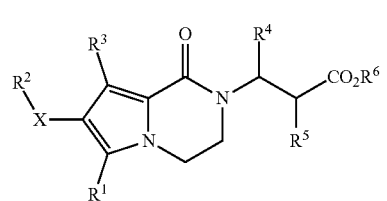

where:

X is a bond, —O—, —S—, —NR$^7$—, alkylene, alkyleneoxy, alkylenethio, or alkylene-NR$^7$—;

R$^1$ is hydrogen, halo, or alkyl;

R$^2$ is guanidinyl, (dihydroimidazolyl)amino, (imidazolyl)amino, (tetrahydropyrimidiyl)amino, (pyridinyl)amino, (benzoimidazolyl)amino, tetrahydronaphthyridinyl, naphthyridinyl, dihydropyridooxazinyl, tetrahydropyridopyrazinyl, tetrahydropyridoazepinyl, tetrahydropyridooxazepinyl, dihydroimidazoimidazolyl, or tetrahydroimidazopyrimidinyl, and is substituted with 0-2 alkyl substituents;

or R$^2$X taken together is di-((tetrahydronaphthyridinyl)methyl)methyl;

R$^3$ is hydrogen, halo, or alkyl;

R$^4$ is hydrogen or Ar$^1$;

R$^5$ is hydrogen, benzyloxycarbonylamino, or Ar$^1$SO$_2$NH;

R$^6$ is hydrogen or alkyl;

$R^7$ is hydrogen or alkyl; and $Ar^1$ is phenyl, naphthyl, dihydrobenzofuranyl, pyridinyl, pyridazinyl, pyrimidinyl, pyrazinyl, quinolinyl, or quinoxalinyl, and is substituted with 0-3 substituents selected from cyano, halo, alkyl, haloalkyl, hydroxy, alkoxy, (cycloalkyl)alkoxy, and haloalkoxy;

or a pharmaceutically acceptable salt thereof.

Another aspect of the invention is a compound of formula I where X is a bond or alkylene; $R^1$ is hydrogen or halo; $R^2$ is guanidinyl, (dihydroimidazolyl)amino, (imidazolyl)amino, (tetrahydropyrimidiyl)amino, (pyridinyl)amino, (benzoimidazolyl)amino, tetrahydronaphthyridinyl, naphthyridinyl, dihydropyridooxazinyl, tetrahydropyridopyrazinyl, tetrahydropyridoazepinyl, tetrahydropyridooxazepinyl, dihydroimidazoimidazolyl, or tetrahydroimidazopyrimidinyl, and is substituted with 0-2 alkyl substituents; $R^3$ is hydrogen; $R^4$ is hydrogen or $Ar^1$; $R^5$ is hydrogen, benzyloxycarbonylamino, or $Ar^1SO_2NH$; $R^6$ is hydrogen or alkyl; $R^7$ is hydrogen or alkyl; and $Ar^1$ is phenyl, naphthyl, dihydrobenzofuranyl, pyridinyl, pyridazinyl, pyrimidinyl, pyrazinyl, quinolinyl, or quinoxalinyl, and is substituted with 0-3 substituents selected from cyano, halo, alkyl, haloalkyl, hydroxy, alkoxy, (cycloalkyl)alkoxy, and haloalkoxy; or a pharmaceutically acceptable salt thereof.

Another aspect of the invention is a compound of formula I where X is a bond or alkylene.

Another aspect of the invention is a compound of formula I where $R^1$ is hydrogen or halo.

Another aspect of the invention is a compound of formula I where $R^2$ is (pyridinyl)amino, tetrahydronaphthyridinyl, or naphthyridinyl, and is substituted with 0-2 alkyl substituents.

Another aspect of the invention is a compound of formula I where $R^3$ is hydrogen.

Another aspect of the invention is a compound of formula I where $R^4$ is $Ar^1$ and $R^5$ is hydrogen.

Another aspect of the invention is a compound of formula I where $R^4$ is hydrogen and $R^5$ is benzyloxycarbonylamino or $Ar^1SO_2NH$.

Another aspect of the invention is a compound of formula I where $Ar^1$ is phenyl, pyridinyl, or pyrimidinyl, and is substituted with 0-3 substituents selected from cyano, halo, alkyl, haloalkyl, hydroxy, alkoxy, (cycloalkyl)alkoxy, and haloalkoxy.

For a compound of Formula I, the scope of any instance of a variable substituent, including X, $R^1$, $R^2$, $R^3$, $R^4$, $R^5$, $R^6$, $R^7$, and $Ar^1$ can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon groups having 6 to 12 carbon atoms, or a bicyclic fused ring system wherein one or both of the rings is aromatic. Bicyclic fused ring systems consist of a phenyl group fused to a four- to seven-membered aromatic or non-aromatic carbocyclic ring. Representative examples of aryl groups include but are not limited to phenyl, indanyl, indenyl, naphthyl, and tetrahydronaphthyl.

"Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention may exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention includes all isotopes of atoms occurring in the compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds of this invention can be made by various methods known in the art including those of the following schemes and in the specific embodiments section.

The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The pyrrolone analogs of Formula (I') can be prepared according to the general routes shown in Schemes 1 to 4. Depending on the particular molecule of Formula (I') being prepared, $R^1$, $R^2$—X—, $R^3$, $R^4$, and $R^5$ can either be fully installed prior to or elaborated after assemblage of the dihydropyrrolopyrazinone core structure of Formula (I'). As shown in Scheme 1, pyrrole ester 4 can be synthesized from pyrrole ester 1 via Suzuki reaction or Stille reaction as described in *Tetrahedron Lett.* 2003, 44, 427 (Handy, et al.). Alternatively pyrrole ester 4 can be made either from the corresponding methyl 1H-pyrrole-2-carboxylate by synthetic transformations known to those skilled in the art or via cyclization of vinamidinium salt 2 and glycine ester 4 using the procedures of Gupton et al. (*J. Org. Chem.* 1990, 55, 4735). Vinamidinium salt 2 is either commercially available or can be synthesized by using the procedures of Davies et al. (*J. Org. Chem.* 2001, 66, 251; hexafluorophosphate salts) or the procedures of Arnold et al. (*Collect. Czech. Chem. Commun.* 1973, 38, 2633; perchlorate salts). Pyrrole carboxylic acid 5 may be synthesized by the saponification of pyrrole ester 4 with a base such as NaOH, KOH or LiOH, in a solvent such as EtOH or MeOH, followed by acidification with an acid such as HCl or $H_2SO_4$. Compounds of Formula (I'), when $R^6$=H, can be obtained by the amide bond formation between amino ester 6 with pyrrole carboxylic acid 5 using one of the variety of procedures conducive to amide formation known to those skilled in the art, the dialkylation with compounds of formula 7, which are commercially available or can be prepared using the procedures readily known to those skilled in the art, in the presence of a base such as NaH, KOtBu, $Et_3N$, $iPr_2NEt$, $NaOH/Bu_4NBr$ etc., where X=halogen, OTs, OMs, and the subsequent deprotection of the resulting carboxylic ester. Alternatively the dialkylation product may be synthesiszed by the reaction of the resulting amide from amino ester 6 and pyrrole carboxylic acid 5 with diphenyl vinyl sulfonium triflate (8) in the presence of KOH (An et al. *Chem. Commun.*, 2011, 47, 1869). Amino esters 6 can be prepared using the methods known in the literature (for example, Hutchinson, J. H. et al. *J. Med Chem.* 2003, 46, 4790; Henderson, N. C. et al. *Nature Medicine* 2013, 19, 1617).

Scheme 1: General scheme for the preparation of compounds of Formula (I') ($R^6$ = H)

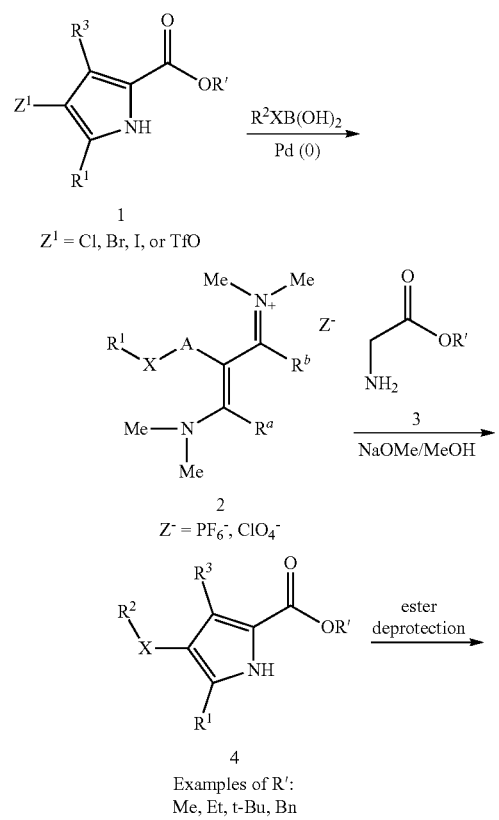

Examples of R':
Me, Et, t-Bu, Bn

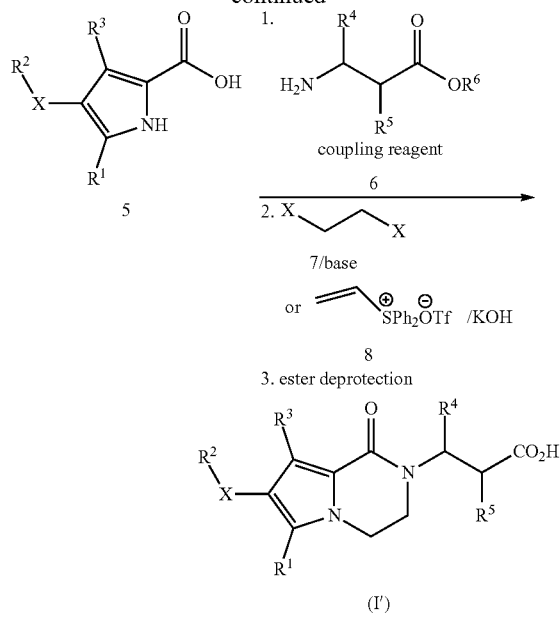

Syntheses of compounds of Formula (I') ($R^6$=H; Formulas 15, and 16) which contain tetrahydronaphthyridines as an Arginine mimetics are illustrated in Scheme 2. Pyrrole ester 4 can be converted to ketone ester 11 by coupling with a) ketone alkene 9 or b) hydroxylalkyl alkene 10 under standard Heck coupling conditions (Felpin, F.-X.; Nassar-Hardy, L.; Le Callonnec, F.; Fouquet, E. *Tetrahedron* 2011, 67, 2815-2831) and subsequent oxidation of the resulting alcohol. Naphthyridine ester 12 can be formed by the condensation of ketone ester 11 with 2-amino-3-formylpyridine under Friedlander conditions (Jose Marco-Contelles; Elena Perez-Mayoral; Abdelouahid Samadi; Maria do Carmo Carreiras; Elena Soriano (2009). "Recent Advances in the Friedlander Reaction". *Chemical Reviews*. 109 (6): 2652-2671). Naphthyridine amide 14 can be obtained by coupling of the resulting carboxylic acid from the deprotection of naphthyridine ester 12 with amino ester 6 using one of the variety of amide formation procedures known to those skilled in the art. Tetrahydronaphthyridine acids 15 (major) and 16 (minor) can be synthesized by the dialkylation with naphthyridine amide 14 in the presence of a base such as NaH, KOtBu, $Et_3N$, $iPr_2NEt$, $NaOH/Bu_4NBr$ etc., where X=halogen, OTs, OMs, or alternatively the reaction of naphthyridine amide 14 with diphenyl vinyl sulfonium triflate (8) in the presence of KOH, the selective ring reduction of the naphthyridine ring in the presence of a catalyst such as $PtO_2$ and the subsequent deprotection of the resulting carboxylic ester. Tetrahydronaphthyridine acids 15 and 16 can also be prepared by the condensation of aldehyde ester 17 with a starting material having a pre-formed naphthyridine ring, such as methyl naphthyridine, in the presence of sulfonamide, such as p-tosylamide (Yizhe Yan; Kun Xu; Yang Fang; and Zhiyong Wang. 1 *Org. Chem.* 2011, 76, 6849-6855), and subsequently employing the method similar to the one used for the conversion of 12 to 15 and 16. Alternatively, 15 and 16 can be synthesized by the selective ring reduction of 12 or 18 to give tetrahydronaphthyridine ester 19 (major) and 20 (minor) followed by the transformations similar to those used for the conversion of 12 to 15 and 16.

Scheme 2: General scheme for the preparation of compounds of Formula (I') (R⁶ = H; Formula 15 and 16) with tetrahydronaphthyridine as an Arginine mimetic (R¹)
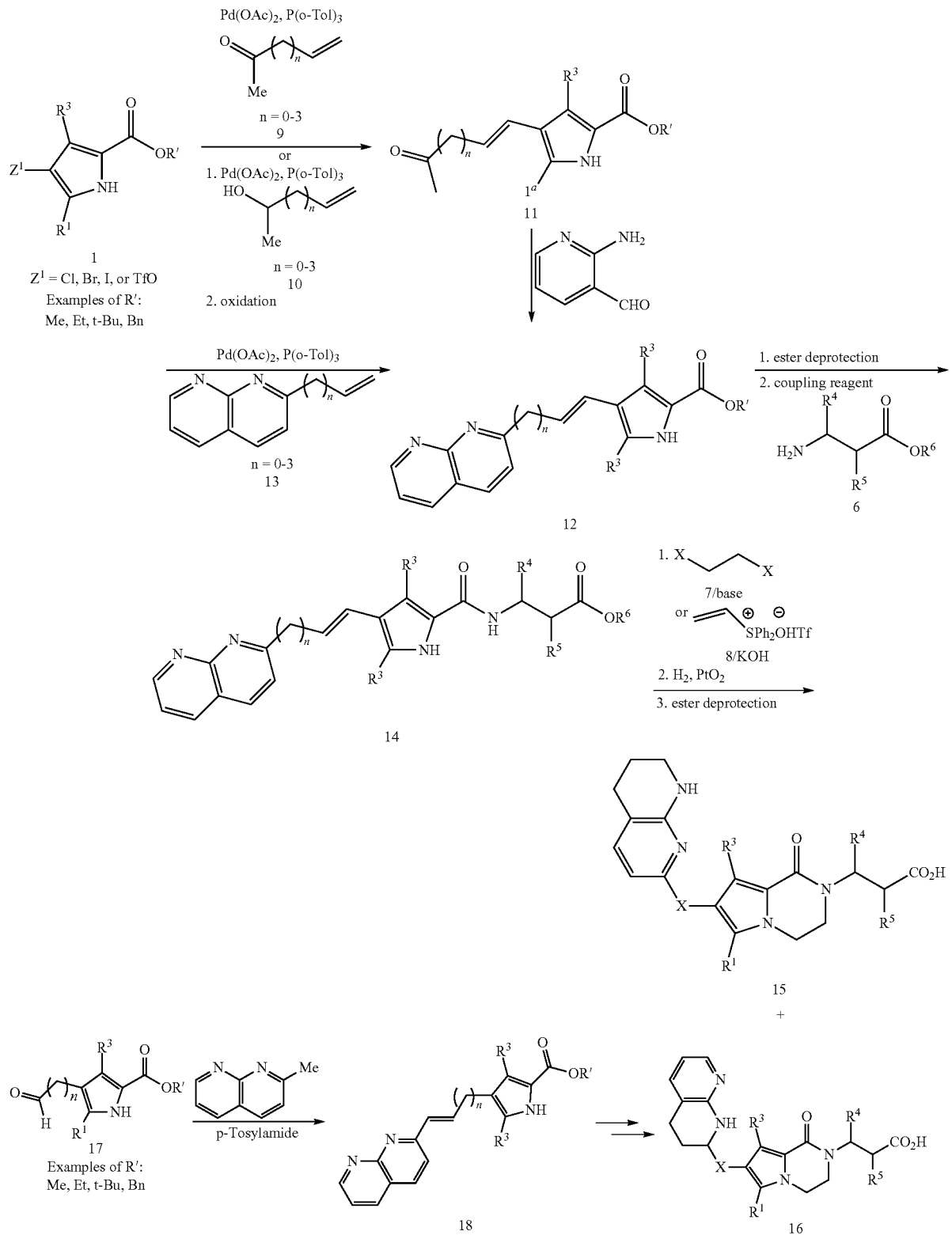

-continued

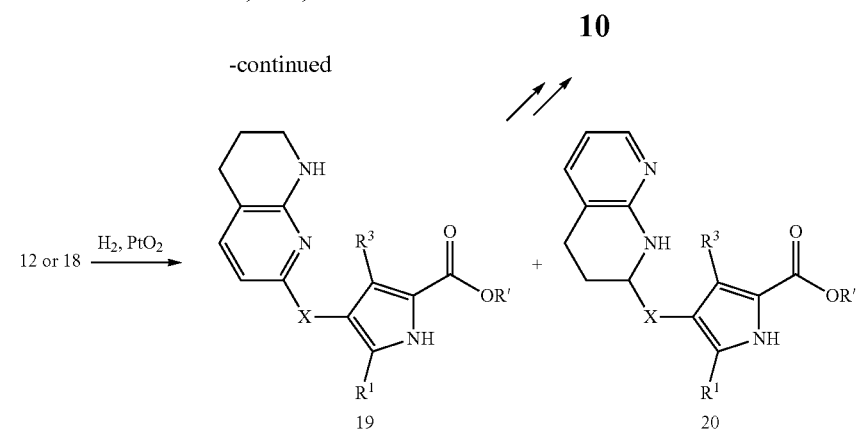

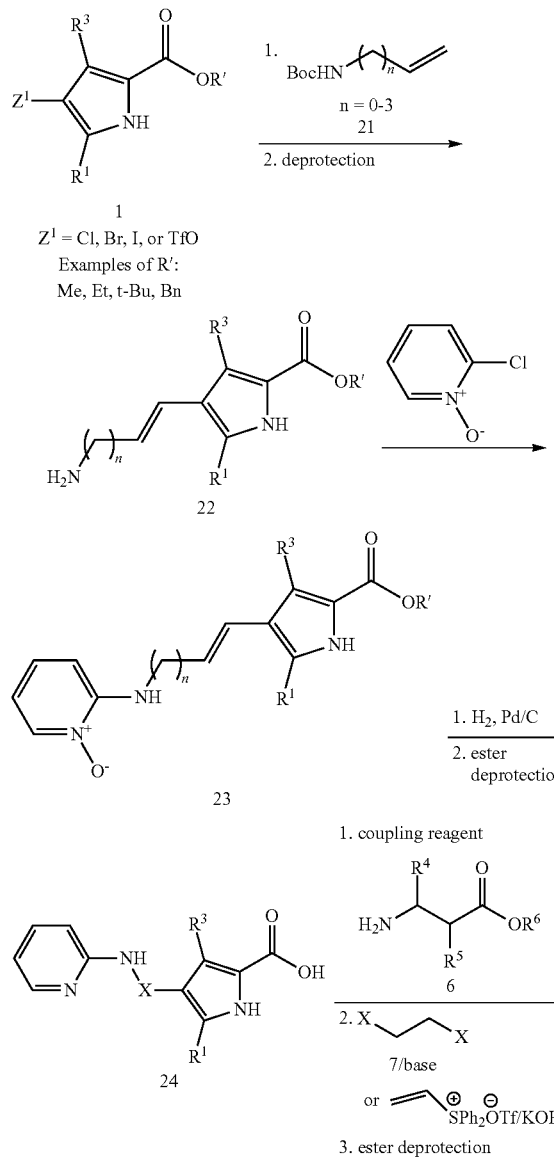

Scheme 3: Example of the synthesis of compounds of Formula (I') (R⁶ = H; Formula 25) with 2-aminopyridine as an Arginine mimetic (R¹)

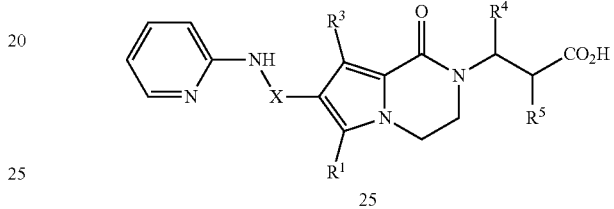

Scheme 3 describes an example of the synthesis of compounds of Formula (I') ($R^6$=H; Formula 25) with 2-aminopyridine as an Arginine mimetic. Amino ester 22 can be prepared from pyrrole ester 4 by coupling with protected amino alkene 21 under Heck reaction conditions and subsequent deprotection. N-oxide 23 can be formed by the nucleophilic substitution of 2-chloropyridine oxide with amino ester 22. Aminopyridine acid 24 can be made by the reduction of N-oxide 23 in the presence of Pd/C followed by ester deprotection. Aminopyridine acid 25 can be obtained from amino ester 6 and aminopyridine acid 24 by employing the method similar to the one used for the conversion of 5 to compounds of Formula (I') in Scheme 1.

Scheme 4: Example of the synthesis of compounds of Formula (I') ($R^6$ = H; Formula 29) with 2-aminodihydroimidazole as an Arginine mimetic (R¹)

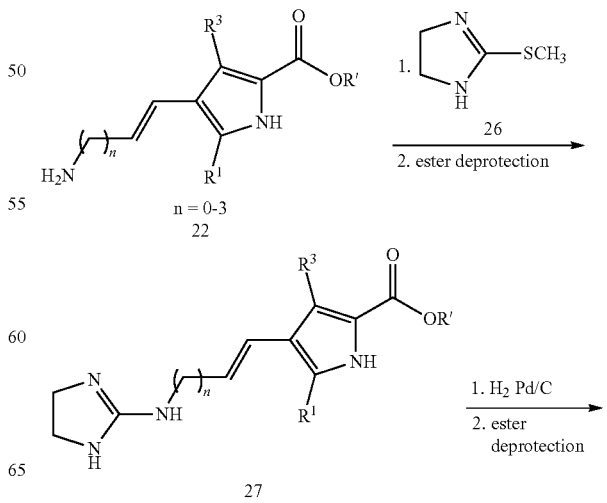

-continued

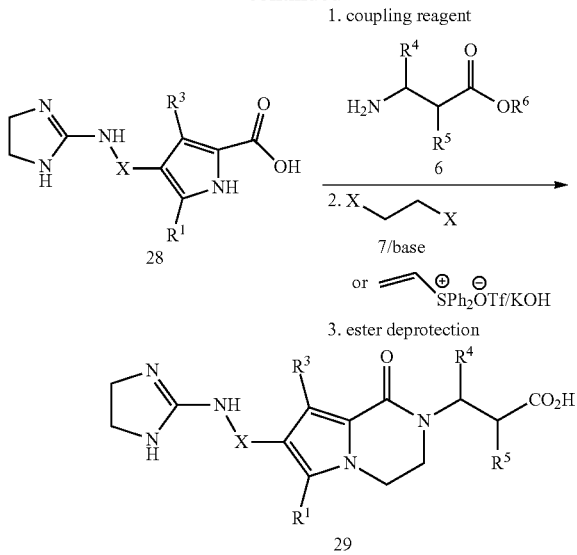

An example of the synthesis of compounds of Formula (I') (R⁶=H; Formula 29) with 2-aminodihydroimidazole as an Arginine mimetic is outlined in Scheme 4. Aminodihydroimidazole ester 27 can be made by the reaction of amino ester 22, described earlier, with a suitable electrophile such as 2-(methylthio)-4,5-dihydro-1H-imidazole followed by ester deprotection. Aminodihydroimidazole acid 28 can be prepared by the reduction of the double bond of aminodihydroimidazole ester 27 in the presence of Pd/C followed by ester deprotection. Aminopyridine acid 29 can be obtained from amino ester 6 and aminodihydroimidazole acid 28 by utilizing the method similar to the one used for conversion of 5 to compounds of Formula (I') in Scheme 1.

Biological Methods

All binding assays used the HTRF (homogeneous time resolved fluorescence) technology from Cisbio International, therefore all assays are described as HTRF binding assays. The assay results for the Examples are listed in Table 1, exemplified by human αVβ6 (?). The HTRF binding assays are established for the following integrins: human αVβ6, human αVβ1, human αVβ3, human αVβ5, and human αVβ8. All assays used the following assay buffer: 20 mM Tris, pH 7.4, 1 mM $MgCl_2$, 1 mM $MnCl_2$, 0.01% Tween 20, and 0.01% BSA. Alternatively, a SPA-based assay was used for evaluation of receptor binding.

The following describes the components and a representative procedure for the human αVβ6 HTRF binding assay: Recombinant human αVβ6 Integrin (R & D systems, 3817-AV) was biotinylated. Biotinylated human αVβ6 Integrin was added to assay vessel at a final concentration of 1.25 nM. FITC-conjugated fibronectin (Cytoskeleton, FNR02) was then added at the final concentration of 5 nM. The mixture was centrifuged at 600 rpm for three minutes using Thermo Fisher Heraeus Multifuge X3 centrifuge and then incubated at room temperature for an hour. Streptavidin Terbium (Cisbio international 610STLB) was then added at the final concentration of 0.625 nM. The resulting mixture was centrifuged at 600 rpm for three minutes using Thermo Fisher Heraeus Multifuge X3 centrifuge and then incubated at room temperature overnight in dark before reading HTRF signals.

The SPA-based assay was carried out according to the protocol and procedures similar to the ones described in the following reference with appropriate modifications to agents and ligands which are readily understood by one skilled in the art: Pachter J A, Zhang R, Mayer-Ezell R., "Scintillation proximity assay to measure binding of soluble fibronectin to antibody-captured αVβ1 integrin" *Anal Biochem.* 1995 Sep. 1; 230(1): 101-7.

TABLE 1

| Example No. | Human αVβ6 ($IC_{50}$ nM) |
|---|---|
| 1 | 3.2 |
| 2 | 0.51 |
| 3 | 2.4 |
| 4 | 80 |
| 5 | 0.59 |
| 6 | 0.98 |
| 7 | 69 |
| 8 | 25 |
| 9 | 0.60 |
| 10 | 1.3 |
| 11 | 2.3 |
| 12 | 3.2 |
| 13 | 7.2 |
| 14 | 22 |
| 15 | 23 |
| 16 | 1.8 |
| 17 | 2.6 |
| 18 | 140 |
| 19 | 6.5 |
| 20 | 3.4 |
| 21 | 5.6 |
| 22 | 1.6 |
| 23 | 1.6 |
| 24 | 1.6 |
| 25 | 4.6 |
| 26 | 53 |
| 27 | 4.8 |
| 28 | 340 |
| 29 | 0.73 |
| 30 | 1.1 |
| 31 | 12 |
| 32 | 410 |

Pharmaceutical Compositions and Therapeutic Use

Another aspect of the invention provides a method for the treatment of a disease, disorder, or condition associated with dysregulation of $α_V$ integrins in a patient in need of such treatment comprising administering a therapeutically effective amount of a compound of the present invention, or a stereoisomer, a tautomer, or a pharmaceutically acceptable salt or solvate thereof, to the patient.

Another aspect of the invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

Another aspect of the invention provides a method for eliciting an integrin receptor antagonizing effect in a patient comprising administering a therapeutically effective amount of a compound of the present invention, or a stereoisomer, a tautomer, or a pharmaceutically acceptable salt or solvate thereof, to the patient. In one embodiment, the integrin receptor antagonizing effect is an antagonizing effect to any of $α_Vβ6$, $α_Vβ1$, $α_Vβ3$, $α_Vβ5$, and $α_Vβ8$; or a combination of one or more of $α_Vβ6$, $α_Vβ1$, $α_Vβ3$, $α_Vβ5$, and $α_Vβ8$. For example, the integrin receptor antagonizing effect can be an $α_Vβ6$, $α_Vβ1$, $α_Vβ3$, $α_Vβ5$, and $α_Vβ8$ antagonizing effect.

Another aspect of the invention is where the disease, disorder, or condition is associated with fibrosis, including pulmonary, liver, renal, cardiac, dermal, ocular, and pancreatic fibrosis.

Another aspect of the invention is where the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the bladder, blood, bone, brain, breast, central nervous system, cervix, colon, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, lymphoma, leukemia, melanoma, mesothelioma, multiple myeloma, or seminoma. Examples of diseases, disorders, or conditions associated with the activity of $\alpha_V$ integrins that can be prevented, modulated, or treated according to the present invention include, but are not limited to, transplant injection, fibrotic disorders (e.g., idiopathic pulmonary fibrosis (IPF), interstitial lung disease, liver fibrosis, kidney fibrosis, skin fibrosis, systemic sclerosis), inflammatory disorders (e.g., acute hepatitis, chronic hepatitis, non-alcoholic steatohepatitis (NASH), psoriasis, irritable bowel syndrome (IBS), inflammatory bowel disease (IBD)), osteoporosis, as well as cell-proliferative disorders (e.g., cancer, myeloma, fibroma, hepatocarcinoma, leukemia, Kaposi's sarcoma, solid tumors).

The fibrotic disorders, inflammatory disorders, as well as cell-proliferative disorders that are suitable to be prevented or treated by the compounds of the present invention include, but are not limited to, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, non-alcoholic fatty liver disease (NAFLD), alcoholic or non-alcoholic steatohepatitis (NASH), acute hepatitis, chronic hepatitis, liver cirrhosis, primary sclerosing cholangitis, drug-induced hepatitis, biliary cirrhosis, portal hypertension, regenerative failure, liver hypofunction, hepatic blood flow disorder, nephropathy, pneumonia, psoriasis, irritable bowel syndrome (IBS), inflammatory bowel disease (IBD), abnormal pancreatic secretion, benign prostatic hyperplasia, neuropathic bladder disease, spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocarcinoma, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

Another aspect of the invention provides a compound of the present invention for use in therapy for the treatment of a fibrotic disorder, an inflammatory disorder, or a cell-proliferative disorder thereof.

Another aspect of the invention provides the use of a compound of the present invention for the manufacture of a medicament for the treatment of a fibrotic disorder, an inflammatory disorder, or a cell-proliferative disorder thereof.

Another aspect of the invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

Another aspect of the invention provides a combined preparation of a compound of the present invention and additional therapeutic agent(s) for simultaneous, separate or sequential use in therapy.

Another aspect of the invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

Another aspect of the invention relates to additional therapeutic agent(s) used in combined pharmaceutical compositions or combined methods or combined uses, are selected from one or more, preferably one to three, of the following therapeutic agents: inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-$\alpha_V\beta6$ monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic (32 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of NALFD, NASH, or systemic sclerosis, such as FXR agonists (for example OCA, GS-9674, and LJN452), LOXL2 inhibitors (for example simtuzumab), LPA1 antagonists (for example SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997), ACC inhibitors (for example, CP-640186 and NDI-010976), FGF21 agonist (for example, LY2405319), caspase inhibitors (for example, emricasan), NOX4 inhibitors (for example, GKT137831), MGAT2 inhibitor and bile acid/fatty acid conjugates (for example aramchol). The $\alpha_V$ inhibitors of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196).

The compounds can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

"Pharmaceutical composition" means a composition comprising a compound of the invention in combination with at least one additional pharmaceutically acceptable carrier.

"Pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

"Treating" or "treatment" refer to an approach for obtaining beneficial or desired results, including clinical results, by using a compound or a composition and include the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The compounds can be administered alone or in combination with one or more additional therapeutic agents. By "administered in combination" or "combination therapy" it is meant that the compound. When administered in combination, each component may be administered at the same time or sequentially in any order at different points in time. Thus, each component may be administered separately but sufficiently closely in time so as to provide the desired therapeutic effect.

The compounds are also useful as standard or reference compounds, for example as a quality standard or control, in tests or assays involving the $\alpha_V$ integrins. Such compounds may be provided in a commercial kit, for example, for use in pharmaceutical research involving $\alpha_V$ integrins activity. For example, as a reference in an assay to compare its known activity to a compound with an unknown activity. This would ensure the experimenter that the assay was being performed properly and provide a basis for comparison, especially if the test compound was a derivative of the reference compound.

EXAMPLES

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The compounds of the present invention can be prepared as shown in the following reaction schemes and description thereof, as well as relevant published literature procedures that may be used by one skilled in the art. Exemplary reagents and procedures for these reactions appear hereinafter and in the working Examples.

Abbreviations

The following abbreviations are employed herein:
Bn=benzyl
t-Bu=tertiary butyl
Boc=tert-Butyloxycarbonyl
Boc$_2$O=di-tert-butyl dicarbonate
Cs$_2$CO$_3$=cesium carbonate
DBU=1,8-Diazabicyclo[5.4.0]undec-7-ene
DCM or CH$_2$Cl$_2$=dichloromethane
DIAD=diisopropyl azodicarboxylate
Dess-Martin periodinane or DMP=1,1,1-Triacetoxy-1,1-dihydro-1,2-benziodoxol-3(1H)-one
DIPEA or i-Pr$_2$NEt=diisopropylethylamine
DMAP=4-dimethylaminopyridine
DMF=dimethyl formamide
Et=ethyl
Et$_3$N=triethylamine
EtOH=ethanol
Et$_2$O=diethyl ether
EtOAc=ethyl acetate
HOAc or AcOH=acetic acid
K$_2$CO$_3$=potassium carbonate
LiCl=lithium chloride
LiOAc=lithium acetate
LiOH=lithium hydroxide
Me=methyl
MeCN or ACN=acetonitrile
MeOH=methanol
MgSO$_4$=magnesium sulfate
NaBH$_4$=sodium borohydride
NaOH=sodium hydroxide
NaHCO$_3$=sodium bicarbonate
PBu$_3$=tributylphosphine
Ph=phenyl
Pd/C=palladium on carbon
Pd(OAc)$_2$=palladium(II) acetate
Ph$_3$P=triphenylphosphine
PtO$_2$=platinum dioxide
TBAF=tetra-n-butylammonium fluoride
TBDMS=tert-butyldimethylsilyl
TMS=trimethylsilyl
THF=tetrahydrofuran
TFA=trifluoroacetic acid
min=minute(s)
hr or hrs=hour(s)
L=liter
mL=milliliter
µL=microliter
g=gram(s)
mg=milligram(s)
mol=moles
mmol=millimole(s)
meq=milliequivalent
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

HPLC refers to a Shimadzu high performance liquid chromatography instrument with one of following methods:
Analytical HPLC Method #1: Phenomenex® Luna 5µ C18 4.6×50 mm, 4 min gradient, 10% MeOH/90% H$_2$O/0.1% H$_3$PO$_4$ to 90% MeOH/10% H$_2$O/0.1% H$_3$PO$_4$, 1 min hold; 4 mL/min, UV detection at 220 nm.
Analytical HPLC Method #2: YMC s5 Combiscreen ODS 6×50 mm, 4 min gradient, 10% ACN/90% H$_2$O/0.1% TFA to 90% ACN/10% H$_2$O/0.1% TFA, 1 min hold; 4 mL/min, UV detection at 220 nm.

Intermediate 1

Ethyl (S)-3-amino-3-(3-fluoro-4-methoxyphenyl)propanoate, HCl

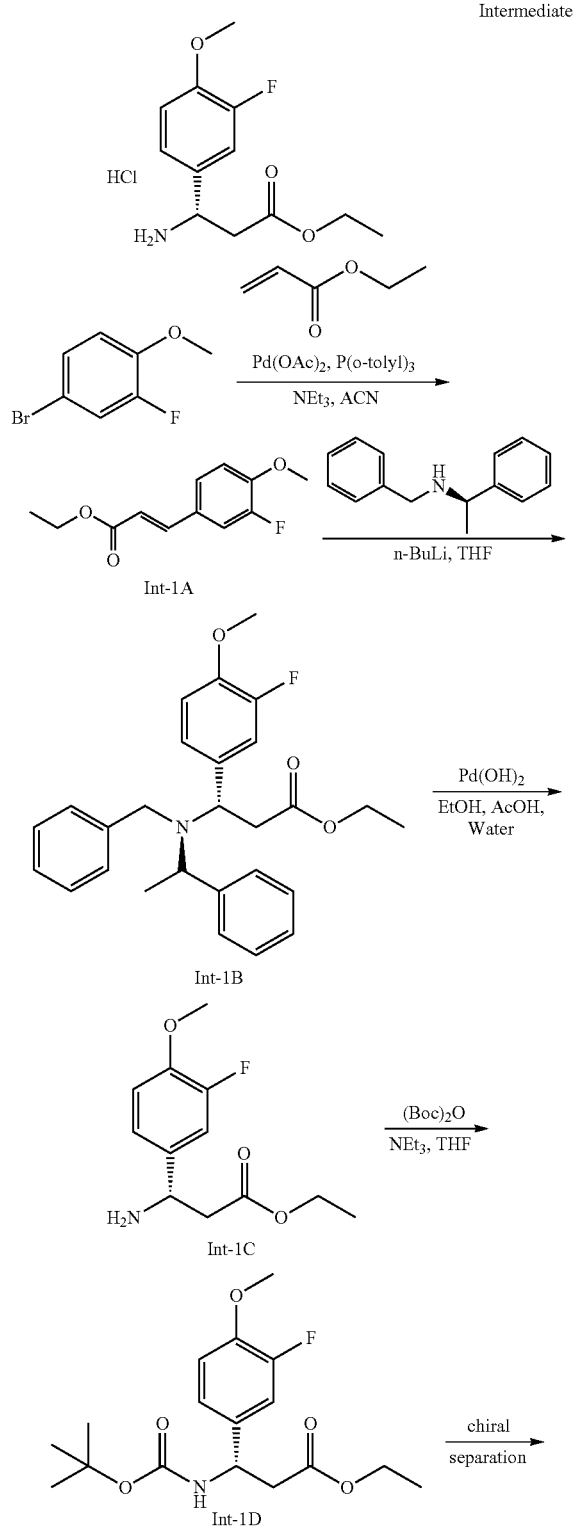

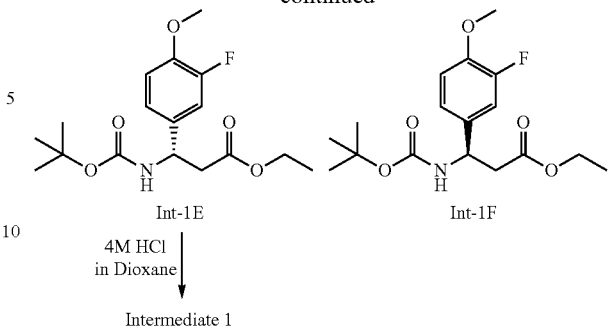

Int-1A, Int-1B, and Int-1C were prepared according to the procedure described in: Hutchinson, J. H. et. al., *J. Med. Chem.* 2003, 46, 4790.

Int-1A. Ethyl (E)-3-(3-fluoro-4-methoxyphenyl)acrylate: $^1$H NMR (500 MHz, CDCl$_3$) δ 7.59 (d, J=16.0 Hz, 1H), 7.33-7.21 (m, 2H), 6.96 (t, J=8.5 Hz, 1H), 6.30 (d, J=15.7 Hz, 1H), 4.27 (q, J=7.2 Hz, 2H), 3.93 (s, 3H), 1.34 (t, J=7.2 Hz, 3H). LCMS (ES): m/z 225.1 [M+H]$^+$.

Int-1B. Ethyl (S)-3-(benzyl((S)-1-phenylethyl)amino)-3-(3-fluoro-4-methoxyphenyl)propanoate: $^1$H NMR (500 MHz, CDCl$_3$) δ 7.59 (d, J=16.0 Hz, 1H), 7.33-7.21 (m, 2H), 6.96 (t, J=8.5 Hz, 1H), 6.30 (d, J=15.7 Hz, 1H), 4.27 (q, J=7.2 Hz, 2H), 3.93 (s, 3H), 1.34 (t, J=7.2 Hz, 3H). LCMS (ES): m/z 436.2 [M+H]$^+$.

Int-1C. Ethyl (S)-3-amino-3-(3-fluoro-4-methoxyphenyl)propanoate: $^1$H NMR (500 MHz, CDCl$_3$) δ 7.13 (dd, J=12.2, 2.1 Hz, 1H), 7.07 (dt, J=8.3, 1.5 Hz, 1H), 6.92 (t, J=8.5 Hz, 1H), 4.37 (t, J=6.7 Hz, 1H), 4.15 (qd, J=7.1, 1.0 Hz, 2H), 3.88 (s, 3H), 2.65-2.55 (m, 2H), 1.25 (t, J=7.2 Hz, 3H). LCMS (ES): m/z 242.1 [M+H]$^+$.

Int-1D. Ethyl (S)-3-(tert-butoxycarbonyl)amino)-3-(3-fluoro-4-methoxyphenyl)propanoate: To a 0° C. solution of Int-1C (31.8 g, 132 mmol) in THF (189 mL) were added triethylamine (20.2 mL, 145 mmol) and (Boc)$_2$O (30.6 mL, 132 mmol). After stirring at room temperature for 18.5 h, the reaction was diluted with EtOAc, washed with water, 10% citric acid and brine. The organic layer was dried over anhydrous Na$_2$SO$_4$ and concentrated in vacuo to give Int-1D.

Int-1E. (S)-Ethyl 3-((tert-butoxycarbonyl)amino)-3-(3-fluoro-4-methoxyphenyl)propanoate: Int-1D was purified by preparative chiral SFC (Column: Whelko-RR (5×50 cm, 10 uM, #4080), BPR Pressure: 100 bars, Temperature: 35° C., Flow rate: 300 mL/min, Mobile Phase: CO$_2$/MeOH (70/30), Detector Wavelength: 220 nm; Separation Program: stack injection; Injection: 4 mL with cycle time: 2 mins; Sample preparation: 44.4 g/310 mL MeOH:DCM (9:1), 143.2 mg/mL; Throughput: 16.3 g/hr) to afford Int-1E (41.1 g, 91%) as a white solid: $^1$H NMR (500 MHz, CDCl$_3$) δ 7.09-6.97 (m, 2H), 6.94-6.87 (m, 1H), 5.47 (br. s., 1H), 5.03 (br. s., 1H), 4.09 (q, J=7.2 Hz, 2H), 3.88 (s, 3H), 2.92-2.70 (m, 2H), 1.44 (s, 9H), 1.20 (t, J=7.2 Hz, 3H). LCMS (ES): m/z 364.1 [M+Na]$^+$. >99% ee. [α]$_D^{20}$ −27.36° (c 1.54, CHCl$_3$).

Int-1F. Ethyl (R)-3-((tert-butoxycarbonyl)amino)-3-(3-fluoro-4-methoxyphenyl)propanoate: The above preparative chiral SFC separation yielded the (R)-enantiomer (Int-1F, 1.5 g, 3%) as a white solid: $^1$H NMR (500 MHz, CDCl$_3$) δ 7.10-6.97 (m, 2H), 6.95-6.86 (m, 1H), 5.47 (br. s., 1H), 5.02 (d, J=8.0 Hz, 1H), 4.09 (q, J=7.0 Hz, 2H), 3.88 (s, 3H), 2.91-2.69 (m, 2H), 1.47-1.37 (m, 9H), 1.20 (t, J=7.2 Hz, 3H). LCMS (ES): m/z 364.1 [M+Na]⁺. 96.4% ee. [α]$_D^{20}$+20.76° (c 1.54, CHCl$_3$).

Intermediate 1: A solution of Int-1E (1.0 g, 2.93 mmol) in 4 M HCl in dioxane (48 mL) was stirred at room temperature for 1 h. The solvent was removed in vacuo and the residue was dried under vacuum. The residue was dissolved in EtOH (10 mL), concentrated in vacuo and dried under vacuum to yield Intermediate 1 (0.801 g, 98%) as a white solid. ¹H NMR (500 MHz, CDCl$_3$) δ 8.80 (br. s., 3H), 7.37-7.28 (m, 2H), 6.95 (t, J=8.5 Hz, 1H), 4.68 (t, J=6.9 Hz, 1H), 4.08 (q, J=7.1 Hz, 2H), 3.88 (s, 3H), 3.22 (dd, J=16.6, 6.2 Hz, 1H), 3.00 (dd, J=16.5, 7.7 Hz, 1H), 1.18 (t, J=7.2 Hz, 3H). LCMS (ES): m/z 242.1 [M+H]⁺. >99% ee. [α]$_D^{20}$+11.82° (c 1.54, CHCl$_3$).

Intermediate 2

Ethyl (R)-3-amino-3-(3-fluoro-4-methoxyphenyl)propanoate, HCl

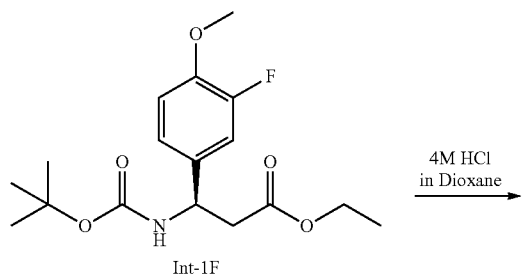

Intermediate 2: Using the procedure described for synthesis of Intermediate 1, (R)-ethyl 3-((tert-butoxy carbonyl)amino)-3-(3-fluoro-4-methoxyphenyl)propanoate (Int-1F, 1.5 g, 4.39 mmol) and 4 M HCl in dioxane (48 mL) yielded Intermediate 2 (1.16 g, 95%) as a white solid: ¹H NMR (500 MHz, CDCl$_3$) δ 8.81 (br. s., 3H), 7.37-7.27 (m, 2H), 7.01-6.88 (m, 1H), 4.68 (br. s., 1H), 4.08 (q, J=7.1 Hz, 2H), 3.88 (s, 3H), 3.23 (dd, J=16.6, 6.2 Hz, 1H), 3.01 (dd, J=16.6, 7.6 Hz, 1H), 1.18 (t, J=7.0 Hz, 3H). LCMS (ES): m/z 242.1 [M+H]⁺. 96.4% ee. [α]$_D^{20}$-11.26° (c 1.54, CHCl$_3$).

Intermediate 3

Ethyl (S)-3-amino-3-(6-methoxypyridin-3-yl)propanoate

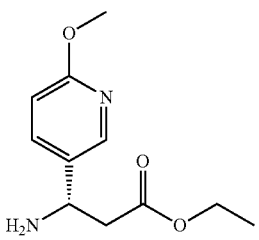

Intermediate 3 was prepared using the procedure described for Intermediate 1. ¹H NMR (500 MHz, CDCl$_3$) δ 8.14 (d, J=2.2 Hz, 1H), 7.66 (dd, J=8.5, 2.5 Hz, 1H), 6.75 (d, J=8.5 Hz, 1H), 4.46 (dd, J=8.8, 5.0 Hz, 1H), 4.15 (q, J=7.2 Hz, 2H), 3.93 (s, 3H), 2.82 (dd, J=16.2, 8.8 Hz, 1H), 2.72-2.56 (m, 1H), 1.24 (t, J=7.2 Hz, 3H). HPLC retention time (Method #1): 1.132 min.; LCMS (ES): m/z 225.0 [M+H]⁺.

Intermediate 4

Ethyl (R)-3-amino-3-(3-bromo-5-(tert-butyl)phenyl)propanoate

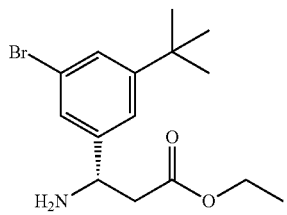

Intermediate 4 was prepared according to the procedure described in: Henderson, N.C. et. al., *Nature Medicine* 2013 19, 1617.

Intermediate 5

(±)-Methyl 3-amino-3-(3,5-dichlorophenyl)propanoate

Intermediate 6

Methyl (S)-3-amino-3-(3,5-dichlorophenyl)propanoate

Intermediate 7

Methyl (R)-3-amino-3-(3,5-dichlorophenyl)propanoate

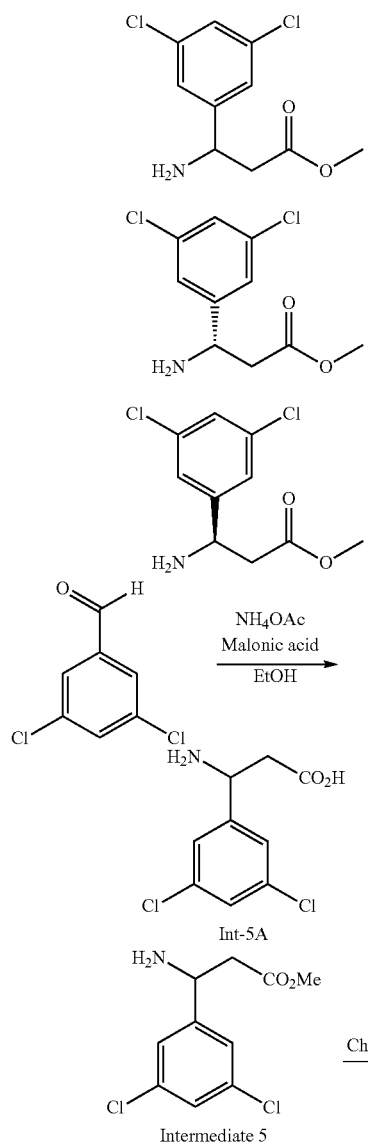

Int-5A: 3-Amino-3-(3,5-dichlorophenyl)propanoic acid: A mixture of ammonium acetate (14.1 g, 183 mmol), 3,5-dichlorobenzaldehyde (8.0 g, 45.7 mmol) and malonic acid (5.23 g, 50.3 mmol) in EtOH (90 mL) was heated at reflux for 16 h. After cooling to room temperature, the solid was collected by filtration, washed with EtOH (15 mL), and dried under vacuum to give crude Int-5A (7.0 g, 66%) as a white solid. LCMS (ES): m/z 234.3 [M+H]$^+$.

Intermediate 5: To a mixture of Int-5A (7.0 g, 29.9 mmol) in MeOH (50 mL) was added SOCl$_2$ (5.02 mL, 68.8 mmol). After stirring at room temperature for 6 h, the solid was removed by filtration. The filtrate was concentrated in vacuo to give a crude product which was dissolved in EtOAc (150 mL). The organic layer was washed with sat. NaHCO$_3$ solution, brine, dried (MgSO$_4$), filtered, and concentrated under reduced pressure to afford the crude product which was purified by flash chromatography (silica gel, CH$_2$Cl$_2$:MeOH, 100:0 to 95:5) to afford Intermediate 5 (3.3 g, 46%) as a yellow oil: $^1$H NMR (500 MHz, CDCl$_3$) δ 7.31 (d, J=1.9 Hz, 2H), 7.28 (t, J=1.9 Hz, 1H), 4.44 (t, J=6.7 Hz, 1H), 3.69 (s, 3H), 2.81-2.63 (m, 2H). LCMS (ES): m/z 248.3 [M+H]$^+$.

Intermediate 6: Intermediate 5 (3.3 g) was purified by preparative chiral SFC (Column: Chiralpak AD, 30×250 mm, 5 micron, BPR Pressure: 150 bars, Temperature: 40° C., Flow rate: 80 mL/min, Mobile Phase: CO$_2$/MeOH (95/5)+0.1% DEA, Detector wavelength: 220 nm) to afford Intermediate 6 (2.3 g) as a yellow oil. $^1$H NMR (500 MHz, CDCl$_3$) δ 7.28 (d, J=1.9 Hz, 1H), 7.26 (t, J=1.9 Hz, 1H), 4.43-4.34 (m, 1H), 3.70 (s, 3H), 2.76-2.56 (m, 2H).

Intermediate 7: Intermediate 5 (3.3 g) was purified by preparative chiral SFC (Column: Chiralpak AD, 30×250 mm, 5 micron, BPR Pressure: 150 bars, Temperature: 40° C., Flow rate: 80 mL/min, Mobile Phase: CO$_2$/MeOH (95/5)+0.1% DEA, Detector wavelength: 220 nm) to afford Intermediate 7 (1.31 g) as a yellow oil. $^1$H NMR (500 MHz, CDCl$_3$) δ 7.27 (d, J=1.9 Hz, 1H), 7.26 (t, J=1.9 Hz, 1H), 4.38 (dd, J=8.7, 4.8 Hz, 1H), 3.70 (s, 3H), 2.65 (dd, J=16.0, 4.8 Hz, 1H), 2.60 (dd, J=16.0, 8.7 Hz, 1H).

Intermediate 8

(S)-Ethyl 3-amino-3-(2,3-dihydrobenzofuran-6-yl)propanoate

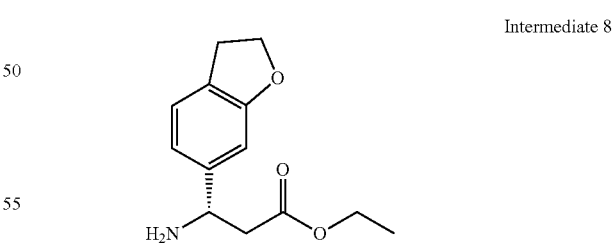

Intermediate 8 was prepared according to the procedure described for Intermediate 1. $^1$H NMR (400 MHz, DMSO-d$_6$) δ 7.17-7.10 (m, 1H), 6.86-6.74 (m, 2H), 4.49 (t, J 8.8 Hz, 2H), 4.19 (t, J=7.0 Hz, 1H), 4.06-3.94 (m, 2H), 3.12 (t, J=8.8 Hz, 2H), 2.70-2.54 (m, 3H), 1.21-1.05 (m, 3H). $^{13}$C NMR (400 MHz, DMSO-d$_6$) δ 171.13, 159.75, 146.24, 125.43, 124.37, 118.21, 106.80, 70.80, 59.62, 52.61, 44.12, 28.79, 14.02. LCMS (ES): m/z 236.0 [M+H]$^+$. $[α]_D^{25\ C}$ 6.0° (c 0.10 in CHCl$_3$).

Intermediate 9

Ethyl (S)-3-amino-3-(2-methoxypyrimidin-5-yl)propanoate

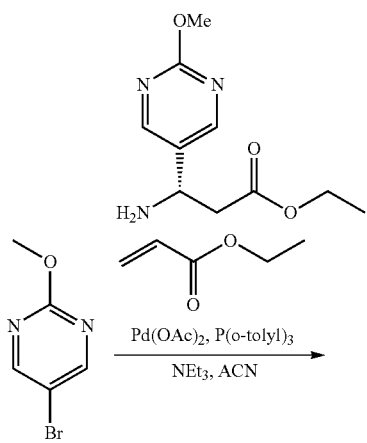

Intermediate 9

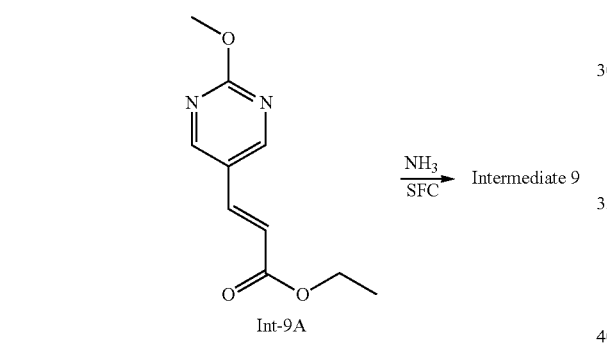

Int-9A

Int-9A was prepared according to the procedure described in Int-1A. $^1$H NMR (400 MHz, CDCl$_3$) δ 8.68 (s, 2H), 7.58 (d, J=16.0 Hz, 1H), 6.46 (d, J=16.0 Hz, 1H), 4.28 (q, J=7.0 Hz, 2H), 4.06 (s, 3H), 1.35 (t, J=7.0 Hz, 3H). LCMS (ES): m/z 209.0 [M+H]$^+$.

Intermediate 9: tert-Butyl alcohol (300 mL) was purged with ammonia keeping the temperature between 0-20° C. for 1 h. The ammonia purged tert-butyl alcohol and Int-9A (20 g, 96 mmol) were added to an 1 L autoclave. The reaction was heated at 80° C. for 30 h. The reaction was cooled to room temperature. The reaction mixture was removed from autoclave and concentrated. The crude solid was triturated with the diethyl ether and filtered. The filtrate was concentrated and purified by ISCO (5% methanol in chloroform) to yield racemate compound (5.9 g). The racemate was further purified by SFC (Chiralpak IA (250×4.6) mm, 5u; % CO$_2$: 80%; % Co solvent: 20%(0.2% DEA in Methanol); Total Flow: 120.0 g/min; Back Pressure: 100 bars; Temperature: 30° C.; Detection: UV at 220 nm) to yield Intermediate 9 (2.3 g, 10%) as the first eluting isomer. $^1$H NMR (300 MHz, DMSO-d$_6$) δ 8.58 (s, 2H), 4.20 (t, J=7.2 Hz, 1H), 4.02 (q, J=6.9 Hz, 2H), 3.89 (s, 3H), 2.67 (dd, J=7.2, 4.9 Hz, 2H), 2.09 (br s, 2H), 1.13 (t, J=7.2 Hz, 3H). LCMS (ES): m/z 226.2 [M+H]$^+$.

Intermediate 10

(S)-Ethyl 3-amino-3-(2-methylpyrimidin-5-yl)propanoate

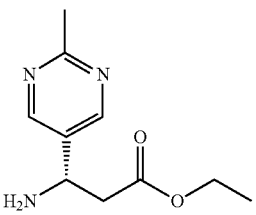

Intermediate 10

Intermediate 10 was prepared according to the procedure described for Intermediate 9. $^1$H NMR (400 MHz, DMSO-d$_6$) δ 8.66 (s, 2H), 4.20 (t, J=7.3 Hz, 1H), 4.05-3.98 (m, 2H), 2.68 (dd, J=7.0, 5.0 Hz, 2H), 2.57 (s, 3H), 2.09 (br s, 2H), 1.15-1.09 (m, 3H). LCMS (ES): m/z 210.2 [M+H]$^+$.

Intermediate 11

(S)-Ethyl 3-amino-3-(pyrimidin-5-yl)propanoate

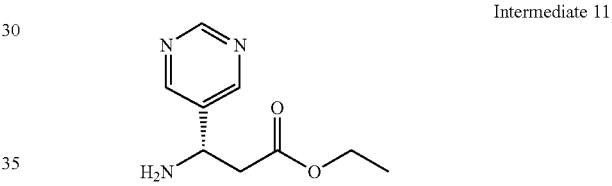

Intermediate 11

Intermediate 11 was prepared according to the procedure described for Intermediate 9. $^1$H NMR (300 MHz, DMSO-d$_6$) δ 9.05 (s, 1H), 8.80 (s, 2H), 4.24 (t, J=7.20 Hz, 1H), 4.01 (q, J=6.90 Hz, 2H), 2.74 (q, J=3.90 Hz, 2H), 1.11 (t, J=6.90 Hz, 3H). LCMS (ES): m/z 196.2 [M+H]$^+$.

Intermediate 12

(±)-Ethyl 3-amino-3-(2-methylpyrimidin-5-yl)propanoate

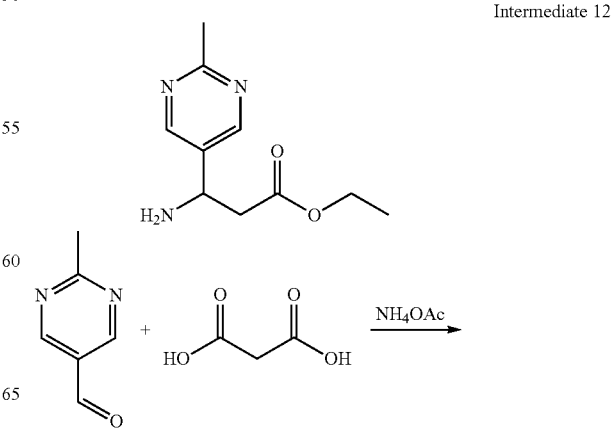

Intermediate 12

-continued

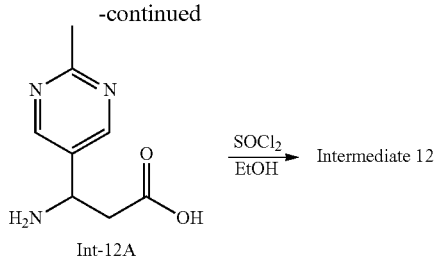

Int-12A

Int-12A. 3-Amino-3-(2-methylpyrimidin-5-yl)propanoic acid: A mixture of commercially available 2-methylpyrimidine-5-carbaldehyde (1.00 g, 8.19 mmol), malonic acid (1.28 g, 12.3 mmol) and NH$_4$OAc (1.58 g, 20.5 mmol) in EtOH (6.55 mL) was heated to 80° C. for 4 h. After cooling to room temperature, the precipitate was collected by filtration, washed with cold EtOH and dried under vacuum to yield Int-12A (1.08 g, 73%) as an off-white solid which was used in the next step without further purification. $^1$H NMR (500 MHz, D$_2$O) δ 8.79 (s, 2H), 4.75-4.73 (m, 1H), 3.01-2.92 (m, 1H), 2.90-2.82 (m, 1H), 2.70 (s, 3H). HPLC retention time (Method #2): 0.168 min.; LCMS (ES): m/z 182.1 [M+H]$^+$.

Intermediate 12: SOCl$_2$ (0.185 mL, 2.54 mmol) was added dropwise to a room temperature solution of Int-12A (0.200 g, 1.10 mmol) in EtOH (2.90 mL). After stirring at room temperature overnight, the solvent was removed in vacuo and the residue was dissolved in DCM, washed with sat. NaHCO$_3$, water and brine. The organic layer was dried over anhydrous Na$_2$SO$_4$ and concentrated in vacuo. The residue was purified by flash chromatography (silica gel, DCM:MeOH, 100:0 to 90:10) to yield Intermediate 12 (0.115 g, 50%) as a light yellow oil. $^1$H NMR (500 MHz, CDCl$_3$) δ 8.68 (s, 2H), 4.47 (dd, J=8.0, 5.5 Hz, 1H), 4.16 (q, J=7.2 Hz, 2H), 2.79-2.58 (m, 5H), 1.25 (t, J=7.2 Hz, 3H). HPLC retention time (Method #2): 0.317 min.; LCMS (ES): m/z 210.1 [M+H]$^+$.

Intermediate 13

(±)-Ethyl 3-amino-3-(2-methoxypyrimidin-5-yl)propanoate

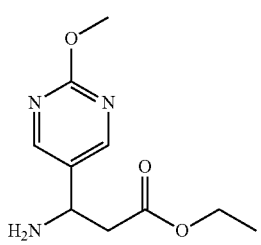

Intermediate 13

Intermediate 13 was prepared using the procedure described for Intermediate 12. $^1$H NMR (500 MHz, CDCl$_3$) δ 8.54 (s, 2H), 4.46-4.39 (m, 1H), 4.16 (q, J=7.2 Hz, 2H), 4.01 (d, J=0.6 Hz, 3H), 2.75-2.60 (m, 2H), 1.25 (t, J=7.2 Hz, 3H). HPLC retention time (Method #2): 0.490 min.; LCMS (ES): m/z 226.1 [M+H]$^+$.

Intermediate 14

(±)-Ethyl 3-amino-3-(pyrimidin-5-yl)propanoate

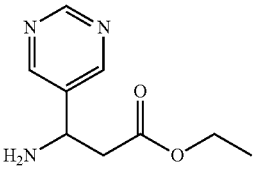

Intermediate 14

Intermediate 14 was prepared using the procedure described for Intermediate 12. $^1$H NMR (500 MHz, CDCl$_3$) δ 9.15 (s, 1H), 8.79 (s, 2H), 4.50 (dd, J=7.8, 5.6 Hz, 1H), 4.16 (q, J=7.2 Hz, 2H), 2.77-2.64 (m, 2H), 1.25 (t, J=7.2 Hz, 3H). HPLC retention time (Method #2): 0.318 min.; LCMS (ES): m/z 196.1 [M+H]$^+$ Intermediate 15

(S)-Ethyl 3-amino-3-(quinolin-3-yl)propanoate

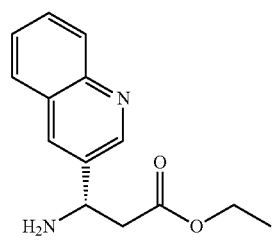

Intermediate 15

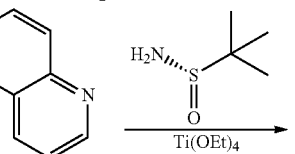

Int-15A

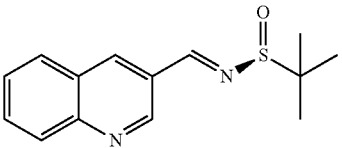

Int-15B

Int-15A. (S,E)-2-Methyl-N-(quinolin-3-ylmethylene)propane-2-sulfinamide: To a solution of quinoline-3-carbaldehyde (25.0 g, 159 mmol) in DCM (700 mL) was added (S)-2-methylpropane-2-sulfinamide (19.3 g, 159 mmol) followed by Ti(OEt)$_4$ (167 mL, 795 mmol). The reaction was heated to 40° C. overnight. The reaction was cooled to room temperature and quenched with water. The solids were filtered through a CELITE® pad and washed with DCM. The organic layer was washed with water, brine, dried over Na$_2$SO$_4$, and concentrated in vacuo. The crude product was purified by flash chromatography to yield Int-15A (40 g, 97%) as a yellow solid. $^1$H NMR (400 MHz, CDCl$_3$) δ 9.45 (d, J=2.0 Hz, 1H), 8.83 (s, 1H), 8.54 (d, J=1.8 Hz, 1H), 8.19 (d, J=8.5 Hz, 1H), 7.96 (d, J=8.3 Hz, 1H), 7.83-7.86 (m, 1H), 7.63-7.67 (m, 1H), 1.34 (s, 9H).

Int-15B. (S)-Ethyl 3-((S)-1,1-dimethylethylsulfinamido)-3-(quinolin-3-yl)propanoate: To a solution of 1 N NaHMDS in THF (230 mL, 230 mmol) in THF (750 mL) at −78° C. was added ethyl acetate (22.56 mL, 230 mmol) dropwise. The reaction was stirred for 0.5 h and Int-15A (40 g, 154 mmol) in THF (500 mL) was added dropwise. The reaction was stirred for 1 h at −78° C. and quenched with saturated NH$_4$Cl solution. The mixture was extracted with ethyl acetate. The organic layer was washed with water, brine, dried over sodium sulfate and concentrated. The crude was purified by flash chromatography (2-3% methanol in DCM) to afford Int-15B (50 g, 93%) as a pale yellow liquid. $^1$H NMR (300 MHz, DMSO-d$_6$) δ 8.91-9.02 (m, 1H), 8.38-8.25 (m, 1H), 7.93-8.03 (m, 2H), 7.74-7.77 (m, 1H), 7.58-7.63 (m, 1H), 4.92-4.80 (m, 1H), 4.10-3.92 (m, 2H), 3.06-2.89 (m, 2H), 1.18-1.01 (m, 12H). LCMS (ES): m/z 349.0 [M+H]$^+$.

Intermediate 15: To a solution of Int-15B (50 g, 143 mmol) in ethanol (500 ml) was added 4 M HCl in 1,4-dioxane (200 mL). The reaction was stirred at rt for 2 h. The solvent was removed under reduced pressure. The residue was dissolved in water (150 mL) and washed with MTBE (3×75 mL). The aqueous layer was basified with 10% NaHCO$_3$ solution and extracted with ethyl acetate (3×150 mL). The combined organic layers were washed with water, brine, dried over Na$_2$SO$_4$ and concentrated. The crude was purified by SFC (Whelk (RR) (250×30) mm, 5u; % CO$_2$: 70%; % Co solvent: 30%(0.2% DEA in methanol); Total Flow: 130.0 g/min; Back Pressure: 100 bars; Temperature: 30° C.; Detection: UV at 226 nm) to yield Intermediate 15 (15 g, 43%) as a brown liquid. $^1$H NMR (400 MHz, DMSO-d$_6$) δ 8.94 (d, J=2.6 Hz, 1H), 8.27 (d, J=2.0 Hz, 1H), 7.92-8.02 (m, 2H), 7.74-7.69 (m, 1H), 7.56-7.60 (m, 1H), 4.44 (t, J=7.4 Hz, 1H), 4.05-3.97 (m, 2H), 2.76 (d, J=6.6 Hz, 2H), 2.17 (br. s., 2H), 1.09 (t, J=7.3 Hz, 3H). LCMS (ES): m/z 245.2 [M+H]$^+$. 99.3% ee.

Intermediate 16

(±)-Ethyl 3-amino-3-(quinoxalin-2-yl)propanoate

Intermediate 16

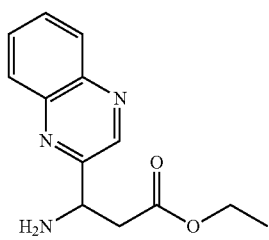

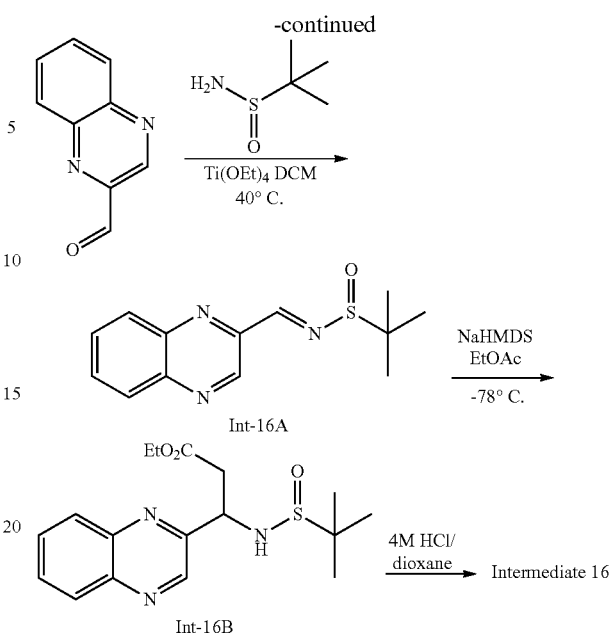

Int-16A. (E)-2-Methyl-N-(quinoxalin-2-ylmethylene)propane-2-sulfinamide. To a solution of commercially available quinoxaline-2-carbaldehyde (0.500 g, 3.16 mmol) in DCM (14.0 mL) were added 2-methylpropane-2-sulfinamide (0.383 g, 3.16 mmol) and Ti(OEt)$_4$ (3.31 mL, 15.8 mmol). The reaction mixture was refluxed for 17 h, cooled to room temperature and quenched with water. The solids were filtered through a CELITE® pad and washed with DCM. The organic phase was separated and washed with water, brine, dried over anhydrous Na$_2$SO$_4$ and concentrated in vacuo. The residue was purified by flash chromatography (silica gel, hexanes:EtOAc, 100:0 to 50:50) to yield Int-16A (0.690 g, 84%) as a tan solid. $^1$H NMR (500 MHz, DMSO-d$_6$) δ 9.54 (s, 1H), 8.68 (s, 1H), 8.29-8.17 (m, 2H), 8.06-7.92 (m, 2H), 1.27 (s, 9H). HPLC retention time (Method #2): 2.132 min.; LCMS (ES): m/z 262.2 [M+H]$^+$.

Int-16B. Ethyl 3-((tert-butylsulfinyl)amino)-3-(quinoxalin-2-yl)propanoate. Int-16B was prepared using the procedure described for Int-15B. $^1$H NMR (500 MHz, DMSO-d$_6$) δ 9.23 (s, 1H), 8.07-8.14 (m, 1H), 7.99-8.07 (m, 1H), 7.82-7.91 (m, 2H), 6.17 (d, J=9.35 Hz, 1H), 4.97-5.14 (m, 1H), 4.05 (quin, J=6.81 Hz, 2H), 3.10-3.26 (m, 1H), 2.94 (dd, J=8.80, 15.68 Hz, 1H), 1.10-1.19 (m, 12H). HPLC retention time (Method #2): 1.935 min.; LCMS (ES): m/z 350.1 [M+H]$^+$.

Intermediate 16: To a room temperature solution of Int-16B (0.111 g, 0.318 mmol) in EtOH (1.11 mL) was added 4M HCl in Dioxane (0.443 mL). After stirring at room temperature for 1.5 h, the solvent was removed in vacuo. The residue was dissolved in water and washed with diethyl ether (3×). The aqueous layer was basified using 10% aq. NaHCO$_3$ and then extracted with EtOAc (3×). The combined organic layers were washed with water, brine, dried over anhydrous Na$_2$SO$_4$ and concentrated in vacuo to yield Intermediate 16 (59.3 mg, 76%) as a tan oil which was not purified further. $^1$H NMR (400 MHz, CD$_3$OD) δ 8.99 (s, 1H), 8.16-8.00 (m, 2H), 7.90-7.74 (m, 2H), 4.66 (t, J=6.8 Hz, 1H), 4.08 (q, J=7.2 Hz, 2H), 3.14-3.03 (m, 1H), 2.98-2.87 (m, 1H), 1.15 (t, J=7.2 Hz, 3H). HPLC retention time (Method #2): 0.983 min.; LCMS (ES): m/z 246.2 [M+H]$^+$.

Intermediate 17

Ethyl (S)-3-amino-2-(((benzyloxy)carbonyl)amino)propanoate, HCl

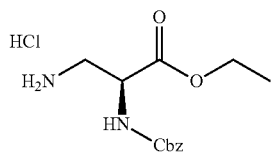

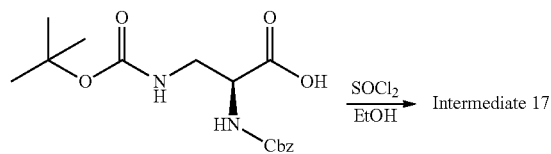

Intermediate 17. Intermediate 17 was prepared using the procedure described in Patent: WO 2000021932. $^1$H NMR (500 MHz, DMSO-$d_6$) δ 8.16 (br. s., 3H), 7.88 (d, J=8.3 Hz, 1H), 7.43-7.26 (m, 5H), 5.08 (s, 2H), 4.38 (td, J=8.7, 4.7 Hz, 1H), 4.13 (q, J=7.2 Hz, 2H), 3.22 (dd, J=12.9, 4.4 Hz, 1H), 3.05 (dd, J=12.8, 9.5 Hz, 1H), 1.18 (t, J=7.2 Hz, 3H). HPLC retention time (Method #2): 1.078 min.; LCMS (ES): m/z 267 [M+H]$^+$.

Intermediate 18

Ethyl (S)-3-amino-2-((2,4,6-trimethylphenyl)sulfonamido)propanoate

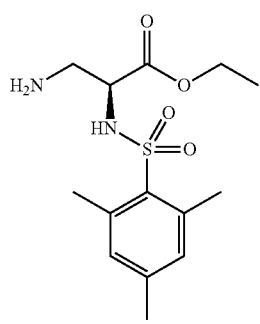

Intermediate 18 was prepared using the procedure described in: Pitts, J. W. et. al., *J. Med. Chem.* 2000 43, 27. $^1$H NMR (500 MHz, CDCl$_3$) δ 6.95 (s, 2H), 5.63 (br. s., 1H), 5.31 (s, 1H), 3.97-4.05 (m, 2H), 3.82 (t, J=4.68 Hz, 1H), 2.94-3.05 (m, 2H), 2.66 (s, 6H), 2.29 (s, 3H), 1.14 (t, J=7.15 Hz, 3H). LCMS (ES): m/z 315 [M+H]$^+$.

Intermediate 19

(E)-4-(2-(1,8-Naphthyridin-2-yl)vinyl)-1H-pyrrole-2-carboxylic acid, HCl

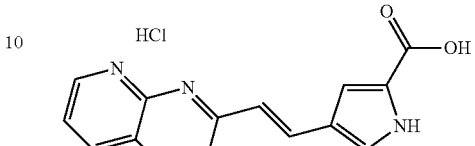

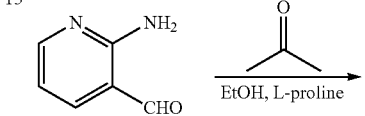

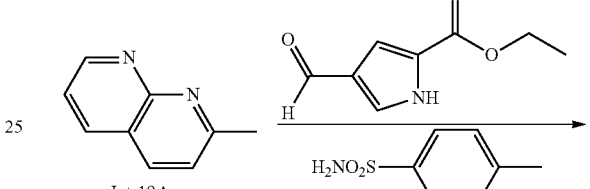

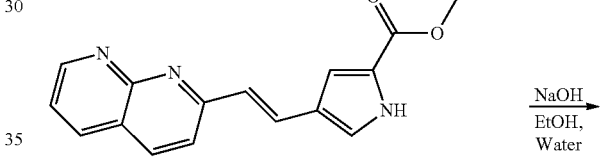

Int-19A. 2-Methyl-1,8-naphthyridine: Int-19A was prepared using the procedure described in Patent: WO 2011150156. $^1$H NMR (500 MHz, DMSO-$d_6$) δ 9.02 (dd, J=4.3, 2.1 Hz, 1H), 8.40 (dd, J=8.0, 1.9 Hz, 1H), 8.34 (d, J=8.3 Hz, 1H), 7.56 (dd, J=8.1, 4.3 Hz, 1H), 7.51 (s, 1H), 2.70 (s, 3H). HPLC retention time (Method #1): 0.303 min.; LCMS (ES): m/z 145.0 [M+H]$^+$.

Int-19B. Ethyl (E)-4-(2-(1,8-naphthyridin-2-yl)vinyl)-1H-pyrrole-2-carboxylate: A solution of Int-19A (0.300 g, 2.08 mmol), commercially available ethyl 4-formyl-1H-pyrrole-2-carboxylate (0.348 g, 2.08 mmol), and 4-methylbenzenesulfonamide (0.356 g, 2.08 mmol) in toluene (4.5 mL) was stirred at reflux for 21 h. After cooling to room temperature, the precipitate was collected by filtration, triturated with DCM (2×) and dried under vacuum to yield Int-19B (0.519 g, 94%) as a yellow solid which was used in the next step without further purification. $^1$H NMR (500 MHz, DMSO-$d_6$) δ 12.14 (br. s., 1H), 9.01 (dd, J=4.3, 2.1 Hz, 1H), 8.41-8.28 (m, 2H), 7.82 (d, J=16.2 Hz, 1H), 7.76 (d, J=8.5 Hz, 1H), 7.52 (dd, J=8.0, 4.1 Hz, 1H), 7.46 (s, 1H), 7.24-7.16 (m, 2H), 4.27 (q, J=7.2 Hz, 2H), 1.31 (t, J=7.0 Hz, 3H). HPLC retention time (Method #1): 1.973 min.; LCMS (ES): m/z 294.0 [M+H]$^+$.

Intermediate 19: A 95:5 EtOH/H$_2$O solution (421 mL) containing Int-19B (35.0 g, 95.0 mmol) and NaOH (11.5 g, 286 mmol) was refluxed for 4 h. After cooling to room temperature, the EtOH was removed in vacuo and the residue was acidified to pH~2 with 1M aq. HCl. The precipitate was collected by filtration, washed with water and dried under vacuum to yield Intermediate 19 (14.2 g, 39%) as a crude orange solid. ¹H NMR (500 MHz, DMSO-d₆) δ 12.31 (br. s., 1H), 9.16 (dd, J=4.8, 1.8 Hz, 1H), 8.80 (d, J=8.0 Hz, 1H), 8.75 (d, J=8.8 Hz, 1H), 8.22-8.08 (m, 2H), 7.85 (dd, J=8.0, 4.7 Hz, 1H), 7.53 (dd, J=2.6, 1.5 Hz, 1H), 7.33 (d, J=16.0 Hz, 1H), 7.18 (s, 1H). HPLC retention time (Method #1): 1.402 min.; LCMS (ES): m/z 266.0 [M+H]⁺.

Alternate Preparation of Intermediate 19

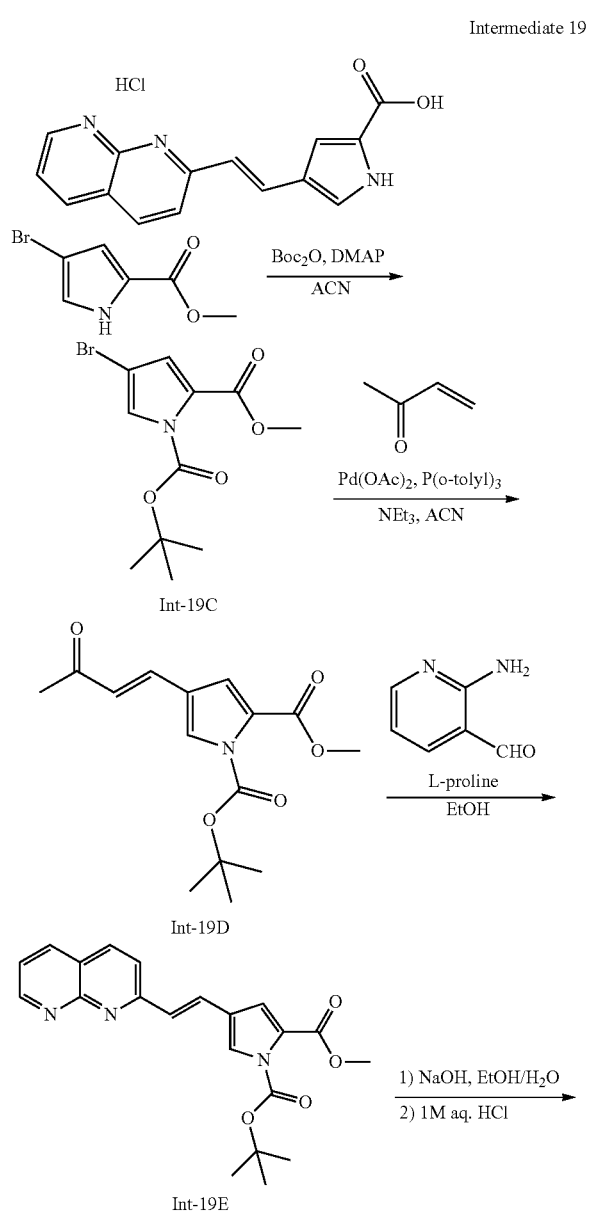

Int-19C. 1-(Tert-butyl) 4-bromo-1H-pyrrole-1,2-dicarboxylate: Int-19C was prepared using the procedure described in: Desplat, V. et. al. *Journal of Enzyme Inhibition and Medicinal Chemistry* 2010, 25, 204. ¹H NMR (500 MHz, CDCl₃) δ 7.31 (d, J=1.9 Hz, 1H), 6.79 (d, J=1.9 Hz, 1H), 3.85 (s, 3H), 1.58 (s, 9H). LCMS (ES): m/z 249.9 [M−tBu+H]⁺.

Int-19D. 1-(Tert-butyl) 2-methyl (E)-4-(3-oxobut-1-en-1-yl)-1H-pyrrole-1,2-dicarboxylate: Int-19D was prepared using the procedure described for Int-1A. ¹H NMR (500 MHz, CDCl₃) δ 7.53 (d, J=1.9 Hz, 1H), 7.36 (d, J=16.0 Hz, 1H), 7.01 (d, J=1.9 Hz, 1H), 6.48 (d, J=16.2 Hz, 1H), 3.88 (s, 3H), 2.33 (s, 3H), 1.60 (s, 9H). HPLC retention time (Method #1): 3.193 min.; LCMS (ES): m/z 294.1 [M+H]⁺.

Int-19E. 1-(Tert-butyl) 2-methyl (E)-4-(2-(1,8-naphthyridin-2-yl)vinyl)-1H-pyrrole-1,2-dicarboxylate, TFA: A solution of Int-19D (36 mg, 0.123 mmol), 2-aminonicotinaldehyde (19.5 mg, 0.160 mmol) and L-proline (4.58 mg, 0.115 mmol) in EtOH (0.366 mL) was stirred at 80° C. for 19 h. After cooling to room temperature, the solvent was removed in vacuo and the residue was purified by Prep. HPLC (Phenomenex Luna AXIA 5u C18 21.1×100 mm, 10 min gradient, 15 min run, 10% to 100% Solvent B=90% MeOH-10% H₂O-0.1% TFA, Solvent A=10% MeOH-90% H₂O-0.1% TFA) to yield Int-9E (11.3 mg, 19%) as an orange oil. LCMS (ES): m/z 280.0 [M−Boc+H]⁺.

Intermediate 19. A solution of Int-19E (11.3 mg, 0.023 mmol) and NaOH (4.58 mg, 0.115 mmol) in EtOH (0.177 mL) and water (9.32 µL) was refluxed for 4 h. After cooling to room temperature, the EtOH was removed in vacuo and the residue was acidified to pH with 1M aq. HCl. The precipitate was collected by filtration, washed with water and dried under vacuum to yield Intermediate 19 (6.9 mg, 100%) as a crude orange solid. LCMS (ES): m/z 266.0 [M+H]⁺.

Intermediate 20

(E)-4-(2-(1,8-Naphthyridin-2-yl)vinyl)-5-methyl-1H-pyrrole-2-carboxylic acid, HCl

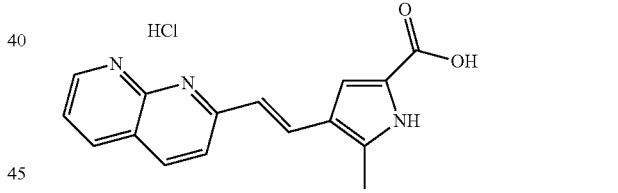

Intermediate 20 was prepared using the procedure described for Intermediate 19 starting from Ethyl 4-formyl-5-methyl-1H-pyrrole-2-carboxylate which was prepared according to the procedure described in Patent: WO 2005026149. LCMS (ES): m/z 280.1 [M+H]⁺.

Intermediate 21

4-(1,8-Naphthyridin-2-yl)-1H-pyrrole-2-carboxylic acid, HCl

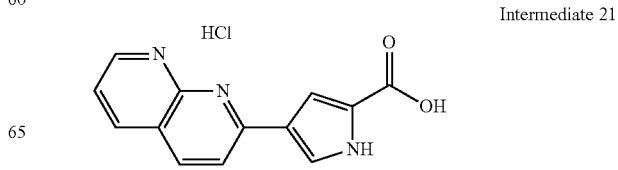

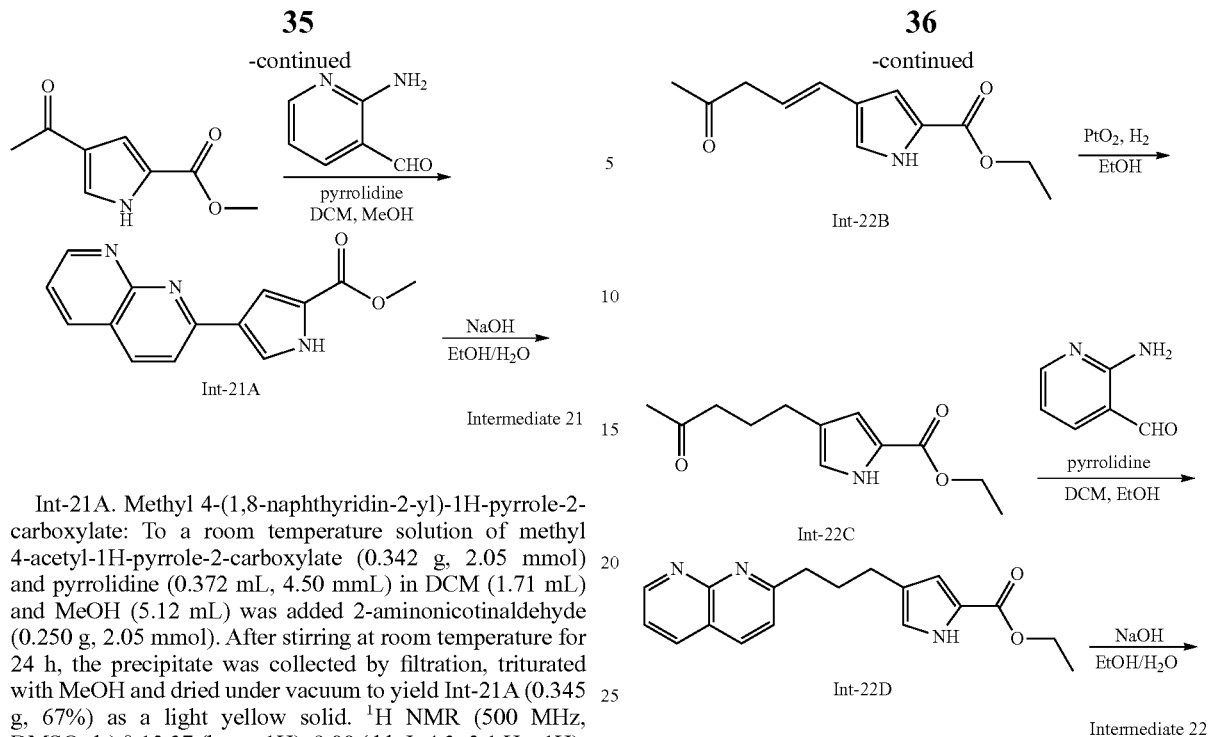

Int-21A. Methyl 4-(1,8-naphthyridin-2-yl)-1H-pyrrole-2-carboxylate: To a room temperature solution of methyl 4-acetyl-1H-pyrrole-2-carboxylate (0.342 g, 2.05 mmol) and pyrrolidine (0.372 mL, 4.50 mmL) in DCM (1.71 mL) and MeOH (5.12 mL) was added 2-aminonicotinaldehyde (0.250 g, 2.05 mmol). After stirring at room temperature for 24 h, the precipitate was collected by filtration, triturated with MeOH and dried under vacuum to yield Int-21A (0.345 g, 67%) as a light yellow solid. $^1$H NMR (500 MHz, DMSO-$d_6$) δ 12.37 (br. s., 1H), 9.00 (dd, J=4.3, 2.1 Hz, 1H), 8.44-8.30 (m, 2H), 8.05 (d, J=8.5 Hz, 1H), 7.93 (d, J=1.7 Hz, 1H), 7.57 (d, J=1.7 Hz, 1H), 7.52 (dd, J=8.0, 4.1 Hz, 1H), 3.83 (s, 3H). HPLC retention time (Method #1): 1.515 min.; LCMS (ES): m/z 254.1 $[M+H]^+$.

Intermediate 21. Intermediate 21 was prepared using the procedure described for Intermediate 19. $^1$H NMR (500 MHz, DMSO-$d_6$) δ 12.62 (br. s., 1H), 9.17 (dd, J=5.0, 1.7 Hz, 1H), 8.91-8.81 (m, 1H), 8.72 (d, J=8.8 Hz, 1H), 8.37 (d, J=8.5 Hz, 1H), 8.23-8.13 (m, 1H), 7.88 (dd, J=8.1, 5.1 Hz, 1H), 7.66 (t, J=1.9 Hz, 1H). HPLC retention time (Method #1): 1.205 min.; LCMS (ES): m/z 240.1 $[M+H]^+$.

Intermediate 22

4-(3-(1,8-Naphthyridin-2-yl)propyl)-1H-pyrrole-2-carboxylic acid, HCl, 3 NaCl

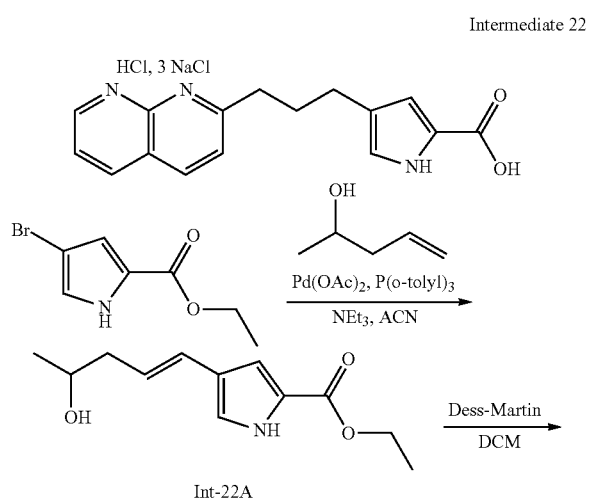

Int-22A. Ethyl (E)-4-(4-hydroxypent-1-en-1-yl)-1H-pyrrole-2-carboxylate: Int-22A was prepared using the procedure described for Int-1A. $^1$H NMR (500 MHz, CDCl$_3$) δ 8.99 (br. s., 1H), 6.99 (s, 1H), 6.91-6.87 (m, 1H), 6.34 (d, J=16.0 Hz, 1H), 6.01-5.90 (m, 1H), 4.36-4.28 (m, 2H), 3.89 (dd, J=12.2, 6.2 Hz, 1H), 2.40-2.32 (m, 1H), 2.30-2.19 (m, 1H), 1.41-1.32 (m, 3H), 1.25 (d, J=6.3 Hz, 3H). HPLC retention time (Method #2): 1.568 min.; LCMS (ES): m/z 224.2 $[M+H]^+$.

Int-22B. Ethyl (E)-4-(4-oxopent-1-en-1-yl)-1H-pyrrole-2-carboxylate: Dess-Martin periodinane (0.456 g, 1.08 mmol) was added to a solution of Int-22A (0.200 g, 0.896 mmol) in DCM (8.37 mL). After stirring at room temperature for 1 h, the reaction was diluted with diethyl ether and filtered through a CELITE® pad. The filtrate was concentrated in vacuo and the residue was purified by flash chromatography (silica gel, hexanes:EtOAc, 100:0 to 70:30) to yield Int-22B (106 mg, 53%) as a yellow oil. $^1$H NMR (500 MHz, CDCl$_3$) δ 8.93 (br. s., 1H), 6.90-6.88 (m, 1H), 6.81 (dd, J=2.8, 1.7 Hz, 1H), 6.23 (d, J=16.0 Hz, 1H), 5.92 (dt, J=15.7, 7.2 Hz, 1H), 4.22 (q, J=7.2 Hz, 2H), 3.16 (d, J=7.2 Hz, 2H), 2.09 (s, 3H), 1.26 (t, J=7.2 Hz, 3H). HPLC retention time (Method #2): 0.703 min.; 1.733 min LCMS (ES): m/z 222.2 $[M+H]^+$.

Int-22C. Ethyl 4-(4-oxopentyl)-1H-pyrrole-2-carboxylate: To a solution of Int-22B (95 mg, 0.185 mmol) in EtOH (6.33 mL) was added PtO$_2$ (22 mg, 0.095 mmol). The suspension was stirred at room temperature under a H$_2$ atmosphere (1 atm, balloon) for 2 h and then filtered through a CELITE® pad. The filtrate was concentrated in vacuo to yield Int-22C (82 mg, 77%) as a yellow oil which was not purified further. $^1$H NMR (500 MHz, CDCl$_3$) δ 8.91 (br. s., 1H), 6.79-6.68 (m, 2H), 4.31 (q, J=7.1 Hz, 2H), 2.47 (dt, J=17.5, 7.5 Hz, 4H), 2.13 (s, 3H), 1.86 (quin, J=7.4 Hz, 2H), 1.36 (t, J=7.2 Hz, 3H). HPLC retention time (Method #2): 1.788 min.; LCMS (ES): m/z 224.2 $[M+H]^+$.

Int-22D. Ethyl 4-(3-(1,8-naphthyridin-2-yl)propyl)-1H-pyrrole-2-carboxylate: To a solution of Int-22C (82 mg, 0.367 mmol) and pyrrolidine (36 μL, 0.441 mmol) in DCM (0.307 mL) and EtOH (0.921 mL) was added 2-aminonicotinaldehyde (45 mg, 0.367 mmol). After stirring at room temperature for 7 h, the solvent was removed in vacuo and the residue was purified by flash chromatography (silica gel, DCM:EtOAc, 100:0 to 25:75) to yield Int-22D (61.2 mg, 54%) as a white solid. $^1$H NMR (500 MHz, CDCl$_3$) 9.10 (dd, J=4.1, 1.9 Hz, 1H), 8.88 (br. s., 1H), 8.16 (dd, J=8.0, 1.9 Hz, 1H), 8.10 (d, J=8.3 Hz, 1H), 7.45 (dd, J=8.1, 4.3 Hz, 1H), 7.38 (d, J=8.3 Hz, 1H), 6.79 (s, 2H), 4.30 (q, J=7.2 Hz, 2H), 3.18-3.00 (m, 2H), 2.61 (t, J=7.6 Hz, 2H), 2.20 (quin, J=7.6 Hz, 2H), 1.35 (t, J=7.2 Hz, 3H). HPLC retention time (Method #2): 1.140 min.; LCMS (ES): m/z 310.3 [M+H]$^+$.

Intermediate 22: A 95:5 EtOH/H$_2$O solution (1.58 mL) containing Int-22D (61.2 mg, 0.198 mmol) and NaOH (23.7 mg, 0.593 mmol) was refluxed for 2 h. After cooling to room temperature, the EtOH was concentrated in vacuo and the residue was acidified to pH~2 with 1M aq. HCl. The mixture was reconcentrated and the residue was dried under vacuum to yield Intermediate 22 (98 mg, 100%) as a crude orange solid which was not purified further. $^1$H NMR (500 MHz, DMSO-d$_6$) δ 11.43 (br. s., 1H), 9.25 (br. s., 1H), 8.88 (d, J=7.2 Hz, 1H), 8.82 (d, J=8.0 Hz, 1H), 7.93 (d, J=5.8 Hz, 2H), 6.79 (br. s., 1H), 6.59 (br. s., 1H), 3.14 (br. s., 2H), 2.56-2.51 (m, 2H), 2.09 (br. s., 2H). HPLC retention time (Method #2): 0.703 min.; LCMS (ES): m/z 282.2 [M+H]$^+$.

Intermediate 23

Ethyl (S)-3-(7-bromo-1-oxo-3,4-dihydropyrrolo[1,2-a]pyrazin-2(1H)-yl)-3-(3-fluoro-4-methoxyphenyl)propanoate

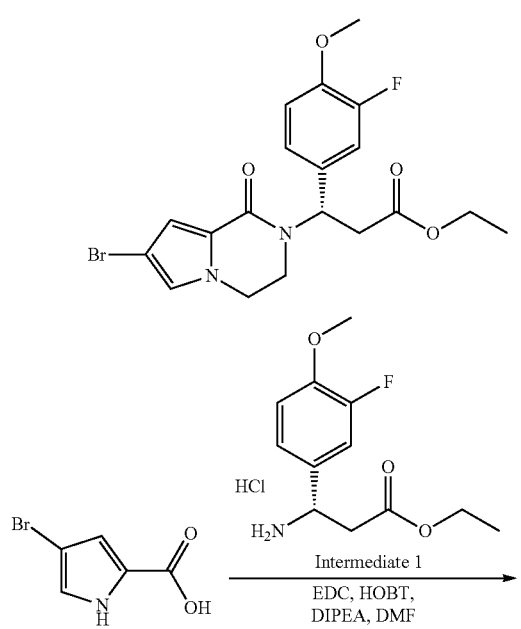

Intermediate 23

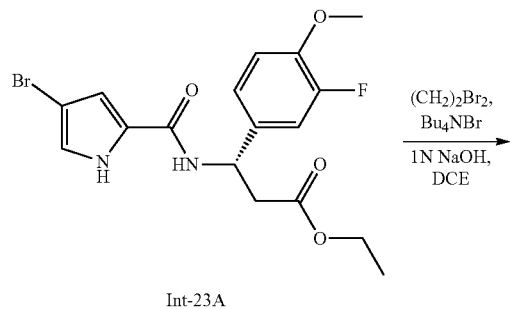

Intermediate 23

Int-23A. Ethyl (S)-3-(4-bromo-1H-pyrrole-2-carboxamido)-3-(3-fluoro-4-methoxyphenyl)propanoate: To a solution of commercially available 4-bromo-1H-pyrrole-2-carboxylic acid (1.00 g, 5.26 mmol) and Intermediate 1 (1.46 g, 5.26 mmol) in DMF (26.3 mL) were added EDC (2.02 g, 10.5 mmol), HOBT (1.61 g, 10.5 mmol) and DIPEA (2.02 mL, 11.6 mmol). After stirring at room temperature for 1.5 h, the reaction was diluted with water and extracted with EtOAc (3×). The combined organic phases were washed with sat. NH$_4$Cl, water, brine, dried over anhydrous Na$_2$SO$_4$, filtered and concentrated in vacuo. The residue was purified by flash chromatography (silica gel, hexanes/EtOAc, 100:0 to 0:100) to yield Int-23A (1.99 g, 91%) as a white gummy solid. $^1$H NMR (500 MHz, CDCl$_3$) δ 9.35 (br. s., 1H), 7.24 (d, J=8.3 Hz, 1H), 7.10-7.01 (m, 2H), 6.94-6.87 (m, 2H), 6.67 (dd, J=2.6, 1.5 Hz, 1H), 5.46 (dt, J=8.5, 5.4 Hz, 1H), 4.18-4.06 (m, 2H), 3.87 (s, 3H), 2.99-2.79 (m, 2H), 1.21 (t, J=7.2 Hz, 3H). HPLC retention time (Method #2): 2.368 min.; LCMS (ES): m/z 413.1, 415.1 [M+H]$^+$.

Intermediate 23: A mixture of Int-23A (1.99 g, 4.82 mmol), NBu$_4$Br (1.55 g, 4.82 mmol), 1,2-dibromoethane (2.08 mL, 24.1 mmol) and 1N aq. NaOH (14.5 mL, 14.5 mmol) in dichloroethane (14.7 mL) was stirred at 50° C. for 1.5 h. After cooling to room temperature, the reaction was diluted with EtOAc then washed with sat. NH$_4$Cl and brine. The organic phase was dried over anhydrous Na$_2$SO$_4$, concentrated in vacuo and the residue purified by flash chromatography (silica gel, hexanes/EtOAc, 100:0 to 50:50) to afford Intermediate 23 (0.818 g, 39%) as a white gummy semi-solid. $^1$H NMR (500 MHz, CDCl$_3$) δ 7.12-7.01 (m, 2H), 6.97-6.89 (m, 2H), 6.68 (d, J=1.7 Hz, 1H), 6.27 (dd, J=9.1, 6.9 Hz, 1H), 4.17-4.09 (m, 2H), 4.03 (ddd, J=12.2, 7.6, 4.1 Hz, 1H), 3.96-3.85 (m, 4H), 3.61-3.51 (m, 1H), 3.33-3.22 (m, 1H), 3.05-2.85 (m, 2H), 1.20 (t, J=7.2 Hz, 3H). HPLC retention time (Method #2): 2.465 min.; LCMS (ES): m/z 439.1, 441.1 [M+H]$^+$.

Intermediate 24

Ethyl (S)-3-(7-bromo-1-oxo-3,4-dihydropyrrolo[1,2-a]pyrazin-2(1H)-yl)-3-(6-methoxypyridin-3-yl)propanoate Intermediate 24

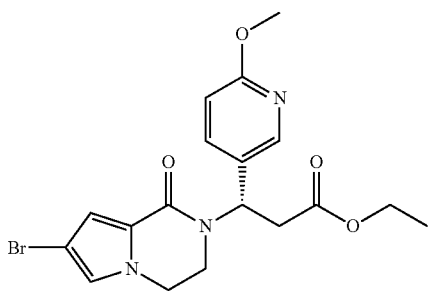

Intermediate 24 was prepared using the procedure described for Intermediate 23. ¹H NMR (500 MHz, CDCl₃) δ 8.12 (d, J=2.5 Hz, 1H), 7.60 (dd, J=8.8, 2.5 Hz, 1H), 6.92 (d, J=1.7 Hz, 1H), 6.74 (d, J=8.8 Hz, 1H), 6.68 (d, J=1.7 Hz, 1H), 6.23 (dd, J=9.2, 7.0 Hz, 1H), 4.13 (dd, J=7.2, 1.7 Hz, 2H), 4.06-4.00 (m, 1H), 3.97-3.88 (m, 4H), 3.61 (ddd, J=12.4, 7.8, 4.3 Hz, 1H), 3.37-3.27 (m, 1H), 3.07-2.98 (m, 2H), 1.21 (t, J=7.0 Hz, 3H). HPLC retention time (Method #2): 1.955 min.; LCMS (ES): m/z 422.2, 424.1 [M+H]⁺.

Intermediate 25

Ethyl (S)-3-(3-fluoro-4-methoxyphenyl)-3-(7-formyl-1-oxo-3,4-dihydropyrrolo[1,2-a]pyrazin-2(1H)-yl)propanoate Intermediate 25

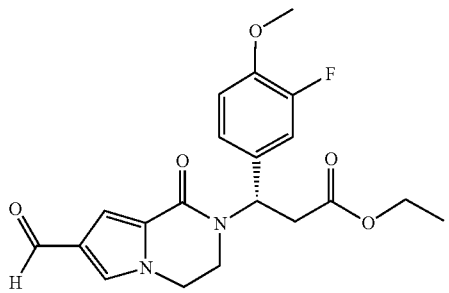

Intermediate 25 was prepared using the procedure described for Intermediate 23 starting from 4-formyl-1H-pyrrole-2-carboxylic acid which was prepared following Patent: WO 2009148004. ¹H NMR (400 MHz, CDCl₃) δ 9.81 (s, 1H), 7.37 (d, J=1.5 Hz, 1H), 7.31 (d, J=1.5 Hz, 1H), 7.15-7.03 (m, 2H), 6.96-6.86 (m, 1H), 6.36-6.18 (m, 1H), 4.24-4.09 (m, 3H), 4.07-3.98 (m, 1H), 3.89 (s, 3H), 3.71-3.57 (m, 1H), 3.39-3.24 (m, 1H), 3.03-2.96 (m, 2H), 1.21 (t, J=7.2 Hz, 3H). HPLC retention time (Method #2): 1.808 min.; LCMS (ES): m/z 389.3 [M+H]⁺.

Example 1

(S)-3-(3-Fluoro-4-methoxyphenyl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid Example 1

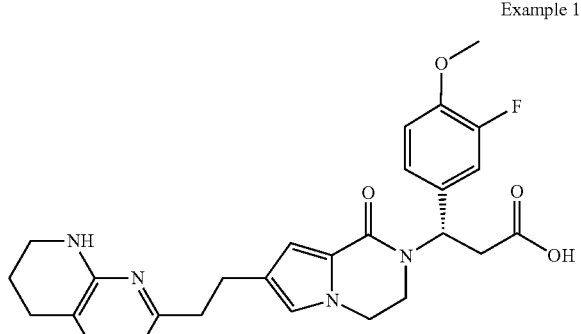

and

Example 2

(3S)-3-(3-Fluoro-4-methoxyphenyl)-3-(1-oxo-7-(2-(1,2,3,4-tetrahydro-1,8-naphthyridin-2-yl)ethyl)-3,4-dihydropyrrolo[1,2-a]pyrazin-2(1H)-yl)propanoic acid Example 2

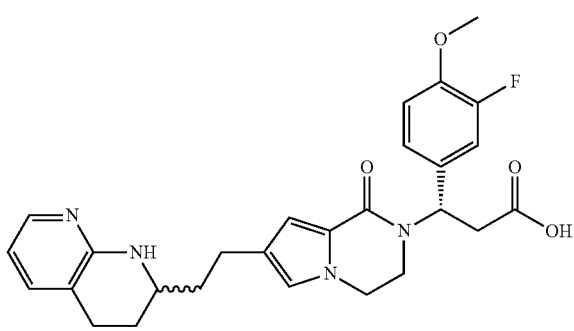

-continued
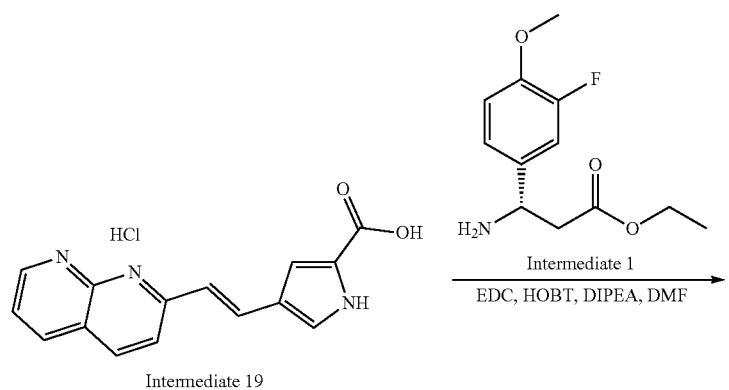
Intermediate 19
EDC, HOBT, DIPEA, DMF
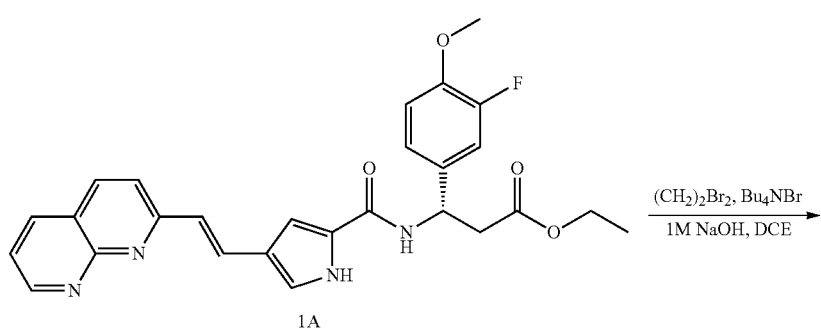
1A
(CH₂)₂Br₂, Bu₄NBr
1M NaOH, DCE
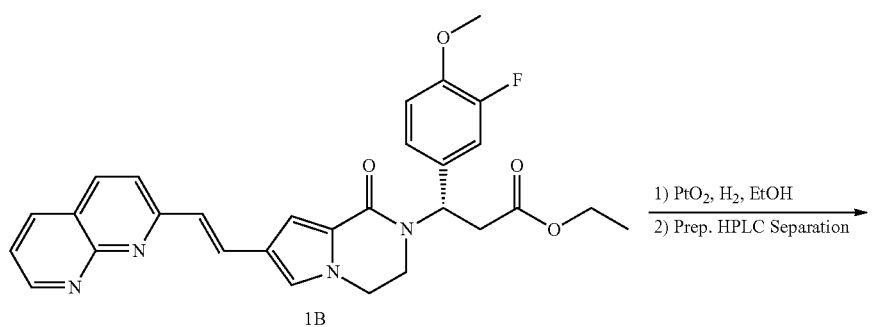
1B
1) PtO₂, H₂, EtOH
2) Prep. HPLC Separation
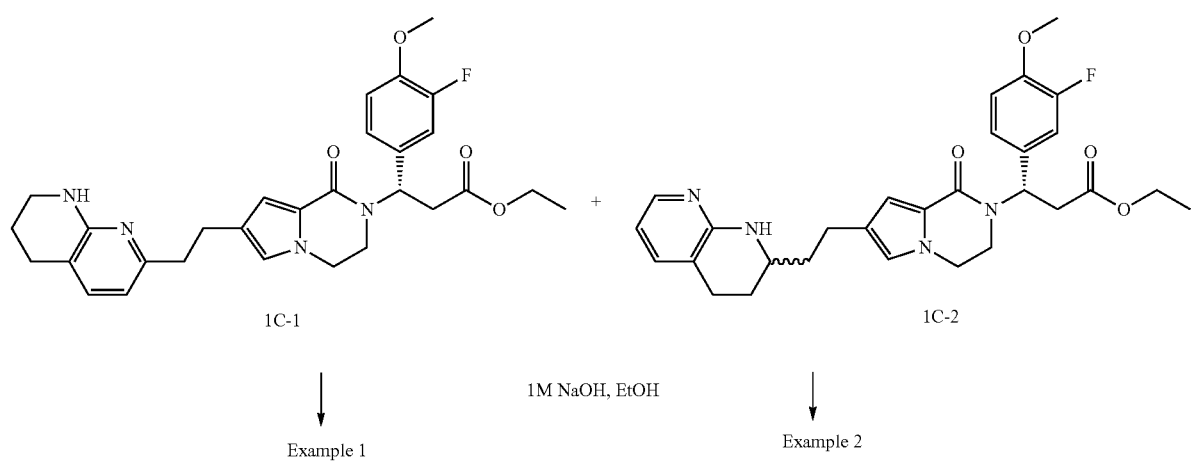
1C-1     +     1C-2
1M NaOH, EtOH
Example 1     Example 2

1A. Ethyl (S,E)-3-(4-(2-(1,8-naphthyridin-2-yl)vinyl)-1H-pyrrole-2-carboxamido)-3-(3-fluoro-4-methoxyphenyl)propanoate: To a solution of Intermediate 19 (13.9 g, 37.0 mmol) and Intermediate 1 (10.3 g, 37.0 mmol) in DMF (185 mL) were added EDC (14.2 g, 73.9 mmol), HOBT (11.3 g, 73.9 mmol) and DIPEA (20.5 mL, 118 mmol). After stirring at room temperature for 2 h, the reaction was diluted with water (200 mL). The precipitate was collected by filtration, washed with water and dried under vacuum to yield 1A (20.0 g, 100%) as a yellow solid. $^1$H NMR (500 MHz, DMSO-$d_6$) 11.76 (br. s., 1H), 9.00 (dd, J=4.1, 1.9 Hz, 1H), 8.52 (d, J=8.5 Hz, 1H), 8.40-8.32 (m, 2H), 7.87-7.76 (m, 2H), 7.51 (dd, J=8.1, 4.3 Hz, 1H), 7.36-7.22 (m, 3H), 7.20-7.10 (m, 2H), 7.04 (d, J=16.2 Hz, 1H), 5.46-5.33 (m, 1H), 4.08-3.97 (m, 2H), 3.83-3.78 (m, 3H), 2.99-2.79 (m, 2H), 1.12 (t, J=7.2 Hz, 3H). HPLC retention time (Method #1): 2.440 min.; LCMS (ES): m/z 489.0 [M+H]$^+$.

1B. Ethyl (S,E)-3-(7-(2-(1,8-naphthyridin-2-yl)vinyl)-1-oxo-3,4-dihydropyrrolo[1,2-a]pyrazin-2(1H)-yl)-3-(3-fluoro-4-methoxyphenyl)propanoate: A mixture of 1A (12.6 g, 23.2 mmol), NBu$_4$Br (7.48 g, 23.2 mmol), 1,2-dibromoethane (10.0 mL, 116 mmol) and IN aq. NaOH (69.6 mL, 69.6 mmol) in dichloroethane (70.8 mL) was stirred at 50° C. for 1 h. After cooling to room temperature, the reaction was diluted with EtOAc (150 mL). The sticky brown precipitate was collected by filtration and washed with EtOAc. The filtrate was washed with water, brine, dried over anhydrous Na$_2$SO$_4$ and concentrated in vacuo. The residue was purified by flash chromatography (silica gel, DCM:MeOH, 100:0 to 93:7) to afford 1B (2.16 g, 18.1%) as a yellow solid. $^1$H NMR (500 MHz, CDCl$_3$) δ 9.07 (dd, J=4.3, 2.1 Hz, 1H), 8.19-8.05 (m, 2H), 7.94 (d, J=16.0 Hz, 1H), 7.54 (d, J=8.3 Hz, 1H), 7.39 (dd, J=8.0, 4.1 Hz, 1H), 7.26 (d, J=1.7 Hz, 1H), 7.16-7.03 (m, 3H), 6.99-6.87 (m, 2H), 6.39-6.24 (m, 1H), 4.19-4.05 (m, 3H), 3.99 (ddd, J=12.2, 7.6, 4.1 Hz, 1H), 3.89 (s, 3H), 3.66-3.54 (m, 1H), 3.31 (ddd, J=12.4, 7.7, 4.1 Hz, 1H), 3.05-2.93 (m, 2H), 1.21 (t, J=7.0 Hz, 3H). HPLC retention time (Method #1): 2.475 min.; LCMS (ES): m/z 515.1 [M+H]$^+$.

1C-1. Ethyl (S)-3-(3-fluoro-4-methoxyphenyl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoate: To a solution of 1B (95 mg, 0.185 mmol) in EtOH (5.0 mL) was added and PtO$_2$ (8.4 mg, 0.037 mmol). The suspension was stirred at room temperature under a H$_2$ atmosphere (1 atm., balloon) for 24 h. Additional PtO$_2$ (8.39 mg, 0.037 mmol) was added and hydrogenation was continued for an additional 24 h. The slurry was filtered through a CELITE® pad and the pad was washed well with EtOH. The filtrate was concentrated in vacuo and the residue was purified by preparative HPLC (Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 38-68% B over 25 minutes, then a 5-minute hold at 68% B; Flow: 20 mL/min.) to afford 1C-1 (33 mg, 32%) as a white solid. $^1$H NMR (500 MHz, CDCl$_3$) 7.16-7.02 (m, 3H), 6.95-6.87 (m, 1H), 6.79 (d, J=1.7 Hz, 1H), 6.54 (d, J=1.4 Hz, 1H), 6.37 (d, J=7.2 Hz, 1H), 6.32-6.27 (m, 1H), 4.12 (qd, J=7.1, 1.0 Hz, 2H), 3.97 (dd, J=7.6, 4.3 Hz, 1H), 3.92-3.82 (m, 4H), 3.53 (ddd, J=12.3, 7.6, 4.3 Hz, 1H), 3.46-3.38 (m, 2H), 3.24 (ddd, J=12.2, 7.7, 4.3 Hz, 1H), 3.03-2.91 (m, 2H), 2.88-2.79 (m, 4H), 2.71 (t, J=6.2 Hz, 2H), 1.92 (quin, J=6.0 Hz, 2H), 1.19 (t, J=7.2 Hz, 3H). HPLC retention time (Method #1): 2.285 min.; LCMS (ES): m/z 521.2 [M+14]$^+$.

1C-2. Ethyl (3S)-3-(3-fluoro-4-methoxyphenyl)-3-(1-oxo-7-(2-(1,2,3,4-tetrahydro-1,8-naphthyridin-2-yl)ethyl)-3,4-dihydropyrrolo[1,2-a]pyrazin-2(1H)-yl)propanoate: The reduction of 1B and subsequent purification via preparative HPLC described for 1C-1 afforded 1C-2 (4.5 mg, 4.5%) as a light yellow solid as a mixture of diastereomers. $^1$H NMR (500 MHz, CDCl$_3$) δ 7.82 (d, J=4.4 Hz, 1H), 7.18 (d, J=7.2 Hz, 1H), 7.11-7.03 (m, 2H), 6.95-6.89 (m, 1H), 6.80 (d, J=1.4 Hz, 1H), 6.53 (s, 1H), 6.50 (dd, J=7.2, 5.2 Hz, 1H), 6.30 (t, J=8.0 Hz, 1H), 4.12 (q, J=7.2 Hz, 2H), 3.99 (dd, J=6.9, 5.0 Hz, 1H), 3.92-3.83 (m, 4H), 3.59-3.51 (m, 1H), 3.45 (d, J=5.0 Hz, 1H), 3.26 (ddd, J=12.4, 7.7, 4.1 Hz, 1H), 3.05-2.92 (m, 2H), 2.77-2.68 (m, 2H), 2.65-2.51 (m, 2H), 2.01-1.94 (m, 1H), 1.85-1.77 (m, 2H), 1.68-1.60 (m, 1H), 1.20 (t, J=7.2 Hz, 3H). HPLC retention time (Method #1): 2.340 min.; LCMS (ES): m/z 521.2 [M+H]$^+$.

Example 1: To a room temperature solution of 1C-1 (11.1 mg, 0.021 mmol) in EtOH (0.388 mL) was added 1M aq. NaOH (64 µL, 0.064 mmol). After stirring for 1 h, the reaction was concentrated in vacuo and acidified to pH~2 with 1M aq. HCl. The mixture was reconcentrated and the residue was purified by preparative HPLC (Column: XBridge C18, 19×200 mm, 5-µm particles; Mobile Phase A: 5:95 CH$_3$CN:H$_2$O with 0.1% TFA; Mobile Phase B: 95:5 CH$_3$CN:H$_2$O with 0.1% TFA; Gradient: 10-50% B over 20 minutes, then a 5-minute hold at 100% B; Flow: 20 mL/min.) to afford Example 1 (5.5 mg, 52%) as an off-white solid. $^1$H NMR (500 MHz, CD$_3$OD) δ 7.39 (d, J=7.2 Hz, 1H), 7.18-7.11 (m, 2H), 7.06 (t, J=8.7 Hz, 1H), 6.61 (d, J=1.4 Hz, 1H), 6.55 (d, J=1.7 Hz, 1H), 6.47 (d, J=7.4 Hz, 1H), 6.26 (t, J=8.0 Hz, 1H), 4.01 (td, J=8.3, 4.0 Hz, 1H), 3.93-3.87 (m, 1H), 3.85 (s, 3H), 3.67 (ddd, J=12.9, 6.9, 4.1 Hz, 1H), 3.48-3.33 (m, 2H), 3.29-3.22 (m, 1H), 2.93 (d, J=8.0 Hz, 2H), 2.86-2.79 (m, 2H), 2.78-2.65 (m, 4H), 1.88 (quin, J=6.0 Hz, 2H). HPLC retention time (Method #1): 2.087 min.; LCMS (ES): m/z 493.1 [M+H]+

Example 2: Example 2 was prepared as a mixture of diastereomers using the procedure described for Example 1. $^1$H NMR (500 MHz, CD$_3$OD) δ 7.66 (br. s., 1H), 7.36 (t, J=5.9 Hz, 1H), 7.18-7.10 (m, 2H), 7.06 (t, J=8.8 Hz, 1H), 6.70-6.63 (m, 2H), 6.60-6.52 (m, 1H), 6.26 (t, J=8.0 Hz, 1H), 4.13-4.01 (m, 1H), 3.98-3.89 (m, 1H), 3.85 (s, 3H), 3.73-3.62 (m, 1H), 3.51-3.39 (m, 1H), 3.27 (d, J=4.4 Hz, 1H), 3.01-2.86 (m, 2H), 2.82-2.67 (m, 2H), 2.58 (q, J=7.6 Hz, 2H), 2.05-1.97 (m, 1H), 1.88-1.80 (m, 1H), 1.75 (dt, J=14.2, 7.2 Hz, 1H), 1.66-1.57 (m, 1H). LCMS (ES): m/z 493.1 [M+H]$^+$.

Alternate Preparation of 1B (1)

1B

Ethyl (S,E)-3-(7-(2-(1,8-naphthyridin-2-yl)vinyl)-1-oxo-3,4-dihydropyrrolo[1,2-a]pyrazin-2(1H)-yl)-3-(3-fluoro-4-methoxyphenyl)propanoate

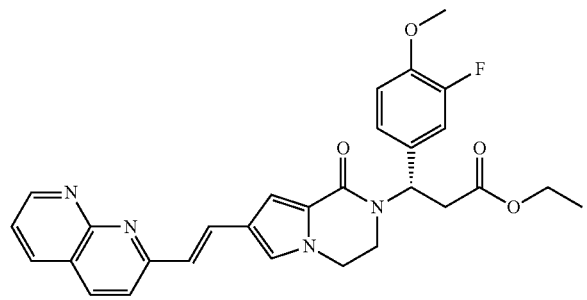

Alternate Preparation of 1B (2)

1B

Ethyl (S,E)-3-(7-(2-(1,8-naphthyridin-2-yl)vinyl)-1-oxo-3,4-dihydropyrrolo[1,2-a]pyrazin-2(1H)-yl)-3-(3-fluoro-4-methoxyphenyl)propanoate and

1E

Ethyl (S)-3-(7-(1,3-di(1,8-naphthyridin-2-yl)propan-2-yl)-1-oxo-3,4-dihydropyrrolo[1,2-a]pyrazin-2(1H)-yl)-3-(3-fluoro-4-methoxyphenyl)propanoate

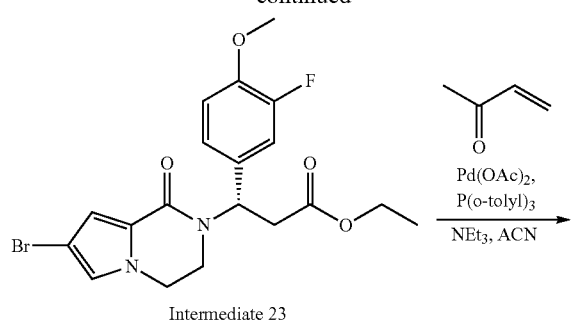

Intermediate 23

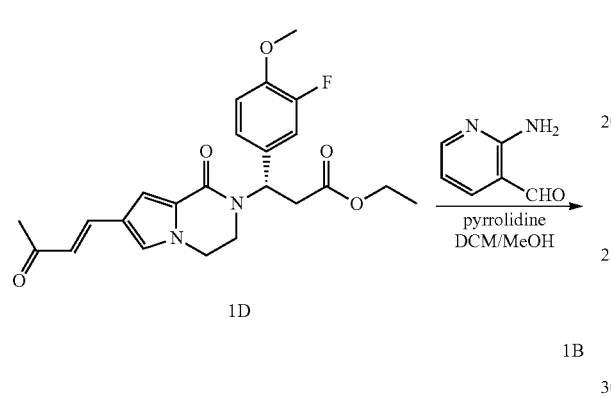

1D

1B

1D. Ethyl (S,E)-3-(3-fluoro-4-methoxy phenyl)-3-(1-oxo-7-(3-oxobut-1-en-1-yl)-3,4-dihydropyrrolo[1,2-a]pyrazin-2(1H)-yl)propanoate: 1D was prepared using the procedure described for Int-1A. $^1$H NMR (500 MHz, CDCl$_3$) δ 7.40 (d, J=16.0 Hz, 1H), 7.16 (d, J=1.7 Hz, 1H), 7.11-7.05 (m, 2H), 6.97-6.90 (m, 2H), 6.48 (d, J=16.0 Hz, 1H), 6.30 (dd, J=9.1, 6.9 Hz, 1H), 4.19-4.04 (m, 3H), 4.02-3.94 (m, 1H), 3.92-3.83 (m, 3H), 3.65-3.52 (m, 1H), 3.31 (td, J=8.2, 3.7 Hz, 1H), 3.07-2.92 (m, 2H), 2.32 (s, 3H), 1.21 (t, J=7.0 Hz, 3H). HPLC retention time (Method #1): 2.878 min.; LCMS (ES): m/z 429.1 [M+H]$^+$.

1B: To a solution of 1D (29.8 mg, 0.070 mmol) and pyrrolidine (1.44 µL, 0.017 mmol) in DCM (0.070 mL) and MeOH (0.209 mL) was added 2-aminonicotinaldehyde (8.49 mg, 0.070 mmol). After stirring at room temperature for 17 h, the solvent was removed in vacuo and the residue was purified by preparative HPLC (Phenomenex® Luna AXIA 5u 21.2×100 mm, 15 min gradient, 10 min run, 20% to 100% Solvent B=90% MeOH-10% H$_2$O-0.1% TFA, Solvent A=10% MeOH-90% H$_2$O-0.1% TFA) to afford 8.4 mg of the TFA salt of 1B. This material was dissolved in MeOH (0.200 mL) and 40 mg Dianion WA21J resin was added. After stirring at room temperature for 1 h, the resin was removed by filtration and washed well with MeOH. The filtrate was concentrated in vacuo to afford 1B (7.0 mg, 20%) as an orange oil. $^1$H NMR (500 MHz, CDCl$_3$) δ 9.08 (br. s., 1H), 8.16-8.06 (m, 2H), 7.92 (d, J=16.0 Hz, 1H), 7.55 (d, J=8.5 Hz, 1H), 7.40 (dd, J=8.0, 4.1 Hz, 1H), 7.26-7.23 (m, 1H), 7.16-7.03 (m, 3H), 6.98-6.88 (m, 2H), 6.32 (s, 1H), 4.19-4.07 (m, 3H), 4.02-3.95 (m, 1H), 3.89 (s, 3H), 3.59 (dd, J=7.4, 4.1 Hz, 1H), 3.33-3.26 (m, 1H), 3.05-2.93 (m, 2H), 1.21 (t, J=7.0 Hz, 3H). HPLC retention time (Method #1): 2.582 min.; LCMS (ES): m/z 515.1 [M+H]$^+$.

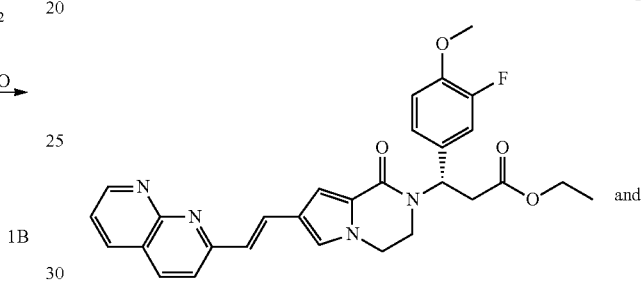

1B and

1E

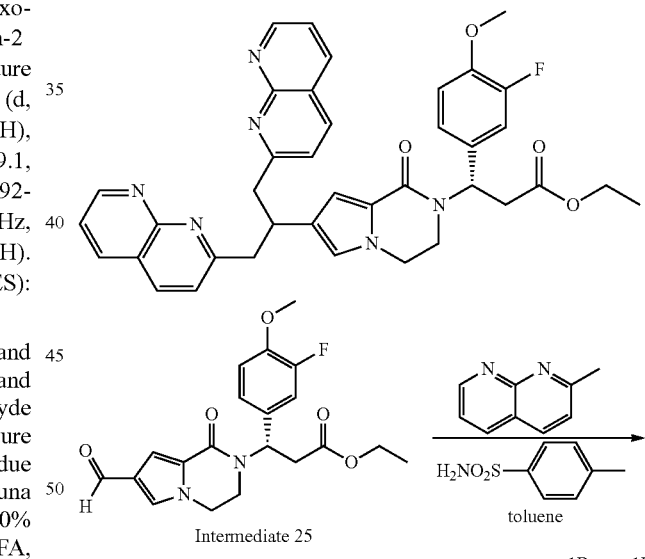

Intermediate 25

1B + 1E 1B and 1E: A solution of 2-Methyl-1,8-naphthyridine (0.037 g, 0.257 mmol), Intermediate 25 (0.100 g, 0.257 mmol) and 4-methylbenzenesulfonamide (0.044 g, 0.257 mmol) in toluene (0.555 mL) was stirred at 110° C. for 14 h. After cooling to room temperature, the solvent was removed in vacuo and the residue was purified by preparative HPLC (Phenomenex Luna AXIA 5u 21.2×100 mm, 10 min gradient, 15 min run, 10% to 100% Solvent B=90% MeOH-10% H$_2$O-0.1% TFA, Solvent A=10% MeOH-90% H$_2$O-0.1% TFA) to afford TFA salts of 1B and 1E, respectively. These salts were individually dissolved in MeOH (1.000 mL) and 250 mg Dianion WA21J resin was added.

After stirring at room temperature for 1 h, the resin was removed by filtration and washed well with MeOH. The filtrates were concentrated in vacuo to afford 1B (25.8 mg, 20%) as an orange-brown oil and 1E (32.5 mg, 19%) as a brown oil, respectively.

1B: $^1$H NMR (500 MHz, CDCl$_3$) δ 9.06 (dd, J=4.1, 1.9 Hz, 1H), 8.16-8.05 (m, 2H), 7.92 (d, J=16.0 Hz, 1H), 7.54 (d, J=8.3 Hz, 1H), 7.39 (dd, J=8.0, 4.1 Hz, 1H), 7.25 (d, J=1.4 Hz, 1H), 7.13-7.04 (m, 3H), 6.98-6.86 (m, 2H), 6.32 (dd, J=8.8, 7.2 Hz, 1H), 4.17-4.05 (m, 3H), 4.02-3.95 (m, 1H), 3.88 (s, 3H), 3.64-3.55 (m, 1H), 3.34-3.25 (m, 1H), 3.05-2.92 (m, 2H), 1.20 (t, J=7.2 Hz, 3H). HPLC retention time (Method #1): 2.430 min.; LCMS (ES): m/z 515.1 [M+H]$^+$ 1E.: $^1$H NMR (500 MHz, CDCl$_3$) δ 9.04 (dd, J=4.1, 1.9 Hz, 1H), 8.07 (dt, J=8.0, 1.5 Hz, 2H), 7.95 (d, J=8.3 Hz, 2H), 7.48-7.31 (m, 4H), 7.08-7.00 (m, 2H), 6.93-6.83 (m, 1H), 6.81 (d, J=1.7 Hz, 1H), 6.52 (d, J=1.7 Hz, 1H), 6.23 (dd, J=8.7, 7.3 Hz, 1H), 4.26 (t, J=7.4 Hz, 1H), 4.07 (q, J=7.1 Hz, 2H), 3.92-3.79 (m, 4H), 3.77-3.68 (m, 1H), 3.48-3.33 (m, 5H), 3.20-3.08 (m, 1H), 3.02-2.81 (m, 3H), 1.12 (t, J=7.2 Hz, 3H). HPLC retention time (Method #1): 2.430 min.; LCMS (ES): m/z 659.2 [M+H]$^+$.

The Examples in the following Table (Table 2) were prepared in similar manners as Example 1. $^1$H NMR was measured at 500 MHz, DMSO-d$_6$, unless otherwise indicated.

TABLE 2

| Example No. | Structure and Name | Analytical Data |
|---|---|---|
| 3 | 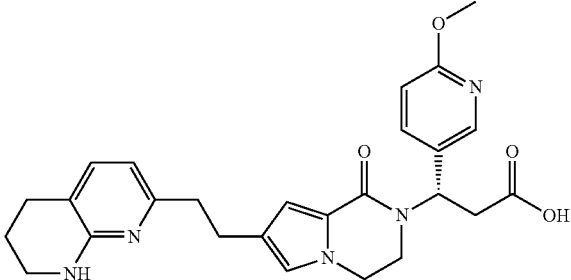<br>(S)-3-(6-Methoxypyridin-3-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | $^1$H NMR (400 MHz, DMSO-d$_6$) δ 12.93-12.05 (m, 1H), 8.19-8.08 (m, 1H), 7.67 (dd, J = 8.7, 2.5 Hz, 1H), 7.02 (d, J = 7.3 Hz, 1H), 6.79 (d, J = 8.6 Hz, 1H), 6.73 (d, J = 1.8 Hz, 1H), 6.49 (d, J = 1.8 Hz, 1H), 6.28 (d, J = 7.3 Hz, 2H), 6.02 (t, J = 8.0 Hz, 1H), 4.05-3.89 (m, 2H), 3.83 (s, 3H), 3.65-3.54 (m, 1H), 3.26-3.16 (m, 3H), 3.07 (d, J = 7.7 Hz, 1H), 2.97 (d, J = 8.1 Hz, 1H), 2.66 (d, J = 4.2 Hz, 4H), 2.60 (t, J = 6.3 Hz, 2H), 1.80-1.63 (m, 2H). LCMS (ES): m/z 476.3 [M + H]$^+$. |
| 4 | 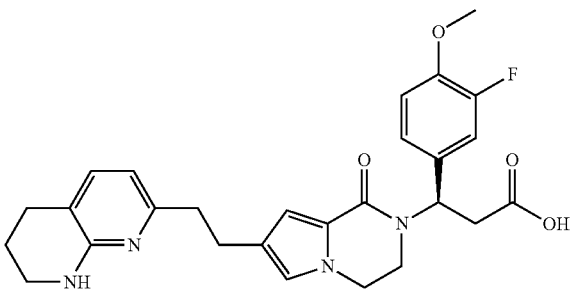<br>(R)-3-(3-Fluoro-4-methoxyphenyl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | H NMR (500 MHz, DMSO-d$_6$) δ 7.24-7.07 (m, 3H), 7.02 (d, J = 7.3 Hz, 1H), 6.72 (s, 1H), 6.50 (s, 1H), 6.32-6.21 (m, 2H), 6.03 (t, J = 7.9 Hz, 1H), 3.93 (dd, J = 19.5, 13.7 Hz, 2H), 3.81 (s, 3H), 3.62-3.49 (m, 1H), 3.23 (br. s., 2H), 3.16 (d, J = 7.9 Hz, 1H), 3.04 (dd, J = 15.3, 7.6 Hz, 1H), 2.89 (dd, J = 15.1, 8.1 Hz, 1H), 2.66 (d, J = 6.4 Hz, 4H), 2.60 (t, J = 6.1 Hz, 2H), 1.79-1.70 (m, 2H). LCMS (ES): m/z 493.1 [M + H]$^+$. |

TABLE 2-continued

| Example No. | Structure and Name | Analytical Data |
|---|---|---|
| 5 | 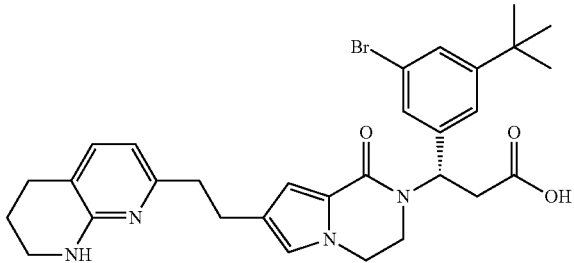<br>(S)-3-(3-Bromo-5-(tert-butyl)phenyl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | $^1$H NMR (500 MHz, DMSO-d$_6$) δ 7.53 (d, J = 7.3 Hz, 1H), 7.41 (s, 1H), 7.28 (d, J = 17.1 Hz, 2H), 6.73 (s, 1H), 6.57 (d, J = 7.3 Hz, 1H), 6.53 (s, 1H), 5.98 (t, J = 7.8 Hz, 1H), 3.99-3.85 (m, 2H), 3.62-3.52 (m, 1H), 3.35 (br. s., 1H), 3.42 (br. s., 1H), 3.20-3.11 (m, 1H), 3.08 (dd, J = 15.6, 7.9 Hz, 1H), 2.96-2.87 (m, 1H), 2.86-2.80 (m, 2H), 2.74-2.64 (m, 4H), 1.76 (d, J = 5.2 Hz, 2H), 1.20 (s, 9H). LCMS (ES): m/z 759.2 [M + H]$^+$. |
| 6 | 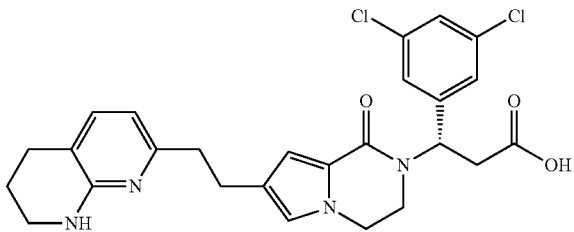<br>(S)-3-(3,5-Dichlorophenyl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | $^1$H NMR (500 MHz, DMSO-d$_6$) δ 7.54 (s, 1H), 7.45 (br. s., 1H), 7.39 (s, 2H), 6.78 (s, 1H), 6.58-6.49 (m, 2H), 5.97 (t, J = 7.6 Hz, 1H), 3.99 (br. s., 2H), 3.69-3.58 (m, 1H), 3.36 (br. s., 1H), 3.32-3.24 (m, 1H), 3.20-3.12 (m, 1H), 3.00 (dd, J = 16.0, 8.1 Hz, 1H), 2.82 (d, J = 7.6 Hz, 2H), 2.77-2.65 (m, 4H), 1.80 (br. s., 2H). LCMS (ES): m/z 513.0 [M + H]$^+$. |
| 7 | 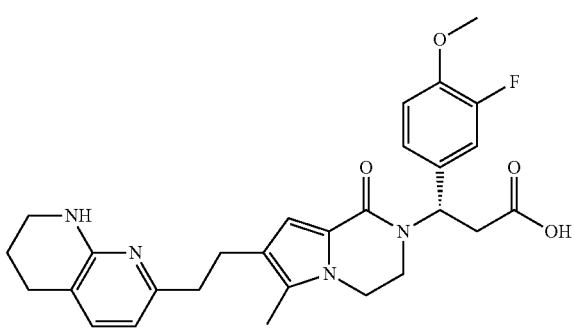<br>(S)-3-(3-Fluoro-4-methoxyphenyl)-3-(6-methyl-1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | $^1$H NMR (500 MHz, DMSO-d$_6$) δ 7.51 (br. s., 1H), 7.23-7.04 (m, 4H), 6.58 (d, J = 6.6 Hz, 1H), 6.52 (s, 1H), 6.02 (t, J = 7.9 Hz, 1H), 3.85 (br. s., 2H), 3.81 (s, 3H), 3.57 (br. s., 1H), 3.13 (br. s., 1H), 3.06 (dd, J = 15.1, 7.6 Hz, 1H), 2.91 (dd, J = 15.3, 8.2 Hz, 1H), 2.78 (d, J = 7.5 Hz, 2H), 2.74-2.64 (m, 4H), 2.07 (s, 3H), 1.81 (br. s., 2H). LCMS (ES): m/z 507.1 [M + H]$^+$. |

TABLE 2-continued

| Example No. | Structure and Name | Analytical Data |
|---|---|---|
| 8 | 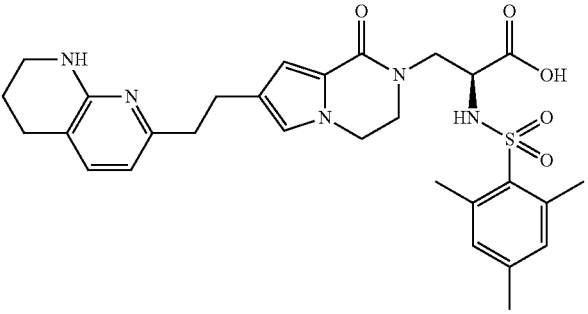<br>(S)-3-(1-Oxo-7-(2-(5,6,7,8-tetrahydro-1,8-naphthyridin-2-yl)ethyl)-3,4-dihydropyrrolo[1,2-a]pyrazin-2(1H)-yl)-2-((2,4,6-trimethylphenyl)sulfonamido)propanoic acid | $^1$H NMR (500 MHz, DMSO-$d_6$) δ 7.40 (br. s., 1H), 6.85 (s, 2H), 6.72 (s, 1H), 6.55-6.41 (m, 2H), 4.01 (d, J = 5.8 Hz, 1H), 3.85 (br. s., 2H), 3.79-3.71 (m, 1H), 3.34 (br. s., 2H), 2.98 (s, 2H), 2.81 (d, J = 7.3 Hz, 2H), 2.74 (d, J = 7.7 Hz, 2H), 2.67 (br. s., 3H), 2.48 (s, 6H), 2.17 (s, 3H), 1.78 (br. s., 2H). LCMS (ES): m/z 566.5 [M + H]$^+$. |
| 9 | 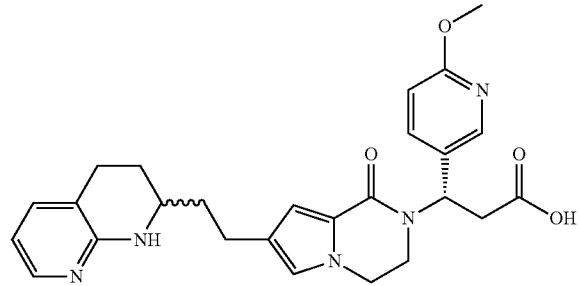<br>(3S)-3-(6-Methoxypyridin-3-yl)-3-(1-oxo-7-(2-(1,2,3,4-tetrahydro-1,8-naphthyridin-2-yl)ethyl)-3,4-dihydropyrrolo[1,2-a]pyrazin-2(1H)-yl)propanoic acid | $^1$H NMR (400 MHz, DMSO-$d_6$) δ 8.14 (d, J = 2.42 Hz, 1H), 7.74 (dd, J = 1.65, 4.95 Hz, 1H), 7.67 (dd, J = 2.42, 8.58 Hz, 1H), 7.13 (d, J = 6.16 Hz, 1H), 6.73-6.82 (m, 2H), 6.54 (d, J = 1.54 Hz, 1H), 6.39 (dd, J = 4.84, 7.04 Hz, 1H), 6.28 (s, 1H), 6.02 (t, J = 7.92 Hz, 1H), 3.89-4.05 (m, 2H), 3.82 (s, 3H), 3.57-3.66 (m, 1H), 3.18-3.25 (m, 3H), 3.04 (dd, J = 7.48, 14.75 Hz, 1H), 2.82-2.93 (m, 1H), 2.61-2.69 (m, 2H), 1.83-1.91 (m, 2H), 1.70-1.82 (m, 1H), 1.56-1.67 (m, 1H), 1.42-1.54 (m, 1H). LCMS (ES): m/z 476.3 [M + H]$^+$. |
| 10 | 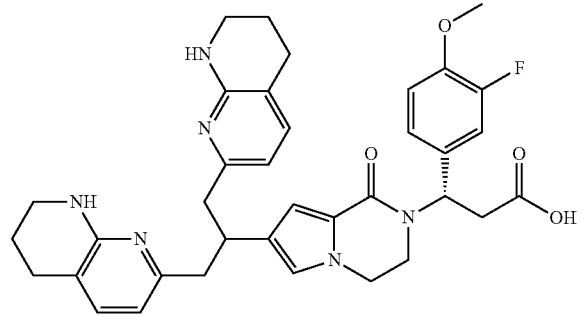<br>(S)-3-(7-(1,3-Bis(5,6,7,8-tetrahydro-1,8-naphthyridin-2-yl)propan-2-yl)-1-oxo-3,4-dihydropyrrolo[1,2-a]pyrazin-2(1H)-yl)-3-(3-fluoro-4-methoxyphenyl)propanoic acid | $^1$H NMR (500 MHz, DMSO-$d_6$) δ 7.18-7.08 (m, 3H), 6.95 (br d, J = 7.0 Hz, 2H), 6.61 (s, 1H), 6.46 (s, 1H), 6.23 (br s, 1H), 6.17 (br d, J = 7.3 Hz, 2H), 6.00 (br t, J = 7.8 Hz, 1H), 3.94-3.84 (m, 2H), 3.80 (s, 3H), 3.59-3.47 (m, 1H), 3.47-3.32 (m, 1H), 3.21 (br s, 4H), 3.16-3.09 (m, 1H), 3.02 (br dd, J = 15.4, 7.8 Hz, 1H), 2.87 (br dd, J = 15.1, 7.8 Hz, 1H), 2.66-2.59 (m, 4H), 2.58-2.54 (m, 4H), 1.77-1.65 (m, 4H) LCMS (ES): m/z 639.0 [M + H]$^+$. |

Separation of diastereomers of Example 9.

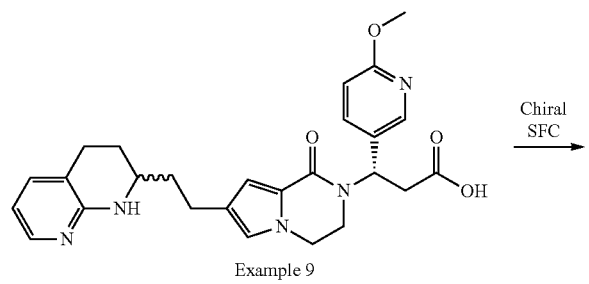

Example 9

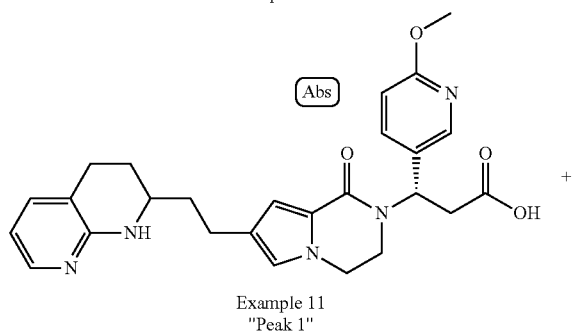

Example 11
"Peak 1"

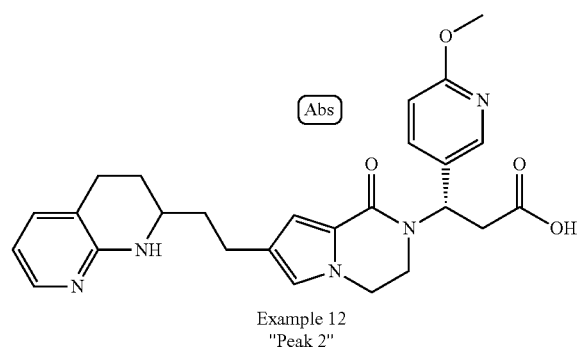

Example 12
"Peak 2"

Example 11, Peak 1

(3S)-3-(6-Methoxypyridin-3-yl)-3-(1-oxo-7-(2-(1,2,3,4-tetrahydro-1,8-naphthyridin-2-yl)ethyl)-3,4-dihydropyrrolo[1,2-a]pyrazin-2(1H)-yl)propanoic acid

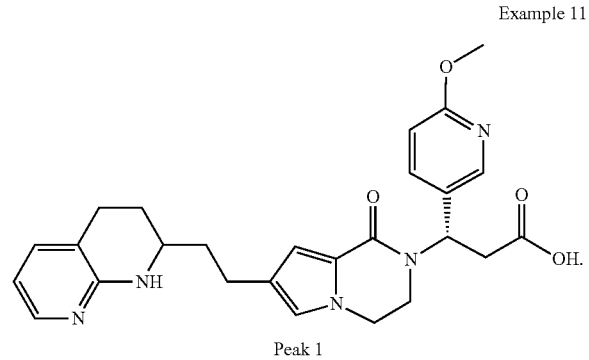 [SMILES: COc1ccc([C@H](CC(=O)O)N2CCn3cc(CCC4CCc5cccnc5N4)cc3C2=O)cn1]

Example 11
Peak 1

Example 11: Chiral SFC separation of Example 9 (Dionex Ultimate 3000; Column: Chiralpak ID 21×250 mm, 5 micron; Mobile Phase: 10 mM Ammonium Acetate in (50% MeOH, 50% Acetonitrile); Flow Conditions: 20 mL/min.; Detector Wavelength: 220 nm; Injection Details: 600 uL of 40 mg/mL in MeOH) afforded Example 11 as a white solid as a single diastereomer. Peak 1, faster eluting peak. $^1$H NMR (400 MHz, CD$_3$OD) δ 8.17 (d, J=2.20 Hz, 1H), 7.72 (dd, J=2.53, 8.69 Hz, 1H), 7.63 (br. s., 1H), 7.43 (d, J=7.04 Hz, 1H), 6.78 (d, J=8.58 Hz, 1H), 6.68-6.75 (m, 2H), 6.61 (t, J=6.16 Hz, 1H), 6.24 (t, J=8.03 Hz, 1H), 4.04-4.14 (m, 1H), 3.92-4.01 (m, 1H), 3.88 (s, 3H), 3.67-3.77 (m, 1H), 3.44-3.53 (m, 1H), 2.71-2.99 (m, 4H), 2.61 (t, J=7.70 Hz, 2H), 1.97-2.05 (m, 1H), 1.84-1.91 (m, 2H), 1.74-1.82 (m, 1H), 1.57-1.68 (m, 1H). LCMS (ES): m/z 476.4 [M+H]$^+$.

Example 12, Peak 2

(3S)-3-(6-Methoxypyridin-3-yl)-3-(1-oxo-7-(2-(1,2,3,4-tetrahydro-1,8-naphthyridin-2-yl)ethyl)-3,4-dihydropyrrolo[1,2-a]pyrazin-2(1H)-yl)propanoic acid

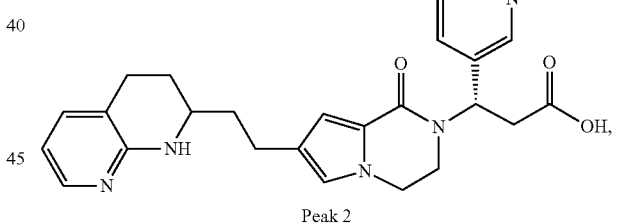

Peak 2

Example 12: Chiral SFC separation of Example 9 (Dionex Ultimate 3000; Column: Chiralpak ID 21×250 mm, 5 micron; Mobile Phase: 10 mM Ammonium Acetate in (50% MeOH, 50% Acetonitrile); Flow Conditions: 20 mL/min.; Detector Wavelength: 220 nm; Injection Details: 600 uL of 40 mg/mL in MeOH) afforded Example 12 as a white solid as a single diastereomer. Peak 2, slower eluting peak. $^1$H NMR (400 MHz, CD$_3$OD) δ 8.18 (d, J=2.42 Hz, 1H), 7.72 (dd, J=2.53, 8.69 Hz, 1H), 7.57-7.70 (m, 1H), 7.38 (d, J=7.26 Hz, 1H), 6.78 (d, J=8.58 Hz, 1H), 6.71 (d, J=4.84 Hz, 2H), 6.58 (br. s., 1H), 6.25 (t, J=7.92 Hz, 1H), 4.04-4.15 (m, 1H), 3.92-4.01 (m, 1H), 3.88 (s, 3H), 3.67-3.77 (m, 1H), 3.42-3.51 (m, 1H), 3.33-3.38 (m, 1H), 2.87-2.97 (m, 2H), 2.71-2.83 (m, 2H), 2.60 (t, J=7.70 Hz, 2H), 1.83-1.89 (m, 2H), 1.70-1.82 (m, 2H), 1.56-1.67 (m, 1H). LCMS (ES): m/z 476.4 [M+H]$^+$.

Alternate Preparation of Example 3
Example 3
(S)-3-(6-Methoxypyridin-3-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid
Example 3
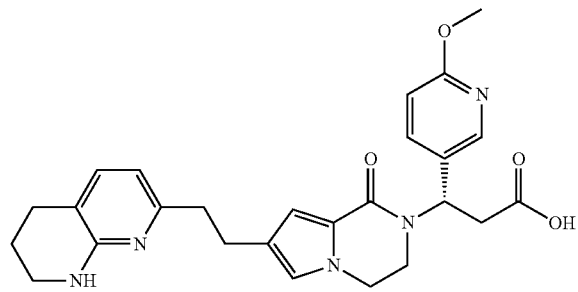
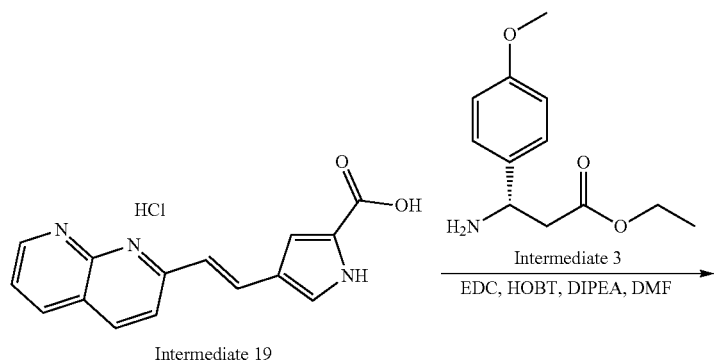
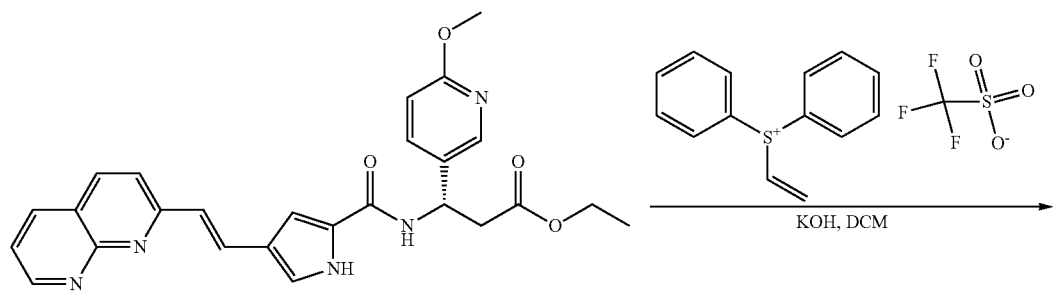

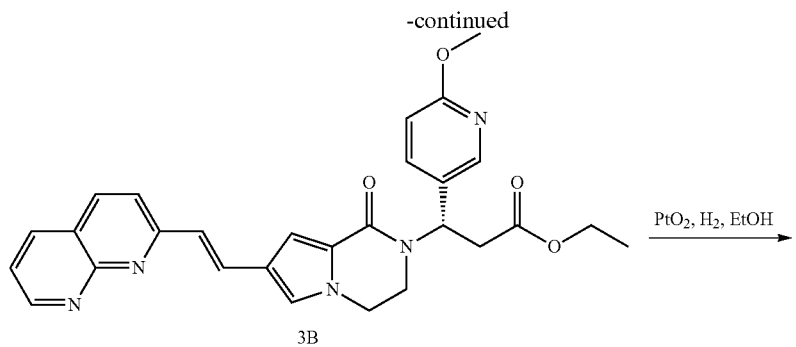

3B

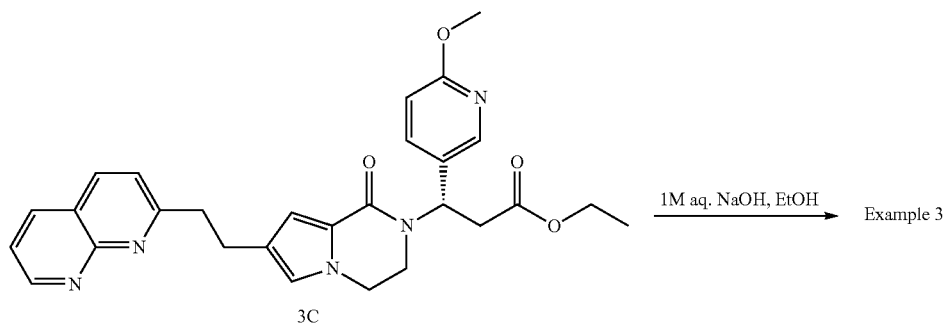

3C

3A. Ethyl (S,E)-3-(4-(2-(1,8-naphthyridin-2-yl)vinyl)-1H-pyrrole-2-carboxamido)-3-(6-methoxypyridin-3-yl)propanoate. 3A was prepared using the procedure described for 1A. $^1$H NMR (500 MHz, DMSO-$d_6$) δ 11.76 (br. s., 1H), 9.00 (dd, J=4.3, 2.1 Hz, 1H), 8.56 (d, J=8.3 Hz, 1H), 8.40-8.30 (m, 2H), 8.19 (d, J=2.5 Hz, 1H), 7.90-7.72 (m, 3H), 7.51 (dd, J=8.1, 4.3 Hz, 1H), 7.31 (br. s., 1H), 7.22 (s, 1H), 7.04 (d, J=16.2 Hz, 1H), 6.81 (d, J=8.8 Hz, 1H), 5.48-5.32 (m, 1H), 4.04 (q, J=7.0 Hz, 2H), 3.83 (s, 3H), 3.06-2.94 (m, 1H), 2.91-2.81 (m, 1H), 1.12 (t, J=7.2 Hz, 3H). HPLC retention time (Method #2): 1.332 min.; LCMS (ES): m/z 472.7 [M+H]$^+$.

3B. Ethyl (S,E)-3-(7-(2-(1,8-naphthyridin-2-yl)vinyl)-1-oxo-3,4-dihydropyrrolo[1,2-a]pyrazin-2(1H)-yl)-3-(6-methoxypyridin-3-yl)propanoate. To a 0° C. solution of 3A (0.250 g, 0.530 mmol) in DCM (35.3 mL) was added KOH (0.074 g, 1.33 mmol). After stirring for 10 min, a solution of diphenylsulphonium triflate (0.231 g, 0.636 mmol) in DCM (8.83 mL) was added dropwise and stirring was continued at 0° C. for 10 min. The ice-bath was removed and the reaction was stirred at room temperature for 1 h. The reaction mixture was filtered through a CELITE® pad, the filtrate was concentrated in vacuo and the residue was purified by preparative HPLC (Luna-AXIA C18 21.5×250 mm 5 μm, 25 min gradient, 31 min run, 15% to 100% Solvent B=90% MeOH-10% H$_2$O-10 mM NH$_4$OAc, Solvent A=10% MeOH-90% H$_2$O-10 mM NH$_4$OAc) to afford 3B (0.168 g, 64%) as a yellow solid. $^1$H NMR (500 MHz, CD$_3$OD) 8.98 (dd, J=4.4, 1.9 Hz, 1H), 8.34 (dd, J=8.3, 1.9 Hz, 1H), 8.30 (d, J=8.5 Hz, 1H), 8.18 (d, J=2.5 Hz, 1H), 7.82 (d, J=6.1 Hz, 1H), 7.80 (d, J=1.1 Hz, 1H), 7.73 (dd, J=8.7, 2.6 Hz, 1H), 7.52 (dd, J=8.0, 4.4 Hz, 1H), 7.26 (d, J=1.4 Hz, 1H), 7.21 (d, J=1.7 Hz, 1H), 7.15 (d, J=16.0 Hz, 1H), 6.82 (d, J=8.5 Hz, 1H), 6.25 (t, J=8.0 Hz, 1H), 4.18 (s, 1H), 4.14-4.05 (m, 3H), 3.91 (s, 3H), 3.75 (ddd, J=12.9, 7.2, 4.1 Hz, 1H), 3.44-3.35 (m, 1H), 3.20-3.10 (m, 2H), 1.19 (t, J=7.2 Hz, 3H). HPLC retention time (Method #2): 1.438 min.; LCMS (ES): m/z 498.4 [M+H]$^+$.

3C. Ethyl (S)-3-(6-methoxypyridin-3-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoate, 2 TFA. To a solution of 3B (30 mg, 0.060 mmol) in EtOH (1.10 mL) was added and PtO$_2$ (2.7 mg, 0.012 mmol). The suspension was stirred at room temperature under a H$_2$ atmosphere (1 atm., balloon) for 5 h. The slurry was filtered through a CELITE® pad, the filtrate was concentrated in vacuo and the residue was purified by preparative HPLC (Phenomenex Luna AXIA 5u C18 21.2×100 mm, 10 min gradient, 12 min run, 10% to 100% Solvent B=90% MeOH-10% H$_2$O-0.1% TFA, Solvent A=10% MeOH-90% H$_2$O-0.1% TFA) to afford 3C (36.6 mg, 83%) as a yellow oil. $^1$H NMR (500 MHz, CD$_3$OD) δ8.16 (d, J=2.5 Hz, 1H), 7.74 (dd, J=8.8, 2.5 Hz, 1H), 7.55 (d, J=7.4 Hz, 1H), 6.85 (d, J=8.8 Hz, 1H), 6.72 (d, J=1.4 Hz, 1H), 6.66 (d, J=1.7 Hz, 1H), 6.59 (d, J=7.4 Hz, 1H), 6.20 (t, J=8.0 Hz, 1H), 4.17-4.02 (m, 3H), 4.00-3.94 (m, 1H), 3.92 (s, 3H), 3.74-3.64 (m, 1H), 3.53-3.45 (m, 2H), 3.33 (d, J=0.6 Hz, 1H), 3.18-3.09 (m, 2H), 2.92 (d, J=7.4 Hz, 2H), 2.86 (d, J=7.4 Hz, 2H), 2.80 (t, J=6.2 Hz, 2H), 2.01-1.88 (m, 2H), 1.26-1.11 (m. 3H). LCMS (ES): m/z 504.2 [M+H]$^+$.

Example 3: Example 3 was prepared using the procedure described for Example 1. $^1$H NMR (500 MHz, DMSO-$d_6$) δ 12.18 (br. s, 1H), 8.14 (d, J=2.2 Hz, 1H), 7.67 (dd, J=8.5, 2.5 Hz, 1H), 7.01 (d, J=7.4 Hz, 1H), 6.79 (d, J=8.5 Hz, 1H), 6.72

(d, J=1.7 Hz, 1H), 6.49 (d, J=1.9 Hz, 1H), 6.30-6.24 (m, 2H), 6.02 (t, J=8.0 Hz, 1H), 4.04-3.89 (m, 2H), 3.83 (s, 3H), 3.66-3.56 (m, 1H), 3.26-3.17 (m, 3H), 3.07 (dd, J=15.5, 7.8 Hz, 1H), 2.97-2.88 (m, 1H), 2.72-2.66 (m, 2H), 2.66-2.62 (m, 2H), 2.60 (t, J=6.2 Hz, 2H), 1.79-1.68 (m, 2H). HPLC retention time (Method #2): 1.245 min.; LCMS (ES): m/z 476.5 [M+H]+

The Examples in the following Table (Table 3) were prepared in a similar manner as the alternate preparation of Example 3. $^1$H NMR was measured at 500 MHz, DMSO-$d_6$ unless otherwise indicated.

TABLE 3

| Example No. | Structure and Name | Analytical Data |
|---|---|---|
| 13 | (±)-3-(2-Methylpyrimidin-5-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | $^1$H NMR (500 MHz, DMSO-$d_6$) δ 8.67 (s, 2H), 7.01 (d, J = 7.2 Hz, 1H), 6.74 (s, 1H), 6.49 (d, J = 1.3 Hz, 1H), 6.31 (br. s., 1H), 6.27 (d, J = 7.2 Hz, 1H), 5.93 (t, J = 7.8 Hz, 1H), 4.07-3.92 (m, 2H), 3.73-3.56 (m, 1H), 3.23 (br. s., 3H), 3.15-3.08 (m, 1H), 2.99 (d, J = 7.5 Hz, 1H), 2.71-2.62 (m, 4H), 2.61-2.57 (m, 5H), 1.79-1.67 (m, 2H). LCMS (ES): m/z 461.2 [M + H]+. |
| 14 | (±)-3-(2-Methylpyrimidin-5-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | $^1$H NMR (500 MHz, DMSO-$d_6$) δ 8.60 (s, 2H), 7.02 (d, J = 7.4 Hz, 1H), 6.75 (s, 1H), 6.49 (s, 1H), 6.28 (d, J = 7.2 Hz, 2H), 5.92 (t, J = 7.7 Hz, 1H), 4.09-3.94 (m, 2H), 3.90 (s, 3H), 3.74-3.61 (m, 1H), 3.24 (br. s., 3H), 3.08 (br. s., 1H), 2.97 (br. s., 1H), 2.76-2.64 (m, 4H), 2.61 (t, J = 6.1 Hz, 2H), 1.79-1.69 (m, 2H). LCMS (ES): m/z 477.1 [M + H]+. |
| 15 | (±)-3-(1-Oxo-7-(2-(5,6,7,8-tetrahydro-1,8-naphthyridin-2-yl)ethyl)-3,4-dihydropyrrolo[1,2-a]pyrazin-2(1H)-yl)-3-(pyrimidin-5-yl)propanic acid | $^1$H NMR (500 MHz, DMSO-$d_6$) δ 9.06 (s, 1H), 8.76 (s, 2H), 7.01 (d, J = 7.2 Hz, 1H), 6.74 (s, 1H), 6.48 (s, 1H), 6.27 (d, J = 7.3 Hz, 1H), 5.96-5.86 (m, 1H), 4.00 (d, J = 15.3 Hz, 2H), 3.69 (d, J = 12.6 Hz, 1H), 3.39 (br. s., 1H), 3.22 (br. s., 2H), 2.97 (d, J = 12.8 Hz, 1H), 2.77 (br. s., 1H), 2.65 (d, J = 6.8 Hz, 4H), 2.59 (t, J = 6.1 Hz, 2H), 1.74 (d, J = 5.5 Hz, 2H). LCMS (ES): m/z 447.1 [M + H]+. |

TABLE 3-continued

| Example No. | Structure and Name | Analytical Data |
|---|---|---|
| 16 | 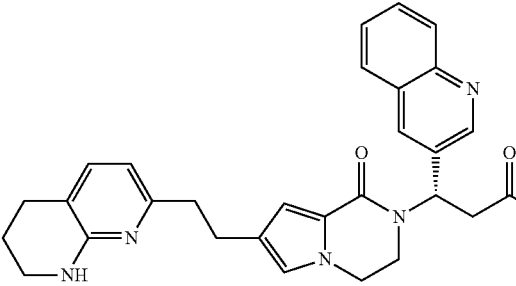<br>(S)-3-(1-Oxo-7-(2-(5,6,7,8-tetrahydro-1,8-naphthyridin-2-yl)ethyl)-3,4-dihydropyrrolo[1,2-a]pyrazin-2(1H)-yl)-3-(quinolin-3-yl)propanoic acid | $^1$H NMR (500 MHz, DMSO-$d_6$) δ 8.79 (s, 1H), 8.28 (br. s., 1H), 7.94 (t, J = 8.4 Hz, 2H), 7.71 (t, J = 7.5 Hz, 1H), 7.57 (t, J = 7.3 Hz, 1H), 6.98 (d, J = 7.3 Hz, 1H), 6.68 (s, 1H), 6.49 (s, 1H), 6.29-6.15 (m, 2H), 3.95 (d, J = 6.7 Hz, 1H), 3.88 (d, J = 5.8 Hz, 1H), 3.60 (br. s., 1H), 3.29-3.12 (m, 4H), 2.94 (dd, J = 15.6, 7.6 Hz, 1H), 2.61 (d, J = 5.2 Hz, 4H), 2.56-2.51 (m, 2H), 1.69 (d, J = 5.2 Hz, 2H). LCMS (ES): m/z 496.2 [M + H]$^+$. |
| 17 | 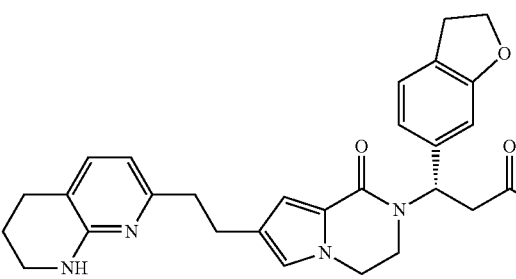<br>(S)-3-(2,3-Dihydrobenzofuran-6-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid, TFA | $^1$H NMR (500 MHz, DMSO-$d_6$) δ 7.54 (d, J = 7.2 Hz, 1H), 7.17 (d, J = 7.7 Hz, 1H), 6.81-6.73 (m, 2H), 6.70 (s, 1H), 6.59 (d, J = 7.3 Hz, 1H), 6.54 (s, 1H), 6.02 (t, J = 7.7 Hz, 1H), 4.49 (t, J = 8.7 Hz, 2H), 3.99-3.88 (m, 2H), 3.77-3.67 (m, 2H), 3.37 (br. s., 1H), 3.21-3.07 (m, 3H), 3.01 (dd, J = 15.4, 7.9 Hz, 1H), 2.85 (t, J = 7.8 Hz, 3H), 2.76-2.65 (m, 4H), 1.80 (br. s., 2H). LCMS (ES): m/z 487.1 [M + H]$^+$. |
| 18 | 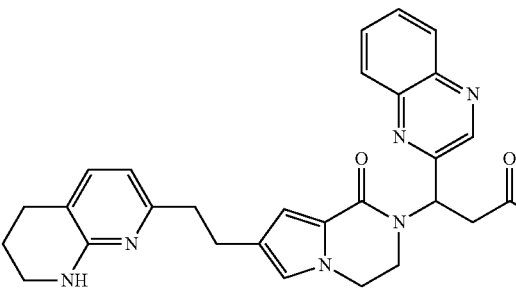<br>(±)-3-(1-Oxo-7-(2-(5,6,7,8-tetrahydro-1,8-naphthyridin-2-yl)ethyl)-3,4-dihydropyrrolo[1,2-a]pyrazin-2(1H)-yl)-3-(quinoxalin-2-yl)propanoic acid, TFA | $^1$H NMR (400 MHz, CD$_3$OD) δ 8.90 (s, 1H), 8.16-8.02 (m, 2H), 7.91-7.80 (m, 2H), 7.56 (d, J = 7.5 Hz, 1H), 6.73 (d, J = 1.5 Hz, 1H), 6.69 (d, J = 1.5 Hz, 1H), 6.60 (d, J = 7.3 Hz, 1H), 6.47 (t, J = 7.6 Hz, 1H), 4.10 (br dd, J = 7.3, 4.2 Hz, 1H), 4.04-3.95 (m, 1H), 3.91-3.80 (m, 1H), 3.66-3.52 (m, 2H), 3.50-3.45 (m, 2H), 3.13 (dd, J = 16.2, 7.4 Hz, 1H), 2.92 (br d, J = 7.3 Hz, 2H), 2.86 (br d, J = 7.0 Hz, 2H), 2.80 (t, J = 6.2 Hz, 2H), 1.94 (quin, J = 5.9 Hz, 2H). LCMS (ES): m/z 497.4 [M + H]$^+$. |

TABLE 3-continued

| Example No. | Structure and Name | Analytical Data |
|---|---|---|
| 19 | 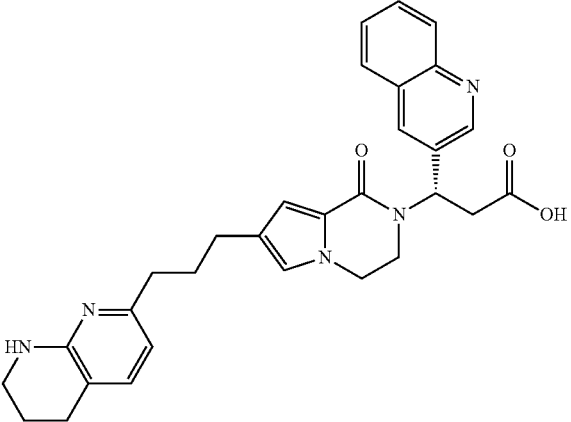<br><br>(S)-3-(1-Oxo-7-(3-(5,6,7,8-tetrahydro-1,8-naphthyridn-2-yl)propyl)-3,4-dihydropyrrolo[1,2-a]pyrazin-2(1H)-yl)-3-(quinolin-3-yl)propanoic acid | $^1$H NMR (500 MHz, DMSO-$d_6$) δ 8.85 (br. s, 1H), 8.32 (br. s., 1H), 7.99 (d, J = 7.8 Hz, 2H), 7.73 (t, J = 7.6 Hz, 1H), 7.64-7.54 (m, 1H), 7.02 (d, J = 7.2 Hz, 1H), 6.72 (s, 1H), 6.53 (s, 1H), 6.25 (d, J = 7.2 Hz, 2H), 6.11 (br. s., 1H), 4.03 (br. s., 1H), 3.93 (br. s., 1H), 3.68 (br. s., 2H), 3.28-3.20 (m, 2H), 3.18-3.13 (m, 2H), 2.58 (d, J = 5.9 Hz, 2H), 2.42 (t, J = 7.5 Hz, 2H), 2.37-2.30 (m, 2H), 1.82-1.67 (m, 4H). LCMS (ES): m/z 510.5 [M + H]$^+$. |
| 20 | 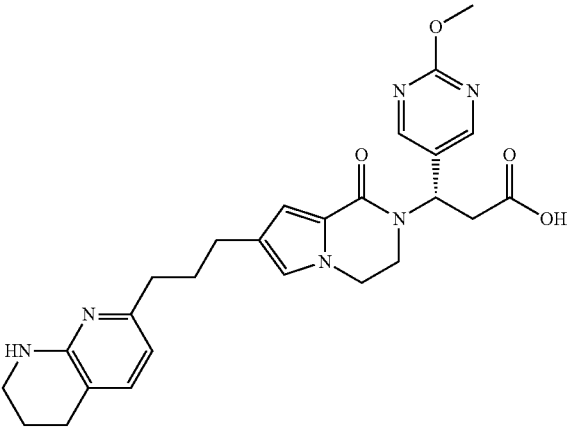<br><br>(S)-3-(2-Methoxypyrimidin-5-yl)-3-(1-oxo-7-(3-(5,6,7,8-tetrahydro-1,8-naphthyridin-2-yl)propyl)-3,4-dihydropyrrolo[1,2-a]pyrazin-2(1H)-yl)propanoic acid | $^1$H NMR (500 MHz, DMSO-$d_6$) δ 8.60-8.56 (m, 2H), 7.04 (d, J = 7.3 Hz, 1H), 6.74 (s, 1H), 6.51 (s, 1H), 6.26 (d, J = 7.3 Hz, 1H), 5.90 (br t, J = 7.9 Hz, 1H), 4.05-3.95 (m, 2H), 3.92-3.87 (m, 3H), 3.62 (br d, J = 13.1 Hz, 1H), 3.41-3.31 (m, 1H), 3.23 (br s, 2H), 3.13 (br dd, J = 15.7, 7.5 Hz, 1H), 3.07-2.98 (m, 1H), 2.59 (br t, J = 6.1 Hz, 2H), 2.42 (br t, J = 7.5 Hz, 2H), 2.35 (br t, J = 7.3 Hz, 2H), 1.83-1.67 (m, 4H). LCMS (ES): m/z 491.4 [M + H]$^+$. |

TABLE 3-continued

| Example No. | Structure and Name | Analytical Data |
|---|---|---|
| 21 | 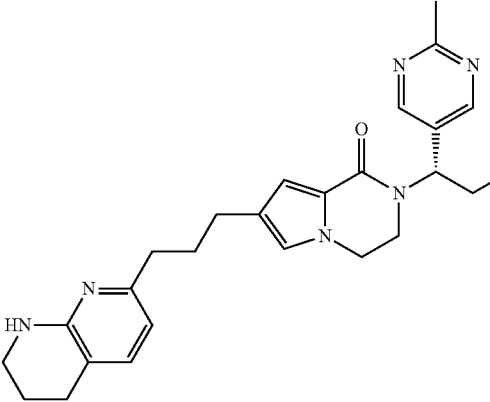

(S)-3-(2-Methylpyrimidin-5-yl)-3-(1-oxo-7-(3-(5,6,7,8-tetrahydro-1,8-naphthyridin-2-yl)propyl)-3,4-dihydropyrrolo[1,2-a]pyrazin-2(1H)-yl)propanoic acid | $^1$H NMR (500 MHz, DMSO-d$_6$) δ 8.66 (s, 2H), 7.02 (d, J = 7.3 Hz, 1H), 6.73 (s, 1H), 6.50 (s, 1H), 6.24 (d, J = 7.3 Hz, 1H), 5.91 (br t, J = 7.6 Hz, 1H), 4.05-3.94 (m, 2H), 3.60-3.54 (m, 1H), 3.40-3.32 (m, 1H), 3.22 (br s, 2H), 3.15-3.09 (m, 1H), 3.04-2.95 (m, 1H), 2.61-2.55 (m, 5H), 2.41 (br t, J = 7.5 Hz, 2H), 2.35 (br t, J = 7.5 Hz, 2H), 1.83-1.64 (m, 4H). LCMS (ES): m/z 475.5 [M + H]$^+$. |

Example 22

(S)-3-(6-Isobutoxypyridin-3-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid

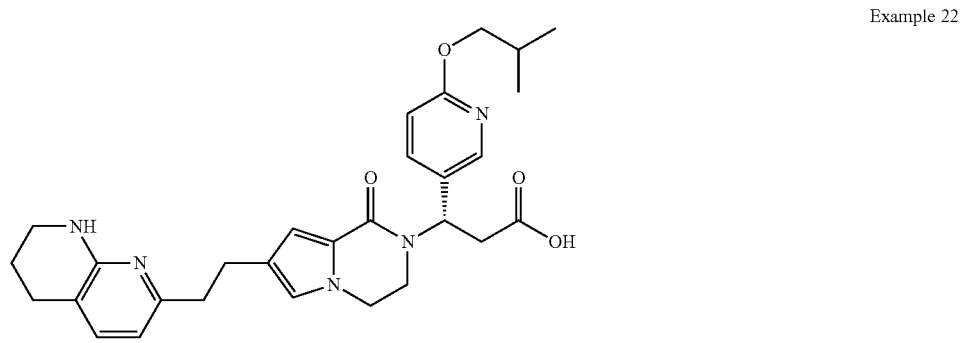

Example 22

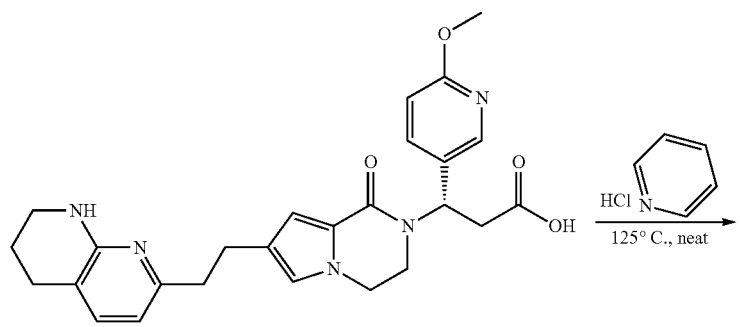

Example 3

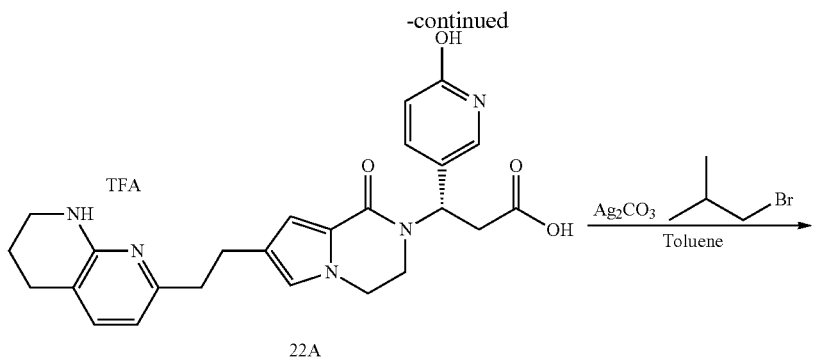

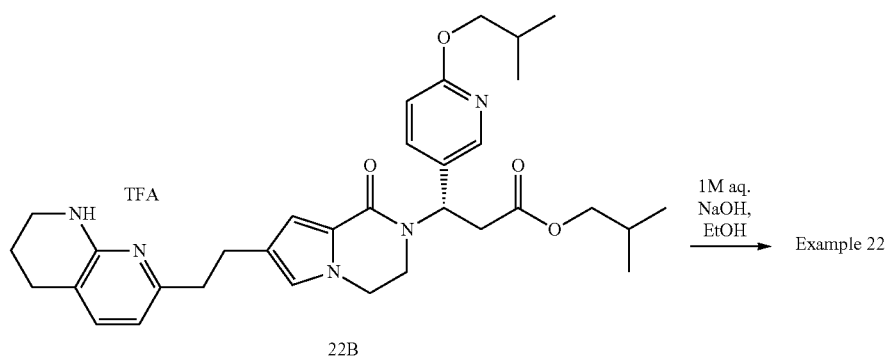

22A. (S)-3-(6-Hydroxypyridin-3-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid, TFA: Example 3 (25 mg, 0.053 mmol) and pyridine hydrochloride (75 mg, 0.65 mmol) were stirred in a sealed reaction vial at 125° C. for 7.5 min. (Neat melt). The reaction mixture was cooled to room temperature and purified by Prep. HPLC (Phenomenex Luna AXIA 5u C18 21.2×100 mm, 10 min gradient, 12 min run, 0% to 100% Solvent B=90% ACN-10% $H_2O$-0.1% TFA, Solvent A=10% ACN-90% $H_2O$-0.1% TFA) to afford 22A (23 mg, 63%) as a clear solid. $^1$H NMR (500 MHz, $CD_3OD$) δ 7.62 (dd, J=9.4, 2.8 Hz, 1H), 7.55 (d, J=7.2 Hz, 1H), 7.47 (d, J=2.5 Hz, 1H), 6.72 (d, J=1.7 Hz, 1H), 6.66 (d, J=1.9 Hz, 1H), 6.59 (d, J=7.4 Hz, 1H), 6.54 (s, 1H), 5.99 (t, J=8.0 Hz, 1H), 4.13-3.95 (m, 2H), 3.72-3.63 (m, 1H), 3.51-3.46 (m, 2H), 3.41 (dt, J=12.7, 4.0 Hz, 1H), 3.02 (dd, J=8.0, 3.0 Hz, 2H), 2.95-2.90 (m, 2H), 2.87-2.83 (m, 2H), 2.82-2.76 (m, 2H), 1.94 (dd, J=6.2, 5.4 Hz, 2H). HPLC retention time (Method #2) 0.823 min.; LCMS (ES): m/z 462.3 [M+H]$^+$.

22B. Isobutyl (S)-3-(6-isobutoxypyridin-3-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoate, TFA: Silver carbonate (104 mg, 0.377 mmol) was added to a solution of 22A (26.0 mg, 0.038 mmol) in Toluene (0.510 mL) and the reaction mixture stirred at 80° C. in a sealed reaction vial for 22 h. After cooling to room temperature, the reaction was filtered through a CELITE® pad, the filtrate was concentrated in vacuo and the residue was purified by Prep. HPLC (XBridge Prep C18 5u OBD 19×100 mm, 10 min gradient, 15 min run, 5% to 100% Solvent B=90% MeOH-10% $H_2O$-0.1% TFA, Solvent A=10% MeOH-90% $H_2O$-0.1% TFA) to afford 22B (2.8 mg, 9.3%) as a yellow oil. $^1$H NMR (500 MHz, $CD_3OD$) δ 8.14 (d, J=2.5 Hz, 1H), 7.73 (dd, J=8.8, 2.5 Hz, 1H), 7.56 (d, J=7.4 Hz, 1H), 6.83 (d, J=8.8 Hz, 1H), 6.71 (d, J=1.7 Hz, 1H), 6.66 (d, J=1.7 Hz, 1H), 6.59 (d, J=7.4 Hz, 1H), 6.20 (t, J=7.8 Hz, 1H), 4.10-4.00 (m, 3H), 3.99-3.92 (m, 1H), 3.84 (d, J=6.6 Hz, 2H), 3.73-3.63 (m, 1H), 3.52-3.46 (m, 2H), 3.36-3.32 (m, 1H), 3.20-3.10 (m, 2H), 2.96-2.90 (m, 2H), 2.87-2.83 (m, 2H), 2.81 (t, J=6.1 Hz, 2H), 2.06 (dt, J=13.3, 6.7 Hz, 1H), 1.97-1.91 (m, 2H), 1.89-1.79 (m, 1H), 1.01 (d, J=6.9 Hz, 6H), 0.87 (dd, J=6.7, 2.9 Hz, 6H). HPLC retention time (Method #2) 1.633 min.; LCMS (ES): m/z 574.5 [M+H]$^+$.

Example 22: Example 22 was prepared using the procedure described for Example 1. $^1$H NMR (500 MHz, $CD_3OD$) δ 8.14 (d, J=2.5 Hz, 1H), 7.73 (dd, J=8.8, 2.5 Hz, 1H), 7.56 (d, J=7.2 Hz, 1H), 6.81 (d, J=8.8 Hz, 1H), 6.71 (d, J=1.7 Hz, 1H), 6.66 (d, J=1.7 Hz, 1H), 6.60 (d, J=7.4 Hz, 1H), 6.18 (t, J=8.1 Hz, 1H), 4.11-4.00 (m, 3H), 4.00-3.94 (m, 1H), 3.70 (ddd, J=12.9, 6.9, 4.4 Hz, 1H), 3.52-3.46 (m, 2H), 3.34-3.32 (m, 1H), 3.14-3.04 (m, 2H), 2.97-2.89 (m, 2H), 2.89-2.82 (m, 2H), 2.81 (t, J=6.1 Hz, 2H), 2.06 (dt, J=13.3, 6.8 Hz, 1H), 1.98-1.90 (m, 2H), 1.01 (d, J=6.6 Hz, 6H). HPLC retention time (Method #2): 1.707 min.; LCMS (ES): m/z 518.5 [M+H]$^+$ The Examples in the following Table (Table 4) were prepared in a similar manner as Example 22. $^1$H NMR was measured at 500 MHz, $CD_3OD$ unless otherwise indicated.

TABLE 4

| Example No. | Structure and Name | Analytical Data |
|---|---|---|
| 23 | 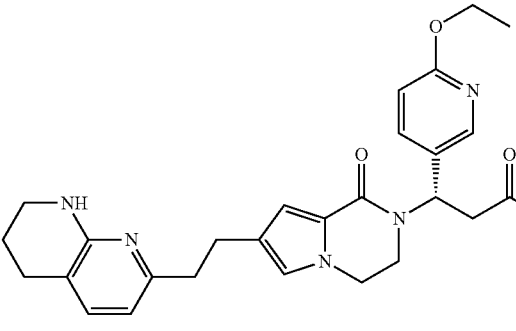<br>(S)-3-(6-Ethoxypyridin-3-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | $^1$H NMR (500 MHz, CD$_3$OD) δ 8.15 (d, J = 2.1 Hz, 1H), 7.71 (dd, J = 8.6, 2.4 Hz, 1H), 7.29 (d, J = 7.2 Hz, 1H), 6.76 (d, J = 8.6 Hz, 1H), 6.60 (d, J = 13.5 Hz, 2H), 6.42 (d, J = 7.3 Hz, 1H), 6.25 (t, J = 8.0 Hz, 1H), 4.29 (q, J = 7.1 Hz, 2H), 4.10-4.00 (m, 1H), 3.96-3.86 (m, 1H), 3.76-3.67 (m, 1H), 3.39 (d, J = 3.9 Hz, 2H), 3.36-3.33 (m, 1H), 2.93 (d, J = 8.1 Hz, 2H), 2.82-2.68 (m, 6H), 1.91-1.82 (m, 2H), 1.36 (t, J = 7.1 Hz, 3H). LCMS (ES): m/z 490.2 [M + H]$^+$. |
| 24 | 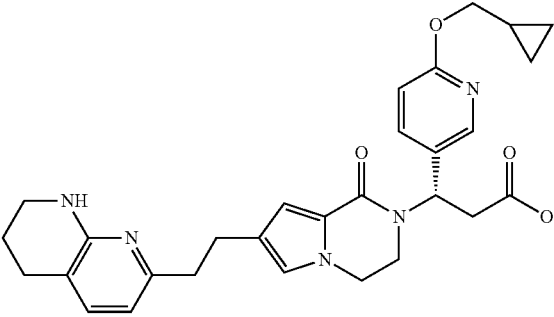<br>(S)-3-(6-(Cyclopropylmethoxy)pyridin-3-yl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid | $^1$H NMR (500 MHz, CD$_3$OD) δ 8.54 (br s, 1H), 8.14 (br s, 1H), 7.71 (br d, J = 7.0 Hz, 1H), 7.11 (br d, J = 6.9 Hz, 1H), 6.82-6.71 (m, 1H), 6.65 (br d, J = 18.4 Hz, 1H), 6.34 (br d, J = 7.3 Hz, 1H), 6.31-6.21 (m, 1H), 4.07 (br d, J = 7.0 Hz, 2H), 3.97-3.90 (m, 1H), 3.74-3.60 (m, 2H), 3.45 (br s, 2H), 3.02 (q, J = 7.5 Hz, 1H), 2.94-2.81 (m, 1H), 2.80-2.56 (m, 4H), 1.99-1.74 (m, 2H), 1.41-1.17 (m, 4H), 0.95-0.84 (m, 1H), 0.66-0.46 (m, 2H), 0.32 (br d, J = 4.7 Hz, 1H). LCMS (ES): m/z 516.2 [M + H]$^+$. |

Example 25

(S)-2-(((Benzyloxy)carbonyl)amino)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid

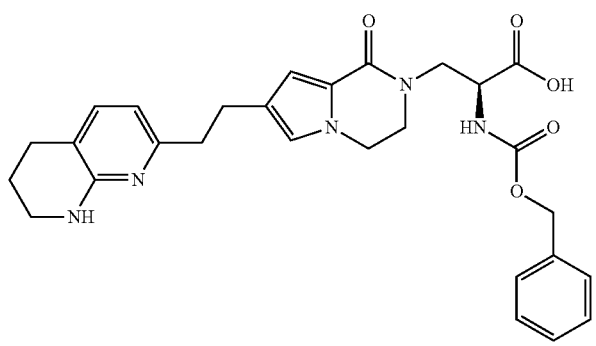

-continued
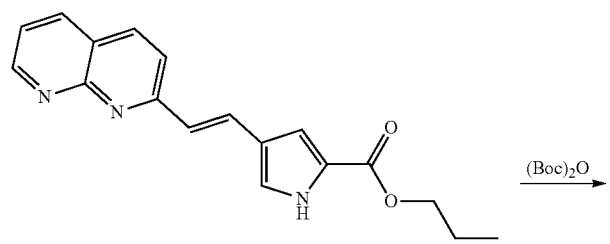
Int-19B → (Boc)₂O →
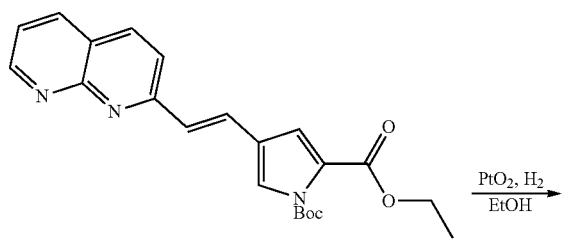
25A → PtO₂, H₂ / EtOH →
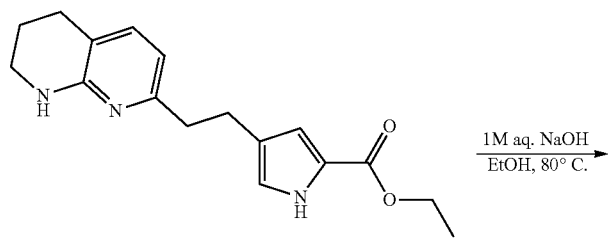
25B → 1M aq. NaOH / EtOH, 80° C. →
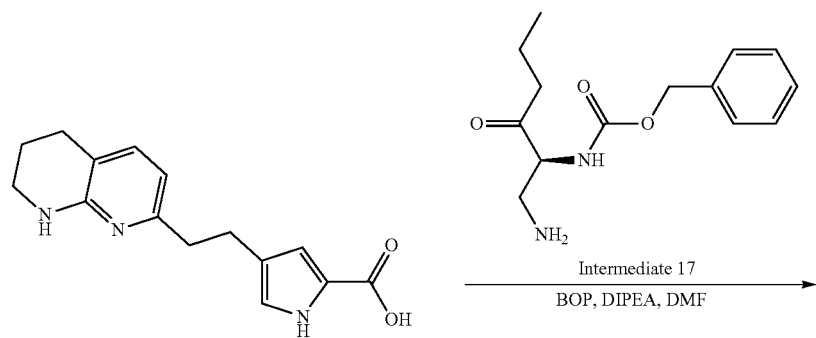
25C
Intermediate 17
BOP, DIPEA, DMF →

-continued

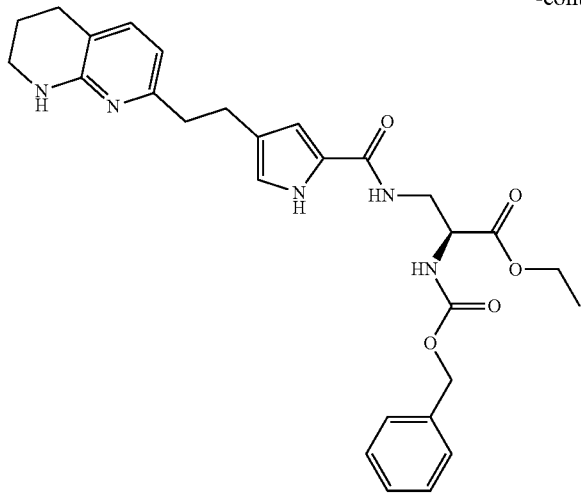 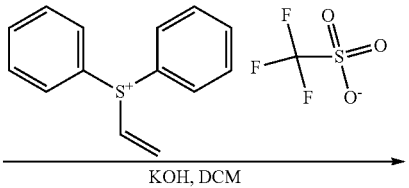

25D → Example 25 (KOH, DCM)

25A. 1-(Tert-butyl) 2-ethyl (E)-4-(2-(1,8-naphthyridin-2-yl)vinyl)-1H-pyrrole-1,2-dicarboxylate: To a solution of Int-19B (2.50 g, 8.52 mmol) in ACN (17.2 mL) were added DMAP (0.104 g, 0.852 mmol) and BOC$_2$O (2.42 g, 11.1 mmol). After stirring at room temperature for 2 h, the reaction was quenched with sat. NH$_4$Cl and diluted with EtOAc (50 mL). The organic layer was washed with sat. NaHCO$_3$, water, brine, dried over anhydrous Na$_2$SO$_4$ and concentrated in vacuo. The residue was purified by flash chromatography (silica gel, DCM:EtOAc, 100:0 to 50:50) to yield 25A (2.40 g, 72%) as a light green solid. $^1$H NMR (500 MHz, CDCl$_3$) δ 9.09 (dd, J=4.1, 1.9 Hz, 1H), 8.18-8.07 (m, 2H), 7.84 (d, J=16.0 Hz, 1H), 7.57 (d, J=8.3 Hz, 1H), 7.51 (d, J=1.7 Hz, 1H), 7.42 (dd, J=8.1, 4.3 Hz, 1H), 7.18-7.06 (m, 2H), 4.35 (q, J=7.0 Hz, 2H), 1.61 (s, 9H), 1.39 (t, J=7.2 Hz, 3H). HPLC retention time (Method #2): 1.973 min.; LCMS (ES): m/z 394.2 [M+H]$^+$.

25B. 1-(Tert-butyl) 2-ethyl 4-(2-(5,6,7,8-tetrahydro-1,8-naphthyridin-2-yl)ethyl)-1H-pyrrole-1,2-dicarboxylate: To a solution of 25A (2.40 g, 6.10 mmol) in EtOH (81 mL) was added PtO$_2$ (0.277 g, 1.22 mmol). The suspension was stirred at room temperature under a H$_2$ atmosphere (1 atm, balloon) for 3.5 h. The slurry was filtered through a CELITE® pad, the filtrate was concentrated in vacuo and the residue was purified by flash chromatography (silica gel, DCM:MeOH, 100:0 to 95:5) to yield 25B (1.46 g, 60%) as an orange oil. $^1$H NMR (500 MHz, CDCl$_3$) δ 7.09 (d, J=1.7 Hz, 1H), 7.06 (d, J=7.4 Hz, 1H), 6.72 (d, J=1.9 Hz, 1H), 6.34 (d, J=7.2 Hz, 1H), 4.78 (br. s., 1H), 4.29 (q, J=7.2 Hz, 2H), 3.46-3.37 (m, 2H), 2.81-2.74 (m, 4H), 2.70 (t, J=6.3 Hz, 2H), 1.92 (quin, J=6.0 Hz, 2H), 1.57 (s, 9H), 1.35 (t, J=7.2 Hz, 3H). HPLC retention time (Method #2): 2.080 min.; LCMS (ES): m/z 400.3 [M+H]$^+$.

25C. 4-(2-(5,6,7,8-Tetrahydro-1,8-naphthyridin-2-yl)ethyl)-1H-pyrrole-2-carboxylic acid, HCl: A solution of NaOH (1.50 g, 37.5 mmol) in water (2.78 mL) was added dropwise to a room temperature solution of 25B (5.00 g, 12.5 mmol) in EtOH (52.8 mL). The reaction was warmed to 80° C. and stirred for 2 h. After cooling to room temperature, the EtOH was removed in vacuo and the residue was acidified to pH~6 with 1M aq. HCl. The precipitate was collected by filtration, washed with water and dried under vacuum. This material was dissolved in 4M HCl in Dioxane (2 mL) and stirred at room temperature for 5 min. The solvent was removed in vacuo to yield 25C (2.03 g, 53%) as an orange solid as the HCl salt. The filtrate was concentrated in vacuo and then purified by reverse phase ISCO chromatography (50 g column—HPC 18 Aq silica gel cartridge, 24 min. run) and eluted with a gradient from to 10% ACN/H$_2$O/TFA (5%/95%/0.05%) to 100% ACN/H$_2$O/TFA (95%0.5%/0.05%) to yield 25C (0.679 g, 14%) as an orange solid as the TFA salt. $^1$H NMR (500 MHz, CD$_3$OD) δ 7.09 (d, J=7.4 Hz, 1H), 6.57-6.51 (m, 2H), 6.34 (d, J=7.4 Hz, 1H), 3.40-3.34 (m, 2H), 2.74 (s, 4H), 2.68 (t, J=6.3 Hz, 2H), 1.96-1.79 (m, 2H). HPLC retention time (Method #2): 0.930 min.; LCMS (ES): m/z 272.1 [M+H]$^+$.

25D. Ethyl (S)-2-(((benzyloxy)carbonyl)amino)-3-(4-(2-(5,6,7,8-tetrahydro-1,8-naphthyridin-2-yl)ethyl)-1H-pyrrole-2-carboxamido)propanoate, TFA: To a solution of 25C (HCl salt) (0.750 g, 2.44 mmol) and Intermediate 17 (0.738 g, 2.44 mmol) in DMF (4.65 mL) were added BOP (1.62 g, 3.66 mmol) and DIPEA (2.13 mL, 12.2 mmol). After stirring at room temperature overnight, the reaction was diluted with water and extracted with EtOAc (3×). The combined organic phases were washed water, brine, dried over anhydrous Na$_2$SO$_4$ and concentrated in vacuo. The residue was purified by flash chromatography (silica gel, DCM:MeOH, 100:0 to 90:10) to yield 25D (1.1 g, 87%) as an off-white solid. $^1$H NMR (500 MHz, DMSO-d$_6$) δ 11.16 (br. s., 1H), 7.97 (t, J=6.1 Hz, 1H), 7.70 (d, J=7.7 Hz, 1H), 7.41-7.20 (m, 5H), 7.06 (d, J=7.2 Hz, 1H), 6.64 (s, 1H), 6.59 (d, J=1.9 Hz, 1H), 6.35 (br. s., 1H), 6.29 (d, J=7.4 Hz, 1H), 5.05 (s, 2H), 4.23 (d, J=7.4 Hz, 1H), 4.07 (q, J=7.2 Hz, 2H), 3.60-3.51 (m, 2H), 3.25 (br. s., 2H), 2.69 (s, 4H), 2.62 (t, J=6.1 Hz, 2H), 1.78-1.71 (m, 2H), 1.13 (t, J=7.0 Hz, 3H). HPLC retention time (Method #2): 1.815 min.; LCMS (ES): m/z 520.3 [M+H]$^+$.

Example 25. To a 0° C. solution of 25D (50 mg, 0.067 mmol) in DCM (4.50 mL) was added KOH (16.9 mg, 0.301 mmol) and the reaction was stirred at 0° C. for 10 min. A solution of diphenylvinylsulfonium triflate (29.1 mg, 0.080 mmol) in DCM (1.12 mL) was added and the reaction mixture was stirred at 0° C. for 10 min. The ice-bath was removed and stirring was continued at room temperature for 3.5 h. The reaction mixture was filtered through a CELITE® pad, the filtrate was concentrated in vacuo and the residue was purified by Prep. HPLC (Phenomenex Luna AXIA 5u C18 21.2×100 mm, 10 min gradient, 12 min run, 5% to 100% Solvent B=90% ACN-10% H$_2$O-0.1% TFA, Solvent A=10% ACN-90% H$_2$O-0.1% TFA) to afford Example 25 (17.3 mg, 40%) as a white solid. $^1$H NMR (400 MHz, CD$_3$OD) δ 7.55 (d, J=7.3 Hz, 1H), 7.32-7.20 (m, 3H), 6.71 (s, 1H), 6.65-6.59 (m, 2H), 5.14-5.08 (m, 1H), 5.03-4.97 (m, 1H), 4.60 (dd, J=9.2, 4.8 Hz, 1H), 3.99-3.90 (m, 3H), 3.80 (dd, J=13.9, 9.5 Hz, 1H), 3.72-3.62 (m, 2H), 3.51-3.44 (m, 2H), 2.94 (d, J=7.0 Hz, 2H), 2.89-2.84 (m, 2H), 2.79 (t, J=6.3 Hz, 2H), 1.93 (quin, J=5.9 Hz, 2H). HPLC retention time (Method #2): 1.467 min.; LCMS (ES): m/z 518.4 [M+H]$^+$.

Example 26

(S)-3-(3-Fluoro-4-methoxyphenyl)-3-(6-iodo-1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid

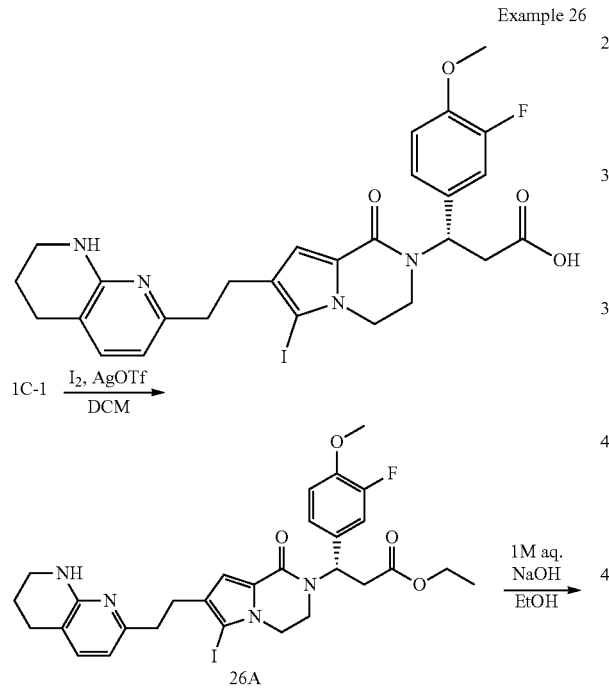

Example 26

26A. Ethyl (S)-3-(3-fluoro-4-methoxyphenyl)-3-(6-iodo-1-oxo-7-(2-(5,6,7,8-tetrahydro-1,8-naphthyridin-2-yl)ethyl)-3,4-dihydropyrrolo[1,2-a]pyrazin-2(1H)-yl)propanoate: 12 (0.024 g, 0.096 mmol) was added portionwise to a 5° C. solution of 1C-1 (0.050 g, 0.096 mmol) and Silver Trifluoroacetate (0.021 g, 0.096 mmol) in DCM (1.0 mL). After stirring at 5° C. for 1 h, the reaction was warmed to room temperature and stirring was continued for 1 h. The reaction mixture was filtered and the filtrate was washed with 5% Na$_2$S$_2$O$_3$ (2×) followed by water. The organic layer was dried over anhydrous Na$_2$SO$_4$ and concentrated in vacuo. The residue was purified by preparative HPLC (Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 41-77% B over 25 minutes, then a 8-minute hold at 100% B; Flow: 20 mL/min.) to afford 26A (23 mg, 35%) as a light yellow solid. $^1$H NMR (500 MHz, CDCl$_3$) δ 7.12-7.04 (m, 3H), 6.95-6.90 (m, 1H), 6.89 (s, 1H), 6.29 (d, J=7.2 Hz, 1H), 6.25 (d, J=7.4 Hz, 1H), 4.17-4.06 (m, 2H), 3.93 (dd, J=7.6, 4.5 Hz, 1H), 3.90-3.82 (m, 4H), 3.59-3.51 (m, 1H), 3.45-3.39 (m, 2H), 3.27 (ddd, J=12.5, 7.7, 4.3 Hz, 1H), 3.04-2.91 (m, 2H), 2.84-2.74 (m, 4H), 2.70 (t, J=6.2 Hz, 2H), 1.90 (dt, J=11.7, 6.0 Hz, 2H), 1.20 (t, J=7.2 Hz, 3H). HPLC retention time (Method #1): 2.620 min.; LCMS (ES): m/z 647.1 [M+H]$^+$.

Example 26: Example 26 was prepared using the procedure described for Example 1. $^1$H NMR (500 MHz, DMSO-d$_6$) δ 7.55 (d, J=7.0 Hz, 1H), 7.28-7.05 (m, 4H), 6.72 (s, 1H), 6.54 (d, J=7.3 Hz, 1H), 5.97 (t, J=7.8 Hz, 1H), 3.86 (d, J=5.2 Hz, 2H), 3.81 (s, 3H), 3.66-3.55 (m, 1H), 3.47 (br. s., 1H), 3.39 (br. s., 1H), 3.28-3.18 (m, 1H), 3.06 (dd, J=15.6, 7.6 Hz, 1H), 2.93-2.82 (m, 3H), 2.75-2.64 (m, 4H), 1.81 (br. s., 2H). LCMS (ES): m/z 619.3 [M+H]$^+$.

Example 27

(S)-3-(3-Fluoro-4-hydroxyphenyl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoic acid

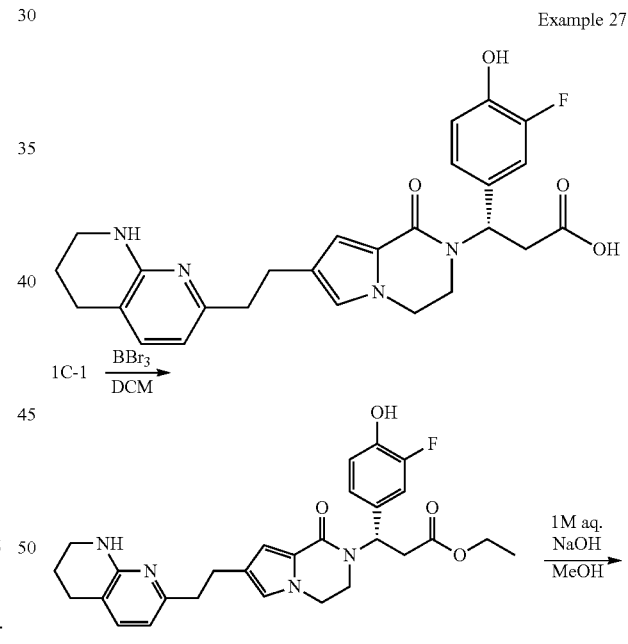

Example 27

27A. Ethyl (S)-3-(3-fluoro-4-hydroxyphenyl)-3-(1-oxo-7-(2-(5,6,7,8-tetrahydro-1,8-naphthyridin-2-yl)ethyl)-3,4-dihydropyrrolo[1,2-a]pyrazin-2(1H)-yl)propanoate: Tribromoborane (1.0 M in hexanes) (0.958 mL, 0.958 mmol) was added dropwise to a 0° C. solution of 1C-1 (0.050 g, 0.096 mmol) in DCM (0.915 mL). After stirring at 0° C. for 30 min., the reaction was slowly quenched with EtOH. The mixture was diluted with DCM and carefully washed with sat. NaHCO$_3$. The organic phase was dried over anhydrous Na$_2$SO$_4$, concentrated in vacuo and the residue was purified by Prep. HPLC (Phenomenex Luna AXIA 5u C18 21.2×100 mm, 10 min gradient, 12 min run, 10% to 100% Solvent B=90% ACN-10% H₂O-0.1% TFA, Solvent A=10% ACN-90% H₂O-0.1% TFA) to afford 27A (22.1 mg, 45%) as a white solid. ¹H NMR (500 MHz, CDCl₃) 7.14-7.04 (m, 2H), 7.01-6.89 (m, 2H), 6.75 (d, J=1.7 Hz, 1H), 6.45 (d, J=1.7 Hz, 1H), 6.36 (d, J=7.2 Hz, 1H), 6.21 (t, J=8.0 Hz, 1H), 5.71 (br. s., 1H), 4.11 (qd, J=7.1, 1.2 Hz, 2H), 3.94 (dd, J=7.6, 4.3 Hz, 1H), 3.89-3.78 (m, 1H), 3.63-3.46 (m, 1H), 3.41 (t, J=5.5 Hz, 2H), 3.25 (ddd, J=12.4, 7.8, 4.3 Hz, 1H), 2.98 (d, J=8.0 Hz, 2H), 2.78 (s, 4H), 2.70 (t, J=6.2 Hz, 2H), 1.96-1.83 (m, 2H), 1.19 (t, J=7.2 Hz, 3H). HPLC retention time (Method #1): 2.062 min.; LCMS (ES): m/z 507.1 [M+H]⁺.

Example 27. Example 27 was prepared using the procedure described for Example 1. ¹H NMR (500 MHz, DMSO-d₆) δ 12.67-11.76 (m, 1H), 10.09-9.61 (m, 1H), 7.08 (dd, J=12.4, 1.9 Hz, 1H), 7.02 (d, J=7.2 Hz, 1H), 6.97-6.92 (m, 1H), 6.91-6.83 (m, 1H), 6.71 (d, J=1.7 Hz, 1H), 6.48 (d, J=1.7 Hz, 1H), 6.28 (d, J=7.2 Hz, 2H), 6.00 (t, J=7.8 Hz, 1H), 4.03-3.84 (m, 2H), 3.53 (d, J=6.3 Hz, 1H), 3.27-3.19 (m, 2H), 3.13 (ddd, J=13.0, 8.2, 4.4 Hz, 1H), 2.93 (br. s., 1H), 2.79 (br. s., 1H), 2.72-2.56 (m, 6H), 1.78-1.68 (m, 2H). HPLC retention time (Method #2): 1.188 min.; LCMS (ES): m/z 479.2 [M+H]⁺.

Example 28

(S)-3-(3-Fluoro-4-methoxyphenyl)-3-(1-oxo-7-(5,6,7,8-tetrahydro-1,8-naphthyridin-2-yl)-3,4-dihydro-pyrrolo[1,2-a]pyrazin-2(1H)-yl)propanoic acid Example 28

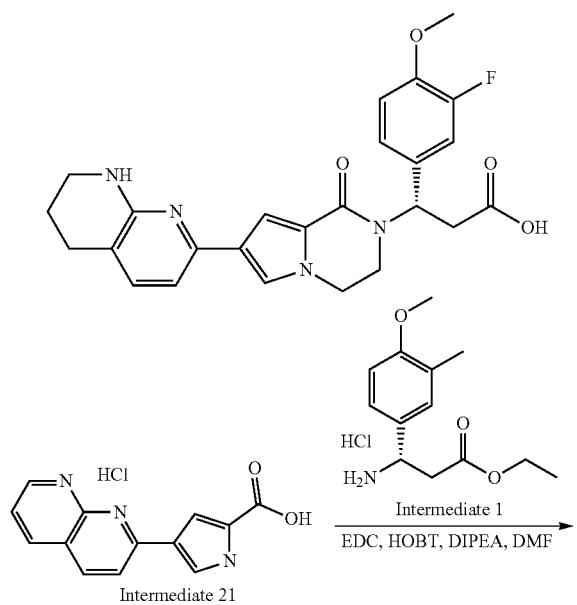

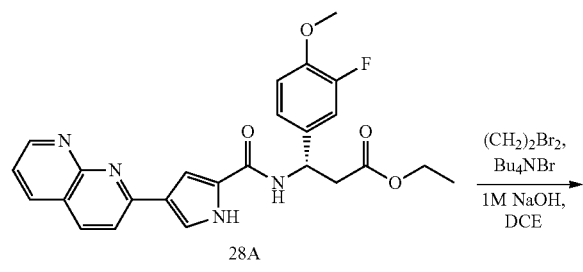

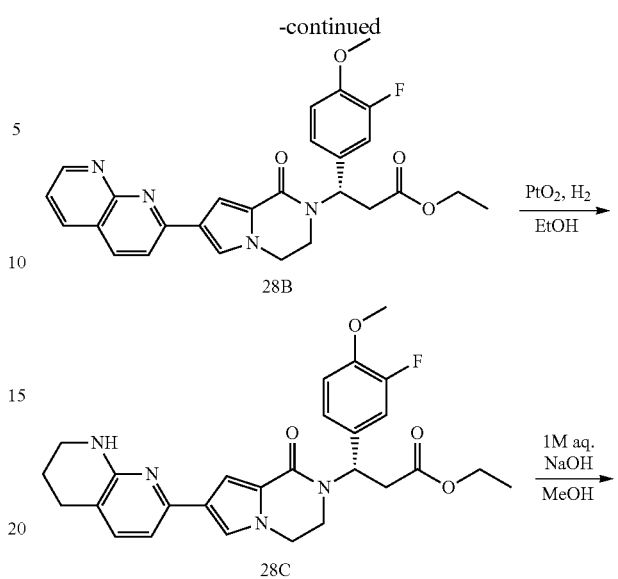

Example 28

28A. Ethyl (S)-3-(4-(1,8-naphthyridin-2-yl)-1H-pyrrole-2-carboxamido)-3-(3-fluoro-4-methoxyphenyl)propanoate: 28A was prepared using the procedure described for 1A. ¹H NMR (500 MHz, DMSO-d₆) δ 11.93 (br. s., 1H), 8.99 (dd, J=4.1, 1.9 Hz, 1H), 8.70 (d, J=8.5 Hz, 1H), 8.42-8.29 (m, 2H), 7.98 (d, J=8.5 Hz, 1H), 7.83 (d, J=1.4 Hz, 1H), 7.73 (s, 1H), 7.50 (dd, J=8.1, 4.3 Hz, 1H), 7.28 (dd, J=12.7, 1.9 Hz, 1H), 7.24-6.99 (m, 3H), 4.06-4.01 (m, 2H), 3.81 (s, 3H), 2.92 (d, J=9.1 Hz, 1H), 2.85 (d, J=6.3 Hz, 1H), 1.12 (t, J=7.0 Hz, 3H). HPLC retention time (Method #1): 2.395 min.; LCMS (ES): m/z 463.1 [M+H]⁺.

28B. Ethyl (S)-3-(7-(1,8-naphthyridin-2-yl)-1-oxo-3,4-dihydropyrrolo[1,2-a]pyrazin-2(1H)-yl)-3-(3-fluoro-4-methoxyphenyl)propanoate: 28B was prepared using the procedure described for 1B. ¹H NMR (500 MHz, CDCl₃) δ 9.11-9.04 (m, 1H), 8.18-8.15 (m, 2H), 7.86-7.82 (m, 1H), 7.80-7.75 (m, 1H), 7.56 (d, J=1.7 Hz, 1H), 7.46-7.39 (m, 1H), 7.17-7.09 (m, 2H), 7.00-6.91 (m, 1H), 6.39-6.34 (m, 1H), 4.19-4.13 (m, 4H), 3.91 (s, 3H), 3.72-3.59 (m, 1H), 3.42-3.27 (m, 1H), 3.05-3.01 (m, 2H), 1.26-1.20 (m, 3H). HPLC retention time (Method #1): 2.438 min.; LCMS (ES): m/z 489.1 [M+H]⁺.

28C. Ethyl (S)-3-(3-fluoro-4-methoxyphenyl)-3-(1-oxo-7-(5,6,7,8-tetrahydro-1,8-naphthyridin-2-yl)-3,4-dihydro-pyrrolo[1,2-a]pyrazin-2(1H)-yl)propanoate: To a solution of 28B (70.4 mg, 0.144 mmol) in EtOH (3.90 mL) was added PtO₂ (6.56 mg, 0.029 mmol). The suspension was stirred at room temperature under a H₂ atmosphere (1 atm., balloon) for 5 h. The slurry was filtered through a CELITE® pad and the filtrate was concentrated in vacuo to afford 28C (63 mg, 88%) as a yellow solid which was used in the next step without purification. LCMS (ES): m/z 493.2 [M+H]⁺.

Example 28: Example 28 was prepared using the procedure described for Example 1. ¹H NMR (500 MHz, DMSO-d₆) δ 12.83-11.59 (m, 1H), 7.34 (d, J=1.7 Hz, 1H), 7.21 (d, J=12.1 Hz, 1H), 7.14 (d, J=5.0 Hz, 2H), 7.08 (d, J=7.7 Hz, 1H), 7.06 (d, J=1.7 Hz, 1H), 6.70 (d, J=7.4 Hz, 1H), 6.20 (s, 1H), 6.06 (t, J=8.0 Hz, 1H), 4.15-3.97 (m, 2H), 3.82 (s, 3H), 3.69-3.55 (m, 1H), 3.28-3.18 (m, 3H), 3.08 (dd, J=15.4, 7.7 Hz, 1H), 2.93 (dd, J=15.4, 8.3 Hz, 1H), 2.62 (t, J=6.1 Hz, 2H), 1.82-1.68 (m, 2H). LCMS (ES): m/z 465.1 [M+H]⁺.

Example 29

(S)-3-(3-Fluoro-4-methoxy phenyl)-3-(1-oxo-7-((5,6,7,8-tetrahydro-1,8-naphthyridin-2-yl)methyl)-3,4-dihydropyrrolo[1,2-a]pyrazin-2(1H)-yl)propanoic acid Example 29

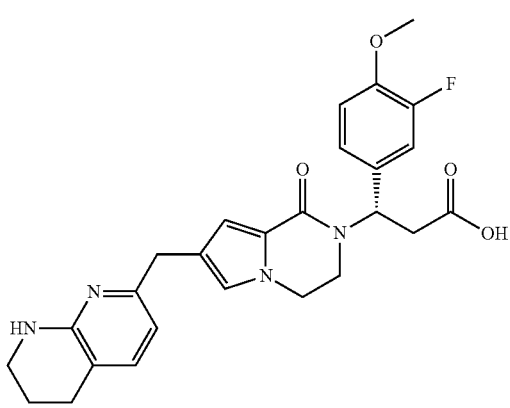

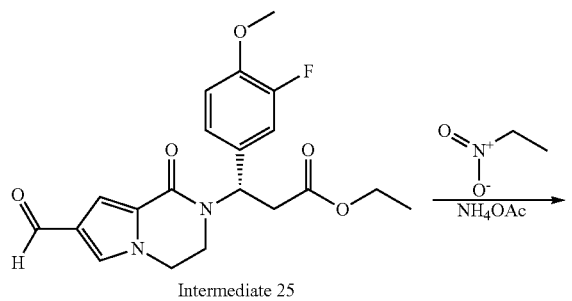

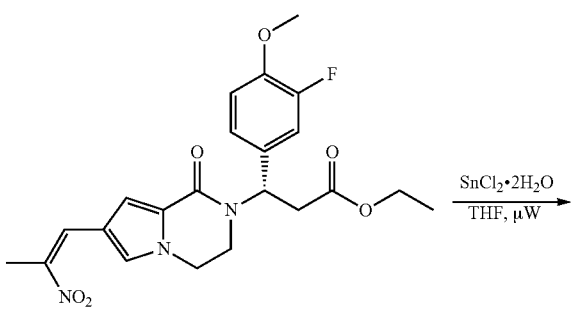

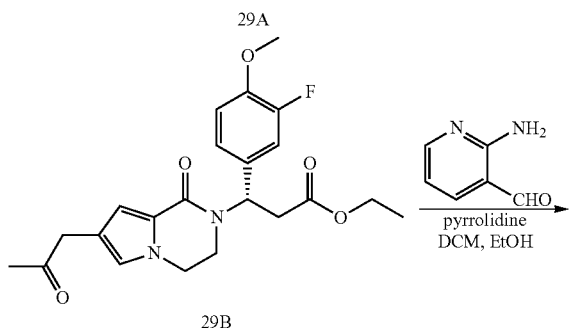

29A. Ethyl (S,Z)-3-(3-fluoro-4-methoxyphenyl)-3-(7-(2-nitroprop-1-en-1-yl)-1-oxo-3,4-dihydropyrrolo[1,2-a]pyrazin-2(1H)-yl)propanoate: A solution of Intermediate 25 (0.215 g, 0.554 mmol) and NH$_4$OAc (0.043 g, 0.554 mmol) in nitroethane (1.11 mL, 15.5 mmol) was stirred at 110° C. for 30 min. The reaction mixture was cooled to room temperature, diluted with water and extracted with DCM (3×). The combined organic layers were washed with brine, dried over anhydrous Na$_2$SO$_4$ and concentrated in vacuo. The residue was purified by flash chromatography (silica gel, hexanes:EtOAc, 100:0 to 0:100) to afford 29A (0.204 g, 83%) as a yellow solid. $^1$H NMR (500 MHz, CDCl$_3$) 7.98 (s, 1H), 7.19 (s, 1H), 7.13-7.05 (m, 2H), 7.01 (s, 1H), 6.97-6.90 (m, 1H), 6.36-6.25 (m, 1H), 4.20-4.09 (m, 3H), 4.03 (ddd, J=12.2, 7.4, 4.3 Hz, 1H), 3.89 (s, 3H), 3.71-3.58 (m, 1H), 3.33 (ddd, J=12.4, 7.8, 4.3 Hz, 1H), 3.07-2.90 (m, 2H), 2.48 (s, 3H), 1.22 (t, J=7.2 Hz, 3H). HPLC retention time (Method #2): 2.482 min.; LCMS (ES): m/z 446.3 [M+H]$^+$.

29B. Ethyl (S)-3-(3-fluoro-4-methoxyphenyl)-3-(1-oxo-7-(2-oxopropyl)-3,4-dihydropyrrolo[1,2-a]pyrazin-2(1H)-yl)propanoate: A mixture of 29A (0.204 g, 0.458 mmol) and Tin (II) Chloride Dihydrate (1.03 g, 4.58 mmol) in THF (2.05 mL) was stirred at 100° C. under μW irradiation for 10 min. The reaction mixture was diluted with a 1:1 mixture (25 mL) of water and DCM and filtered through a CELITE® pad. The filtrate was carefully washed with sat. NaHCO$_3$. The organic layer was separated and washed with brine, dried over anhydrous Na$_2$SO$_4$ and concentrated in vacuo. The residue was purified by flash chromatography (silica gel, hexanes:EtOAc, 100:0 to 25:75) to afford 29B (97 mg, 51%) as a white solid. 1H NMR (500 MHz, CDCl$_3$) δ 7.12-7.04 (m, 2H), 6.96-6.88 (m, 1H), 6.81 (s, 1H), 6.62 (s, 1H), 6.30 (t, J=8.0 Hz, 1H), 4.12 (q, J=7.1 Hz, 2H), 4.01 (dd, J=7.3, 4.5 Hz, 1H), 3.95-3.85 (m, 4H), 3.60-3.48 (m, 3H), 3.27 (ddd, J=12.2, 7.5, 4.3 Hz, 1H), 3.04-2.92 (m, 2H), 2.18

(s, 3H), 1.20 (t, J=7.2 Hz, 3H). HPLC retention time (Method #2): 1.958 min.; LCMS (ES): m/z 417.3 [M+H]+.

29C. Ethyl (S)-3-(7-((1,8-naphthyridin-2-yl)methyl)-1-oxo-3,4-dihydropyrrolo[1,2-a]pyrazin-2(1H)-yl)-3-(3-fluoro-4-methoxyphenyl)propanoate: 29C was prepared using the procedure described for Int-22D. HPLC retention time (Method #2): 1.618 min.; LCMS (ES): m/z 503.4 [M+H]+.

29D. Ethyl (S)-3-(3-fluoro-4-methoxyphenyl)-3-(1-oxo-7-((5,6,7,8-tetrahydro-1,8-naphthyridin-2-yl)methyl)-3,4-dihydropyrrolo[1,2-a]pyrazin-2(1H)-yl)propanoate: 29D was prepared using the procedure described for 28C. LCMS (ES): m/z 507.3 [M+H]+.

Example 29: Example 29 was prepared using the procedure described for Example 1. $^1$H NMR (500 MHz, CD$_3$OD) δ 7.30 (d, J=7.2 Hz, 1H), 7.18-7.10 (m, 2H), 7.05 (t, J=8.5 Hz, 1H), 6.70 (s, 1H), 6.63 (d, J=1.4 Hz, 1H), 6.39 (d, J=7.4 Hz, 1H), 6.25 (t, J=8.1 Hz, 1H), 4.06 (td, J=8.5, 4.3 Hz, 1H), 3.98-3.89 (m, 1H), 3.85 (s, 3H), 3.75-3.64 (m, 3H), 3.40 (dd, J=6.2, 3.4 Hz, 2H), 3.30-3.25 (m, 1H), 2.91 (d, J=8.3 Hz, 2H), 2.72 (t, J=6.2 Hz, 2H), 1.87 (quin, J=5.9, Hz, 2H). HPLC retention time (Method #2): 1.383 min.; LCMS (ES): m/z 479.2 [M+H]+.

Example 30

(S)-3-(6-Methoxypyridin-3-yl)-3-(1-oxo-7-(3-(5,6,7,8-tetrahydro-1,8-naphthyridin-2-yl)propyl)-3,4-dihydropyrrolo[1,2-a]pyrazin-2(1H)-yl)propanoic acid Example 30

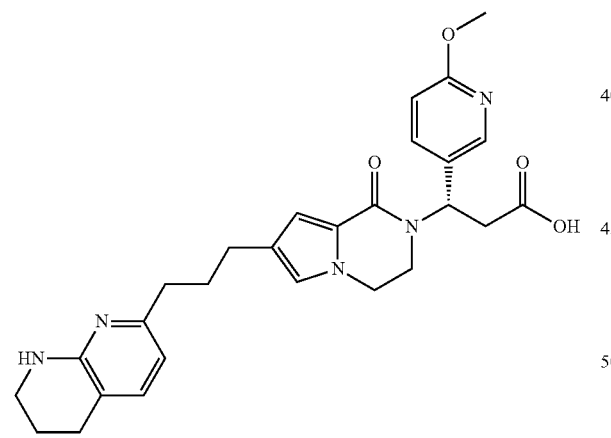

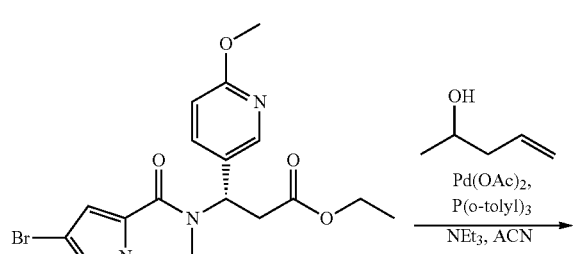

-continued

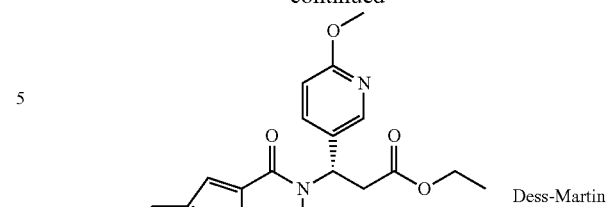

30A

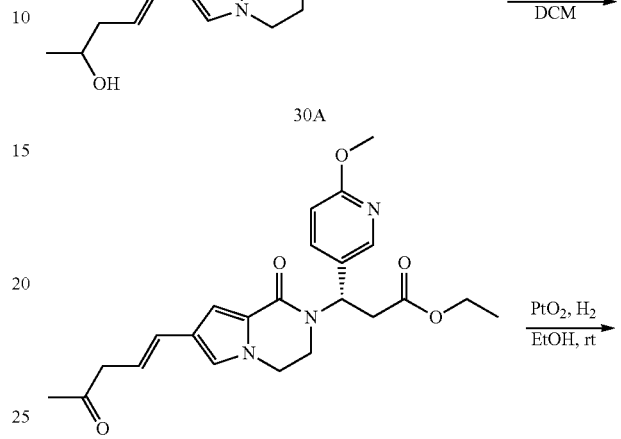

30B

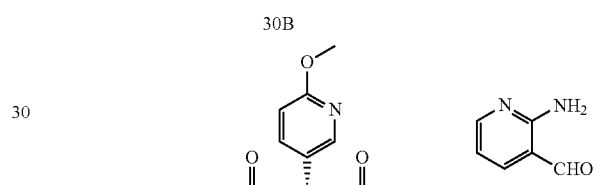

30C

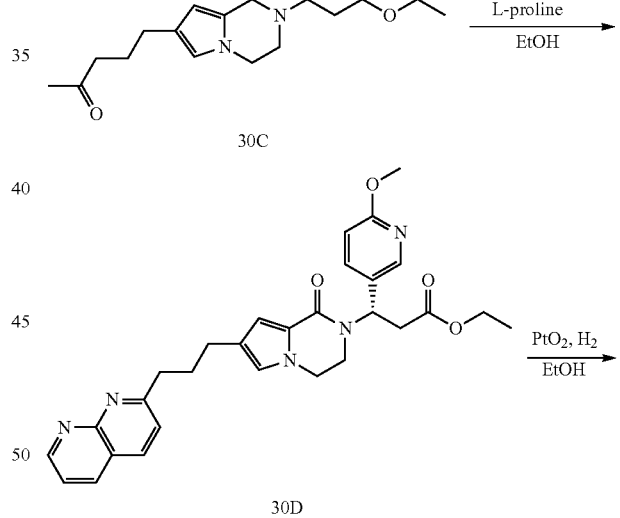

30D

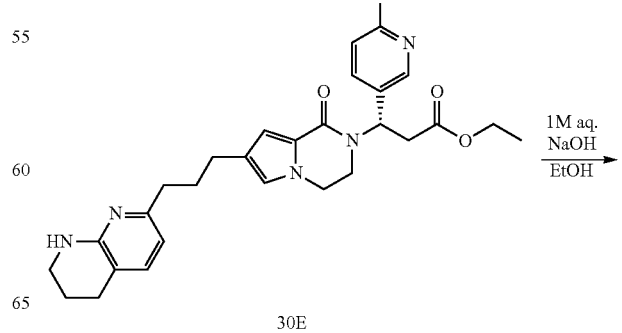

30E

83

-continued

Example 30

30A. Ethyl (3S)-3-(7-((E)-4-hydroxypent-1-en-1-yl)-1-oxo-3,4-dihydropyrrolo[1,2-a]pyrazin-2(1H)-yl)-3-(6-methoxypyridin-3-yl)propanoate: 30A was prepared using the procedure described for Int-1A. $^1$H NMR (500 MHz, CDCl$_3$) δ 8.14 (d, J=2.5 Hz, 1H), 7.63 (dd, J=8.8, 2.5 Hz, 1H), 7.03 (d, J=1.7 Hz, 1H), 6.75 (d, J=8.5 Hz, 1H), 6.68 (d, J=1.4 Hz, 1H), 6.39-6.23 (m, 2H), 5.95 (dd, J=15.4, 8.0 Hz, 1H), 4.18-4.12 (m, 2H), 4.07-4.01 (m, 1H), 4.00-3.86 (m, 5H), 3.61 (ddd, J=12.3, 7.6, 4.3 Hz, 1H), 3.37-3.25 (m, 1H), 3.12-2.99 (m, 2H), 2.42-2.34 (m, 1H), 2.31-2.21 (m, 1H), 1.28-1.17 (m, 6H). HPLC retention time (Method #2): 1.587 min.; LCMS (ES): m/z 428.3 [M+H]$^+$.

30B. Ethyl (S,E)-3-(6-methoxypyridin-3-yl)-3-(1-oxo-7-(4-oxopent-1-en-1-yl)-3,4-dihydropyrrolo[1,2-a]pyrazin-2(1H)-yl)propanoate: Dess-Martin periodinane (0.089 g, 0.211 mmol) was added to a solution of 30A (0.075 g, 0.175 mmol) in DCM (1.64 mL). After stirring at room temperature for 1 h, the reaction was diluted with diethyl ether and filtered through a CELITE® pad. The filtrate was concentrated in vacuo and the residue was purified by flash chromatography (silica gel, DCM:EtOAc, 100:0 to 0:100) to afford 30B (41.1 mg, 55%) as an orange solid. LCMS (ES): m/z 426.3 [M+H]$^+$.

30C. Ethyl (S)-3-(6-methoxypyridin-3-yl)-3-(1-oxo-7-(4-oxopentyl)-3,4-dihydropyrrolo[1,2-a]pyrazin-2(1H)-yl)propanoate: 30C was prepared using the procedure described for 28C. $^1$H NMR (500 MHz, CDCl$_3$) δ 8.12 (d, J=2.5 Hz, 1H), 7.62 (dd, J=8.5, 2.5 Hz, 1H), 6.77 (d, J=1.7 Hz, 1H), 6.73 (d, J=8.5 Hz, 1H), 6.48 (d, J=1.4 Hz, 1H), 6.26 (t, J=8.1 Hz, 1H), 4.13 (q, J=7.2 Hz, 2H), 4.00 (td, J=8.0, 3.7 Hz, 1H), 3.94-3.88 (m, 4H), 3.58 (ddd, J=12.3, 7.6, 4.3 Hz, 1H), 3.29 (ddd, J=12.3, 7.6, 4.3 Hz, 1H), 3.10-2.98 (m, 2H), 2.45 (td, J=7.3, 3.6 Hz, 4H), 2.12 (s, 3H), 1.83 (quin, J=7.4 Hz, 2H), 1.20 (t, J=7.2 Hz, 3H). HPLC retention time (Method #2): 1.717 min.; LCMS (ES): m/z 428.3 [M+H]$^+$.

30D. Ethyl (S)-3-(7-(3-(1,8-naphthyridin-2-yl)propyl)-1-oxo-3,4-dihydropyrrolo[1,2-a]pyrazin-2(1H)-yl)-3-(6-methoxypyridin-3-yl)propanoate: 30D was prepared using the procedure described for Int-19E. $^1$H NMR (500 MHz, CDCl$_3$) δ 9.07 (dd, J=4.3, 2.1 Hz, 1H), 8.15 (dd, J=8.3, 1.9 Hz, 1H), 8.11 (d, J=2.5 Hz, 1H), 8.08 (d, J=8.3 Hz, 1H), 7.61 (dd, J=8.5, 2.5 Hz, 1H), 7.43 (dd, J=8.1, 4.3 Hz, 1H), 7.38 (d, J=8.3 Hz, 1H), 6.79 (d, J=1.7 Hz, 1H), 6.72 (d, J=8.5 Hz, 1H), 6.53 (d, J=1.7 Hz, 1H), 6.26 (t, J=8.0 Hz, 1H), 4.14-4.09 (m, 2H), 3.98 (td, J=8.0, 3.7 Hz, 1H), 3.93-3.85 (m, 4H), 3.60-3.52 (m, 1H), 3.27 (ddd, J=12.4, 7.7, 4.1 Hz, 1H), 3.10-2.98 (m, 4H), 2.57 (t, J=7.4 Hz, 2H), 2.15 (quin, J=7.6 Hz, 2H), 1.21-1.26 (m, 3H). HPLC retention time (Method #2): 1.342 min.; LCMS (ES): m/z 514.4 [M+H]$^+$.

30E. Ethyl (S)-3-(6-methoxypyridin-3-yl)-3-(1-oxo-7-(3-(5,6,7,8-tetrahydro-1,8-naphthyridin-2-yl)propyl)-3,4-dihydropyrrolo[1,2-a]pyrazin-2(1H)-yl)propanoate: 30E was prepared using the procedure described for 28C. $^1$H NMR (500 MHz, CDCl$_3$) δ 8.12 (d, J=2.5 Hz, 1H), 7.62 (dd, J=8.7, 2.6 Hz, 1H), 7.18 (d, J=7.2 Hz, 1H), 6.77 (d, J=1.7 Hz, 1H), 6.73 (d, J=8.5 Hz, 1H), 6.55 (d, J=1.4 Hz, 1H), 6.29-6.21 (m, 2H), 4.12 (q, J=7.2 Hz, 2H), 3.99 (dd, J=7.6, 4.5 Hz, 1H), 3.94-3.85 (m, 4H), 3.58 (ddd, J=12.3, 7.6, 4.3 Hz, 1H), 3.49-3.40 (m, 2H), 3.29 (ddd, J=12.3, 7.6, 4.3 Hz, 1H), 3.08-2.98 (m, 2H), 2.73-2.62 (m, 4H), 2.50 (t, J=7.4 Hz, 2H), 1.96-1.82 (m, 4H), 1.20 (t, J=7.2 Hz, 3H). HPLC retention time (Method #2): 1.612 min.; LCMS (ES): m/z 518.4 [M+H]$^+$.

84

Example 30: Example 30 was prepared using the procedure described for Example 1. $^1$H NMR (500 MHz, CDCl$_3$) δ 14.57 (br. s., 1H), 9.47 (br. s., 1H), 8.17 (d, J=1.4 Hz, 1H), 7.66 (dd, J=8.7, 2.1 Hz, 1H), 7.34 (d, J=7.4 Hz, 1H), 6.77 (d, J=8.5 Hz, 1H), 6.70 (s, 1H), 6.62 (s, 1H), 6.37 (d, J=7.2 Hz, 1H), 6.31 (dd, J=10.0, 5.6 Hz, 1H), 4.01 (td, J=8.0, 3.7 Hz, 1H), 3.96 (s, 3H), 3.93-3.87 (m, 1H), 3.63-3.54 (m, 1H), 3.49 (br. s., 2H), 3.29 (ddd, J=12.3, 7.8, 4.1 Hz, 1H), 3.16-3.08 (m, 1H), 3.07-2.94 (m, 1H), 2.76 (t, J=6.1 Hz, 2H), 2.71-2.61 (m, 2H), 2.50 (t, J=7.0 Hz, 2H), 1.98-1.87 (m, 4H). HPLC retention time (Method #2): 1.290 min.; LCMS (ES): m/z 490.1 [M+H]$^+$.

Example 31

(S)-3-(3-Fluoro-4-methoxyphenyl)-3-(1-oxo-7-(4-(5,6,7,8-tetrahydro-1,8-naphthyridin-2-yl)butyl)-3,4-dihydropyrrolo[1,2-a]pyrazin-2(1H)-yl)propanoic acid

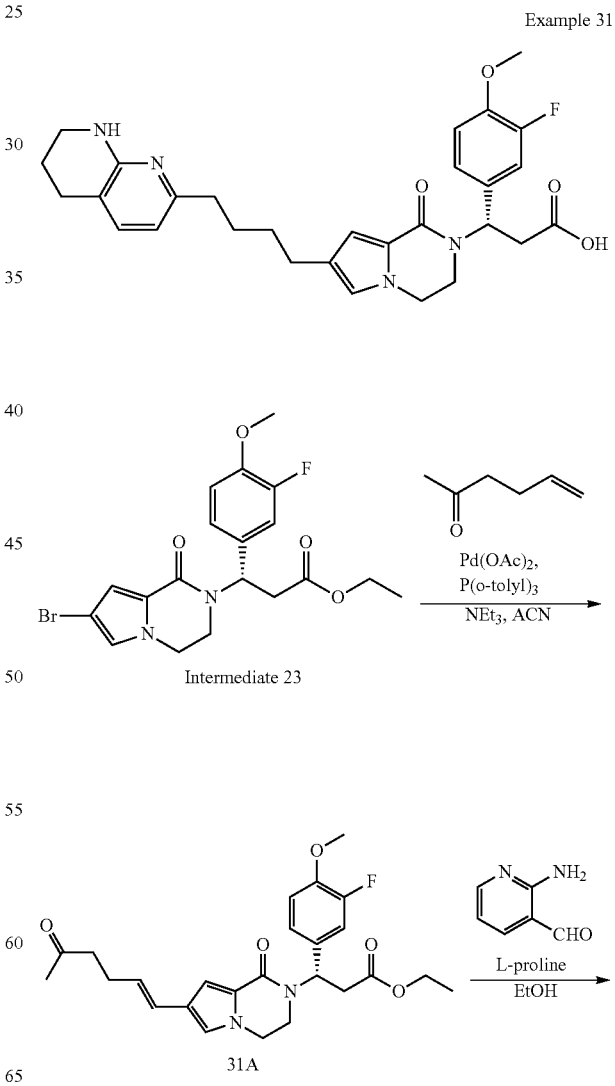

Example 31

Intermediate 23

31A

-continued

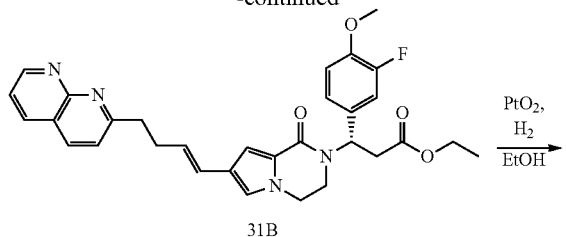

31B

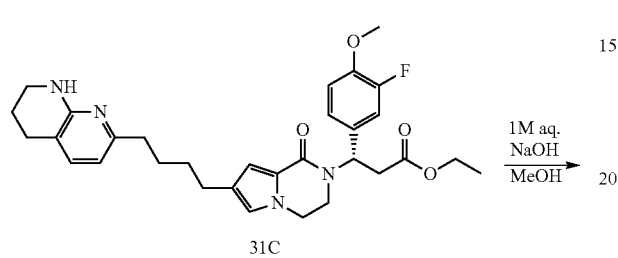

31C

Example 31

31A. Ethyl (S,E)-3-(3-fluoro-4-methoxy phenyl)-3-(1-oxo-7-(5-oxohex-1-en-1-yl)-3,4-dihydropyrrolo[1,2-a]pyrazin-2(1H)-yl)propanoate: 31A was prepared using the procedure described for Int-1A. HPLC retention time (Method #1): 3.068 min.; LCMS (ES): m/z 457.2 [M+H]$^+$.

31B. Ethyl (S,E)-3-(7-(4-(1,8-naphthyridin-2-yl)but-1-en-1-yl)-1-oxo-3,4-dihydropyrrolo[1,2-a]pyrazin-2 (1H)-yl)-3-(3-fluoro-4-methoxy phenyl)propanoate: A solution of 31A (17.7 mg, 0.039 mmol), 2-aminonicotinaldehyde (6.16 mg, 0.050 mmol) and L-proline (4.46 mg, 0.039 mmol) in EtOH (0.194 mL) was stirred at reflux for 18 h. After cooling to room temperature, the solvent was removed in vacuo and the residue was purified by preparative HPLC (Phenomenex Luna AXIA 5u C18 21.2×100 mm, 10 min gradient, 12 min run, 0% to 100% Solvent B=90% MeOH-10% H$_2$O-0.1% TFA, Solvent A=10% MeOH-90% H$_2$O-0.1% TFA) to afford 21.2 mg of the TFA salt of 31B. This material was dissolved in MeOH (0.250 mL) and 100 mg Dianion WA21J resin was added. After stirring at room temperature for 1 h, the resin was removed by filtration and washed well with MeOH. The filtrate was concentrated in vacuo to afford 31B (15.0 mg, 71%) as a yellow solid. LCMS (ES): m/z 543.3 [M+14]$^+$.

31C. Ethyl (S)-3-(3-fluoro-4-methoxyphenyl)-3-(1-oxo-7-(4-(5,6,7,8-tetrahydro-1,8-naphthyridin-2-yl)butyl)-3,4-dihydropyrrolo[1,2-a]pyrazin-2(1H)-yl)propanoate: 31C was prepared using the procedure described for 28C. HPLC retention time (Method #1): 2.660 min.; LCMS (ES): m/z 549.3 [M+H]$^+$.

Example 31: Example 31 was prepared using the procedure described for Example 1. $^1$H NMR (500 MHz, DMSO-d$_6$) δ 7.18-7.06 (m, 3H), 7.02 (d, J=7.3 Hz, 1H), 6.68 (s, 1H), 6.49 (s, 1H), 6.24 (d, J=7.0 Hz, 1H), 6.01 (t, J=7.6 Hz, 1H), 3.99-3.87 (m, 2H), 3.80 (s, 3H), 3.59 (br. s., 1H), 3.22 (br. s., 2H), 3.15 (d, J=9.2 Hz, 1H), 3.05-2.98 (m, 1H), 2.91-2.82 (m, 1H), 2.61-2.56 (m, 2H), 2.41 (t, J=7.2 Hz, 2H), 2.35 (t, J=7.0 Hz, 2H), 1.72 (br. s., 2H), 1.54 (d, J=7.3 Hz, 2H), 1.46 (d, J=7.0 Hz, 2H). LCMS (ES): m/z 521.5 [M+H]$^+$.

Example 32

(S)-3-(3-Fluoro-4-methoxyphenyl)-3-(1-oxo-7-(4-(5,6,7,8-tetrahydro-1,8-naphthyridin-2-yl)butyl)-3,4-dihydropyrrolo[1,2-a]pyrazin-2(1H)-yl)propanoic acid, TFA

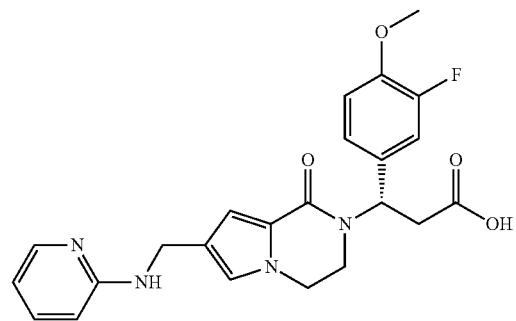

Example 32

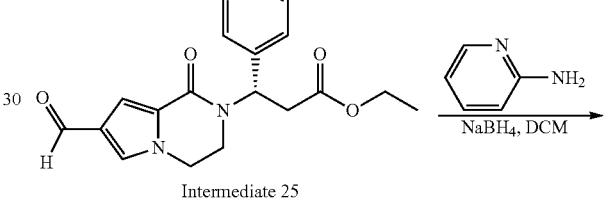

Intermediate 25

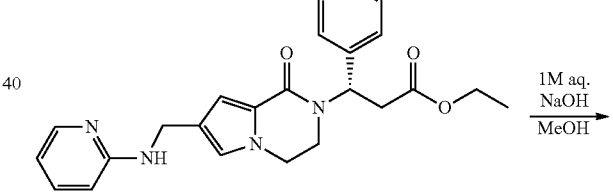

32A

Example 32

32A. Ethyl (S)-3-(3-fluoro-4-methoxyphenyl)-3-(1-oxo-7-((pyridin-2-ylamino)methyl)-3,4-dihydropyrrolo[1,2-a]pyrazin-2(1H)-yl)propanoate: A mixture of Intermediate 25 (10 mg, 0.026 mmol), pyridin-2-amine (2.42 mg, 0.026 mmol) and NaBH$_4$ (1.95 mg, 0.051 mmol) in DCM (0.257 mL) was stirred at room temperature for 10 min. The reaction mixture was quenched with water and extracted with DCM. The organic layer was dried over anhydrous Na$_2$SO$_4$, filtered and concentrated in vacuo to afford 32A (11.2 mg, 93%) as a crude yellow oil which was used in the next step without further purification. LCMS (ES): m/z 467.1 [M+H]$^+$.

Example 32: Example 32 was prepared using the procedure described for Example 1. NMR (500 MHz, DMSO-d$_6$) δ 7.93 (br d, J=5.8 Hz, 1H), 7.80 (br t, J=7.5 Hz, 1H), 7.20-7.08 (m, 4H), 7.00-6.93 (m, 2H), 6.79 (br t, J=6.4 Hz, 1H), 6.71 (s, 1H), 6.02 (br t, J=7.9 Hz, 1H), 4.34 (s, 2H), 4.07-3.93 (m, 2H), 3.81 (s, 3H), 3.64-3.52 (m, 1H), 3.17 (br d, J=8.2 Hz, 1H), 3.10-3.01 (m, 1H), 2.91 (br dd, J=15.4, 8.4 Hz, 1H). LCMS (ES): m/z 439.4 [M+H]⁺.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:

1. A compound of Formula I:

$$\text{(Structure I)}$$

or a pharmaceutically acceptable salt or stereoisomer thereof,
wherein:
X is a bond, -(alkylene)-, -(alkylene)-NR$^7$—, -(alkylene)-O—, -(alkylene)-S—, —NR$^7$—, —O—, or —S—;
R$^1$ is hydrogen, halo, or alkyl;
R$^2$ is —NHC(NH)NH$_2$, —NH(dihydroimidazolyl), —NH(imidazolyl), —NH(tetrahydropyrimidinyl), —NH(pyridinyl), —NH(benzoimidazolyl), tetrahydronaphthyridinyl, naphthyridinyl, dihydropyridooxazinyl, tetrahydropyridopyrazinyl, tetrahydropyridoazepinyl, tetrahydropyridooxazepinyl, dihydroimidazoimidazolyl, or tetrahydroimidazopyrimidinyl, each optionally substituted with 1 or 2 independently selected alkyl substituents; or
X and R$^2$, taken together, form —CH[CH$_2$(tetrahydronaphthyridinyl)]$_2$;
R$^3$ is hydrogen, halo, or alkyl;
R$^4$ is hydrogen or Ar$^1$;
R$^5$ is hydrogen, —NHC(O)OCH$_2$(phenyl), or —NHS(O)$_2$Ar$^1$;
R$^6$ is hydrogen or alkyl;
R$^7$ is hydrogen or alkyl; and
each Ar$^1$ is independently dihydrobenzofuranyl, phenyl, naphthyl, pyridinyl, pyridazinyl, pyrimidinyl, pyrazinyl, quinolinyl, or quinoxalinyl, each optionally substituted with 1, 2, or 3 substituents independently selected from the group consisting of halo, cyano, alkyl, haloalkyl, OH, —O(alkyl), —O(haloalkyl), and —O-(alkylene)-cycloalkyl.

2. The compound of claim 1, or a pharmaceutically acceptable salt or stereoisomer thereof, wherein:
X is a bond or -(alkylene)-;
R$^1$ is hydrogen or halo;
R$^2$ is —NHC(NH)NH$_2$, —NH(dihydroimidazolyl), —NH(imidazolyl), —NH(tetrahydropyrimidinyl), —NH(pyridinyl), —NH(benzoimidazolyl), tetrahydronaphthyridinyl, naphthyridinyl, dihydropyridooxazinyl, tetrahydropyridopyrazinyl, tetrahydropyridoazepinyl, tetrahydropyridooxazepinyl, dihydroimidazoimidazolyl, or tetrahydroimidazopyrimidinyl, each optionally substituted with 1 or 2 independently selected alkyl substituents;
R$^3$ is hydrogen;
R$^4$ is hydrogen or Ar$^1$;
R$^5$ is hydrogen, —NHC(O)OCH$_2$(phenyl), or —NHS(O)$_2$Ar$^1$;
R$^6$ is hydrogen or alkyl; and
each Ar$^1$ is independently dihydrobenzofuranyl, phenyl, naphthyl, pyridinyl, pyridazinyl, pyrimidinyl, pyrazinyl, quinolinyl, or quinoxalinyl, each optionally substituted with 1 or 2 substituents independently selected from the group consisting of halo, cyano, alkyl, haloalkyl, OH, —O(alkyl), —O(haloalkyl), and —O-(alkylene)-cycloalkyl.

3. The compound of claim 1, or a pharmaceutically acceptable salt or stereoisomer thereof, wherein X is a bond or -(alkylene)-.

4. The compound of claim 1, or a pharmaceutically acceptable salt or stereoisomer thereof, wherein R$^1$ is hydrogen or halo.

5. The compound of claim 1, or a pharmaceutically acceptable salt or stereoisomer thereof, wherein R$^2$ is —NH(pyridinyl), tetrahydronaphthyridinyl, or naphthyridinyl, each optionally substituted with 1 or 2 independently selected alkyl substituents.

6. The compound of claim 1, or a pharmaceutically acceptable salt or stereoisomer thereof, wherein R$^3$ is hydrogen.

7. The compound of claim 1, or a pharmaceutically acceptable salt or stereoisomer thereof, wherein:
R$^4$ is Ar$^1$; and
R$^5$ is hydrogen.

8. The compound of claim 1, or a pharmaceutically acceptable salt or stereoisomer thereof, wherein:
R$^4$ is hydrogen; and
R$^5$ is —NHC(O)OCH$_2$(phenyl) or —NHS(O)$_2$Ar$^1$.

9. The compound of claim 1, or a pharmaceutically acceptable salt or stereoisomer thereof, wherein each Ar$^1$ is independently phenyl, pyridinyl, or pyrimidinyl, each optionally substituted with 1, 2, or 3 substituents independently selected from the group consisting of halo, cyano, alkyl, haloalkyl, OH, —O(alkyl), —O(haloalkyl), and —O-(alkylene)-cycloalkyl.

10. The compound of claim 1, or a pharmaceutically acceptable salt or stereoisomer thereof, wherein the compound, or pharmaceutically acceptable salt or stereoisomer thereof, is selected from the group consisting of:

$$\text{(Structure 1)}$$

-continued
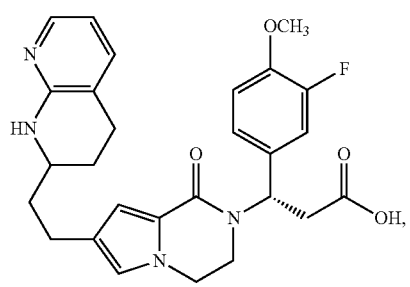
(2)
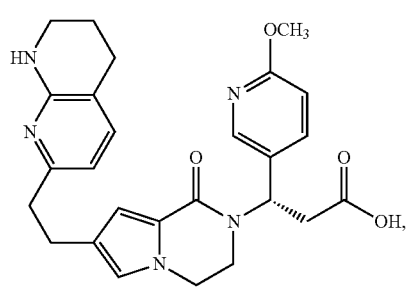
(3)
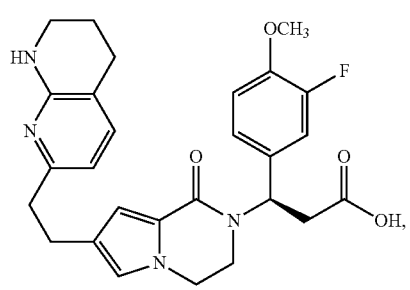
(4)
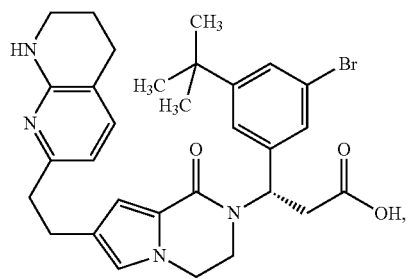
(5)
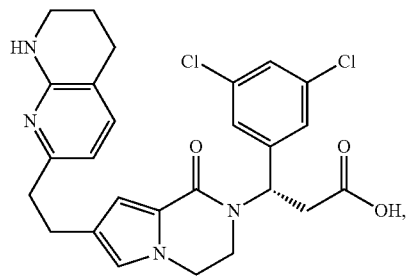
(6)
-continued
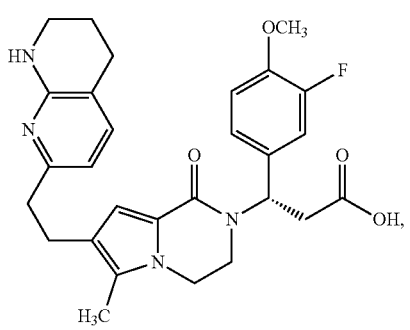
(7)
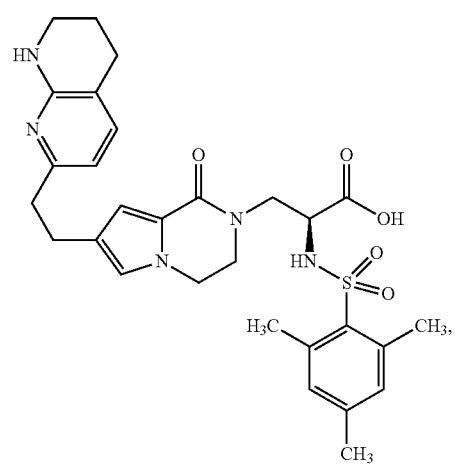
(8)
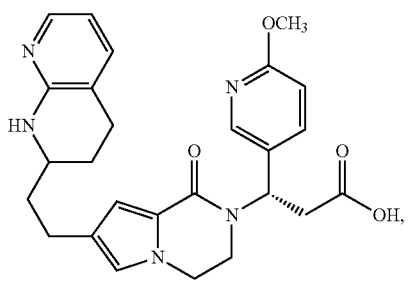
(9)
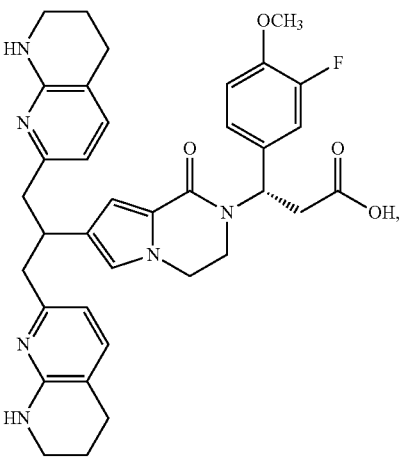
(10)

(11-12)
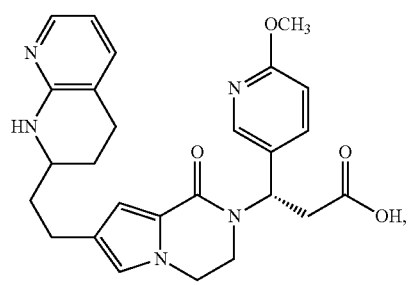
(13)
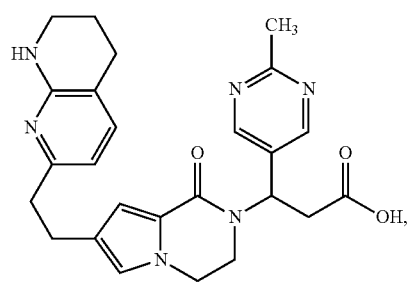
(14)
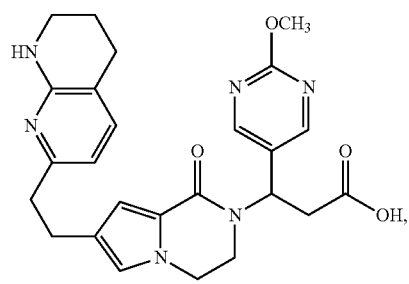
(15)
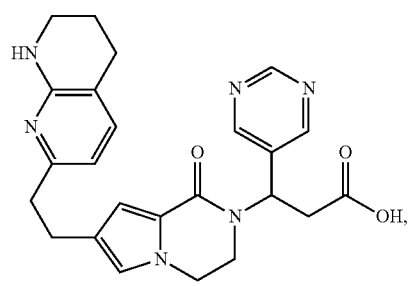
(16)
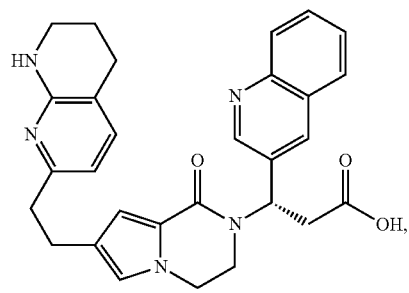
(17)
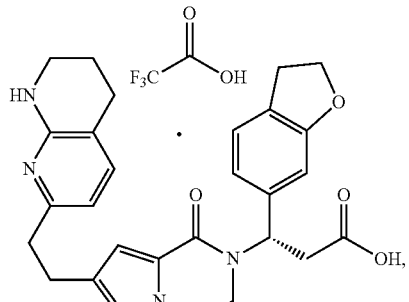
(18)
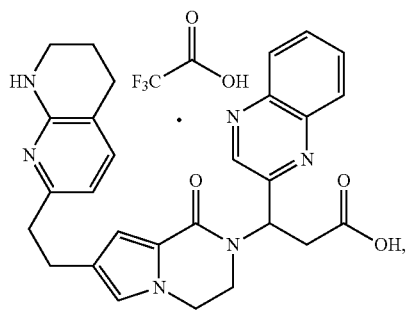
(19)
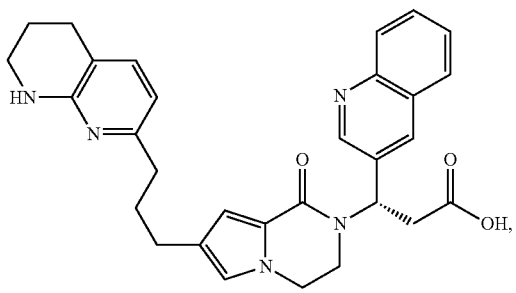
(20)
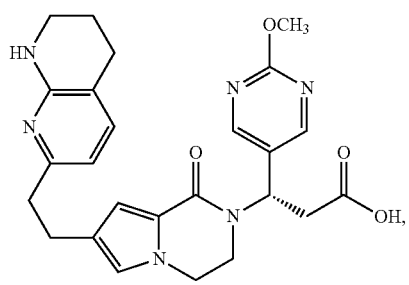
(21)
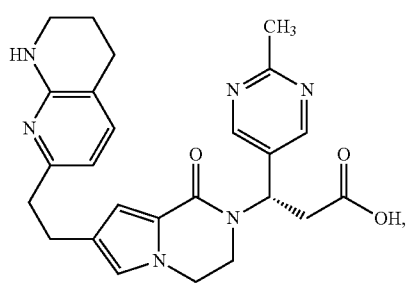

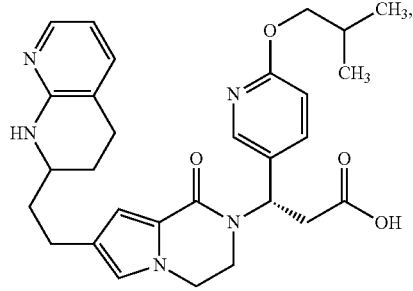
(22)
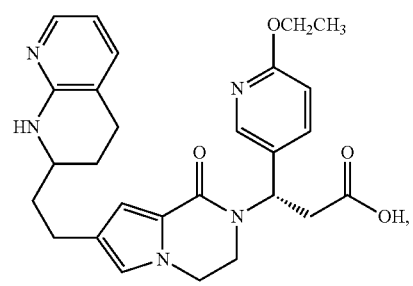
(23)
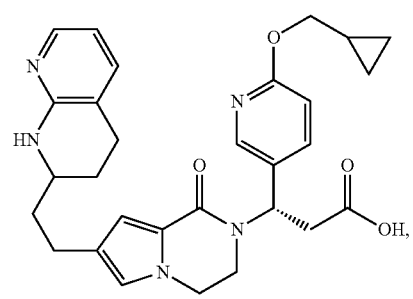
(24)
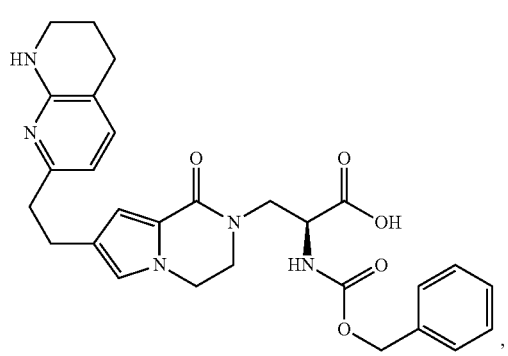
(25)
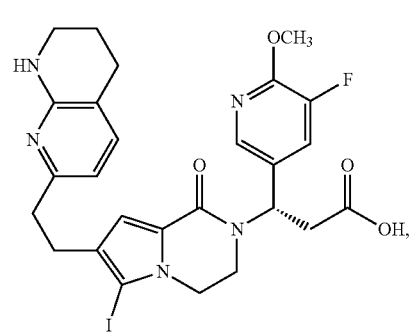
(26)
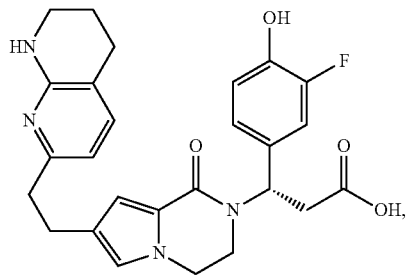
(27)
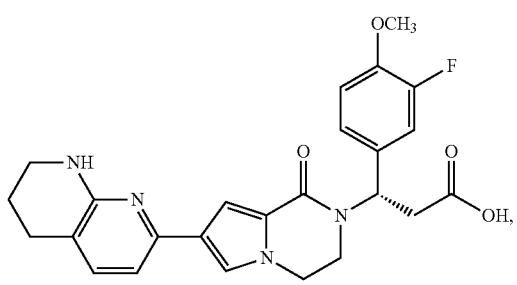
(28)
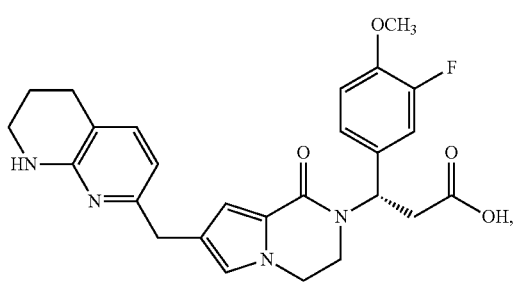
(29)
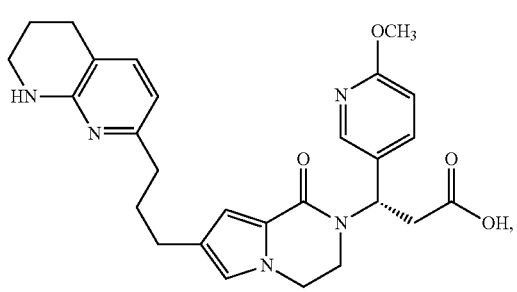
(30)
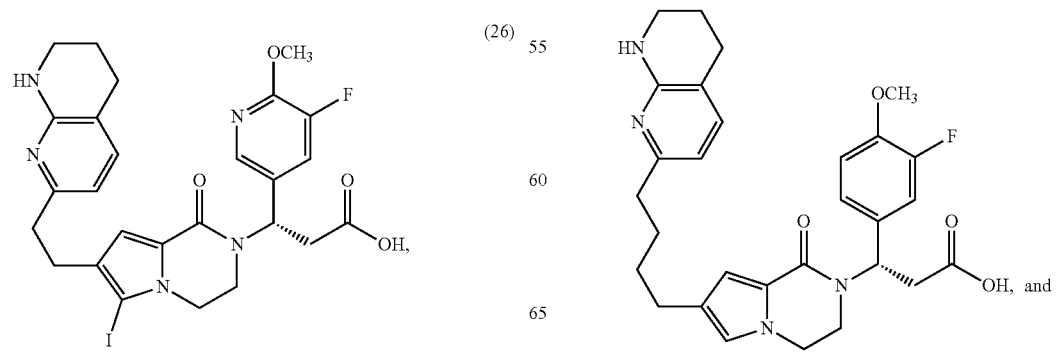
(31)

-continued (32)

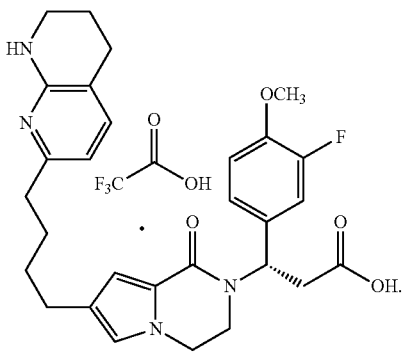

11. A pharmaceutical composition comprising a pharmaceutically acceptable carrier and a compound of claim 1, or a pharmaceutically acceptable salt or stereoisomer thereof.

12. A method for inhibiting alpha-V integrin activity in a patient in need thereof, wherein the method comprises administering to the patient a therapeutically effective amount of a compound of claim 1, or a pharmaceutically acceptable salt or stereoisomer thereof.

13. The method of claim 12, wherein the patient has a disease, disorder, or condition selected from the group consisting of a cancer, an inflammatory disorder, osteoporosis, a pathological fibrosis, and transplant rejection.

14. The method of claim 13, wherein the cancer is selected from the group consisting of bladder cancer, blood cancer, bone cancer, brain cancer, breast cancer, central nervous system cancer, cervical cancer, colon cancer, endometrial cancer, esophageal cancer, gallbladder cancer, genital cancer, genitourinary tract cancer, head cancer, kidney cancer, large intestine cancer, larynx cancer, liver cancer, lung cancer, muscle tissue cancer, neck cancer, oral cancer, nasal mucosa cancer, ovarian cancer, pancreatic cancer, prostate cancer, skin cancer, spleen cancer, small intestine cancer, stomach cancer, testicular cancer, and thyroid cancer.

15. The method of claim 13, wherein the pathological fibrosis is selected from the group consisting of cardiac fibrosis, dermal fibrosis, hepatic fibrosis, ocular fibrosis, pancreatic fibrosis, pulmonary fibrosis, and renal fibrosis.

16. The method of claim 12, wherein the patient has a disease, disorder, or condition selected from the group consisting of chronic kidney disease, diabetic kidney disease, idiopathic pulmonary fibrosis, nonalcoholic steatohepatitis, and systemic sclerosis.

* * * * *

UNITED STATES PATENT AND TRADEMARK OFFICE
CERTIFICATE OF CORRECTION

PATENT NO. : 11,292,802 B2
APPLICATION NO. : 16/761286
DATED : April 5, 2022
INVENTOR(S) : Guohua Zhao et al.

Page 1 of 2

It is certified that error appears in the above-identified patent and that said Letters Patent is hereby corrected as shown below:

On the Title Page

Column 2 (Abstract), Line 2, Delete "α$_v$-containing" and insert -- αv-containing --.

In the Claims

Claim 1, Column 87, Lines 22-31 (Approx.), delete "

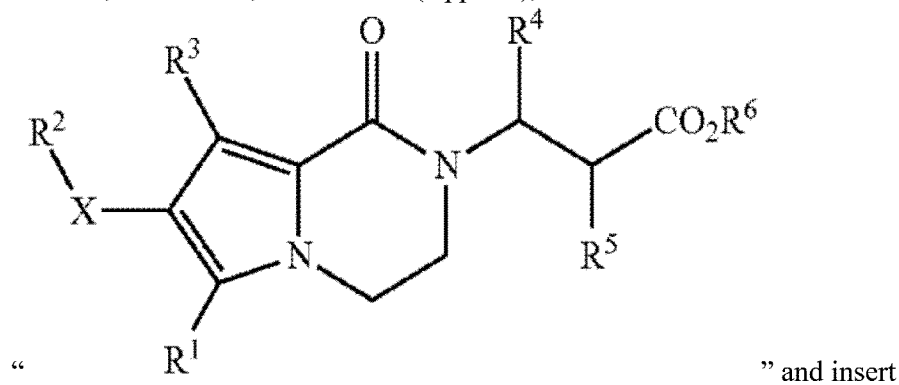

" and insert

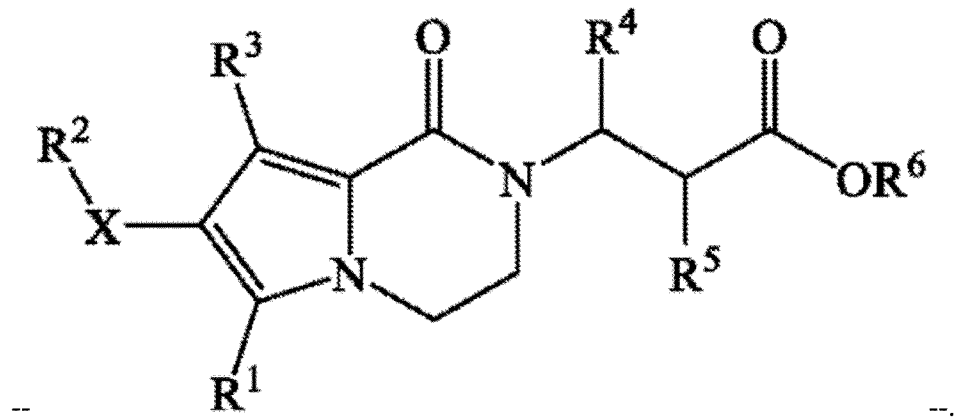

--.

Signed and Sealed this
Thirtieth Day of September, 2025

John A. Squires
*Director of the United States Patent and Trademark Office*

Claim 2, Column 88, Lines 12-13 (Approx.), delete "—NHS(O) $_2$Ar$^1$;" and insert -- —NHS(O)$_2$Ar$^1$; --.